US012098018B2

(12) United States Patent
Nau et al.

(10) Patent No.: US 12,098,018 B2
(45) Date of Patent: Sep. 24, 2024

(54) NESTING STRUCTURES FOR STORAGE, TRANSPORT, AND ASSEMBLY OF DRUG DISPENSERS AND CONTAINERS

(71) Applicant: Oyster Point Pharma, Inc., Princeton, NJ (US)

(72) Inventors: Jeffrey Alan Nau, Pennington, NJ (US); George J. Donato, Swarthmore, PA (US); Travis D. Buel, Hickman, NE (US); Charles E. McCall, Jr., Fuquay Varina, NC (US); Joseph Vincent Ranalletta, Greenville, SC (US)

(73) Assignee: Oyster Point Pharma, Inc., Princeton, NJ (US)

( * ) Notice: Subject to any disclaimer, the term of this patent is extended or adjusted under 35 U.S.C. 154(b) by 766 days.

(21) Appl. No.: 17/150,905

(22) Filed: Jan. 15, 2021

(65) Prior Publication Data
US 2022/0227566 A1   Jul. 21, 2022

(51) Int. Cl.
*B65D 83/04* (2006.01)
*A61J 1/16* (2023.01)

(52) U.S. Cl.
CPC .......... *B65D 83/0409* (2013.01); *A61J 1/16* (2013.01); *B65D 2215/04* (2013.01)

(58) Field of Classification Search
CPC ..... B65D 83/0409; B65D 2215/04; A61J 1/16
See application file for complete search history.

(56) References Cited

U.S. PATENT DOCUMENTS

| | | | |
|---|---|---|---|
| 7,096,896 B2 * | 8/2006 | Py | B65B 55/04 |
| | | | 141/130 |
| 8,118,167 B2 * | 2/2012 | Togashi | A61B 50/30 |
| | | | 206/519 |
| 8,347,589 B2 | 1/2013 | Duquet | |
| 8,360,238 B2 | 1/2013 | Nicoletti et al. | |
| 8,469,185 B2 | 6/2013 | Nicoletti et al. | |
| 8,561,828 B2 | 10/2013 | Krauss et al. | |
| 8,794,442 B2 | 8/2014 | Nicoletti et al. | |
| 8,813,963 B2 | 8/2014 | Nicoletti et al. | |
| 8,939,288 B2 | 1/2015 | Gagnieux | |

(Continued)

FOREIGN PATENT DOCUMENTS

| | | |
|---|---|---|
| DE | 102004021668 A1 | 12/2005 |
| KR | 20100008261 U | 8/2010 |

(Continued)

OTHER PUBLICATIONS

International Search Report and Written Opinion for International Application No. PCT/US2022/012441, mailed Jun. 10, 2022, 19 pages.

(Continued)

*Primary Examiner* — Thomas M Wittenschlaeger
*Assistant Examiner* — David G Shutty

(57) ABSTRACT

Various nesting structures for storage, transport and/or assembly of dispensers and containers are described herein. For example, a packaging structure for a plurality of drug dispensers may include a support surface and a plurality of dispenser covers arranged on the support surface, where at least one dispenser cover includes a locking flexure member configured to couple a dispenser to the at least one dispenser cover.

9 Claims, 41 Drawing Sheets

(56) References Cited

U.S. PATENT DOCUMENTS

| | | | |
|---|---|---|---|
| 9,072,637 B1* | 7/2015 | Puri | A61G 7/05 |
| 9,156,598 B2 | 10/2015 | Nicoletti et al. | |
| 9,718,583 B2 | 8/2017 | Nicoletti et al. | |
| 9,937,288 B2 | 4/2018 | Wright et al. | |
| 9,963,259 B2* | 5/2018 | Deutschle | F26B 25/003 |
| 10,195,111 B2 | 2/2019 | Glocker et al. | |
| 10,196,161 B2 | 2/2019 | Broadbent et al. | |
| 10,207,832 B2* | 2/2019 | Narvekar | A61J 1/1412 |
| 10,399,768 B2 | 9/2019 | Bertolin | |
| 10,434,242 B2 | 10/2019 | Thompson et al. | |
| 10,874,473 B2* | 12/2020 | Togashi | B65D 81/20 |
| 10,881,796 B2* | 1/2021 | Wei | A61M 5/3204 |
| 2007/0233021 A1* | 10/2007 | Poisson | A61M 35/003 604/295 |
| 2010/0233099 A1* | 9/2010 | Whiting | A61P 25/06 424/45 |
| 2012/0118777 A1* | 5/2012 | Kakiuchi | A61M 5/002 29/428 |
| 2019/0041132 A1 | 2/2019 | McCann et al. | |
| 2019/0350806 A1 | 11/2019 | Langsdorf et al. | |
| 2019/0352038 A1 | 11/2019 | Langsdorf et al. | |
| 2020/0277112 A1* | 9/2020 | Gift | B65D 47/08 |
| 2021/0220547 A1* | 7/2021 | Sonoyama | A61M 5/008 |
| 2021/0236714 A1* | 8/2021 | Limaye | A61M 5/3205 |
| 2022/0371765 A1* | 11/2022 | Hutterer | A61J 1/16 |

FOREIGN PATENT DOCUMENTS

| | | | | |
|---|---|---|---|---|
| WO | WO-2014049713 A1 * | 4/2014 | | A61M 5/008 |
| WO | WO-2018020505 A1 | 2/2018 | | |
| WO | WO 2018-198028 A1 | 11/2018 | | |
| WO | WO 2019-171192 A1 | 9/2019 | | |

OTHER PUBLICATIONS

Invitation to Pay Fee for International Application No. PCT/US2022/012441 dated Apr. 5, 2022, 15 pages.

* cited by examiner

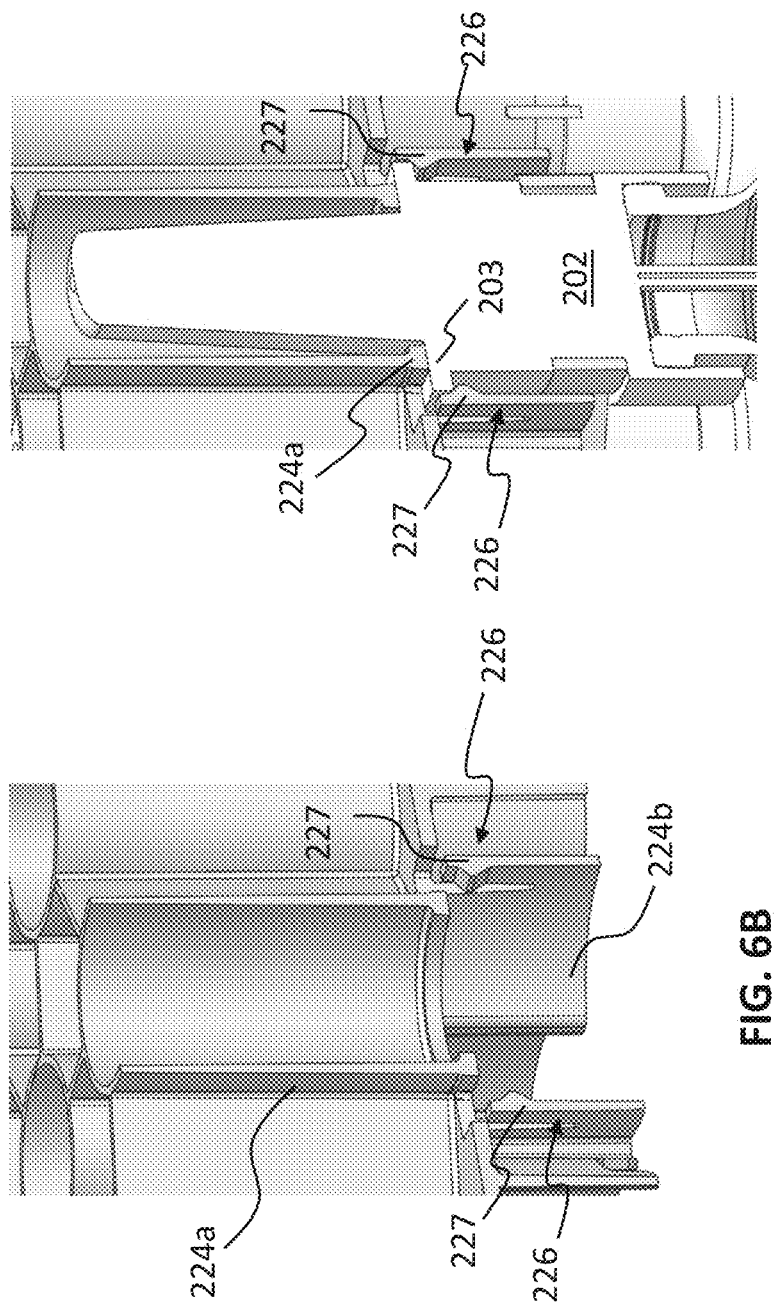

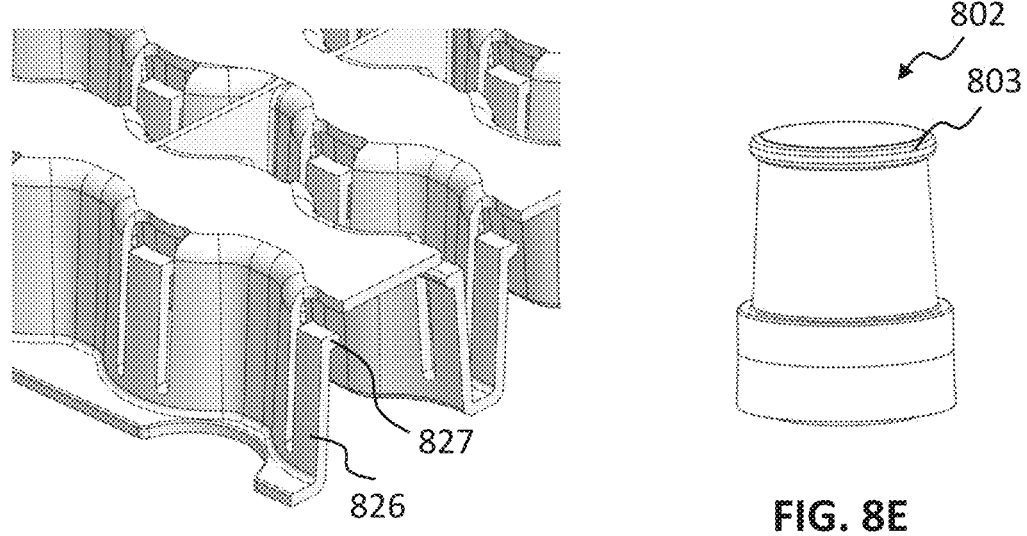
FIG. 8D
FIG. 8E
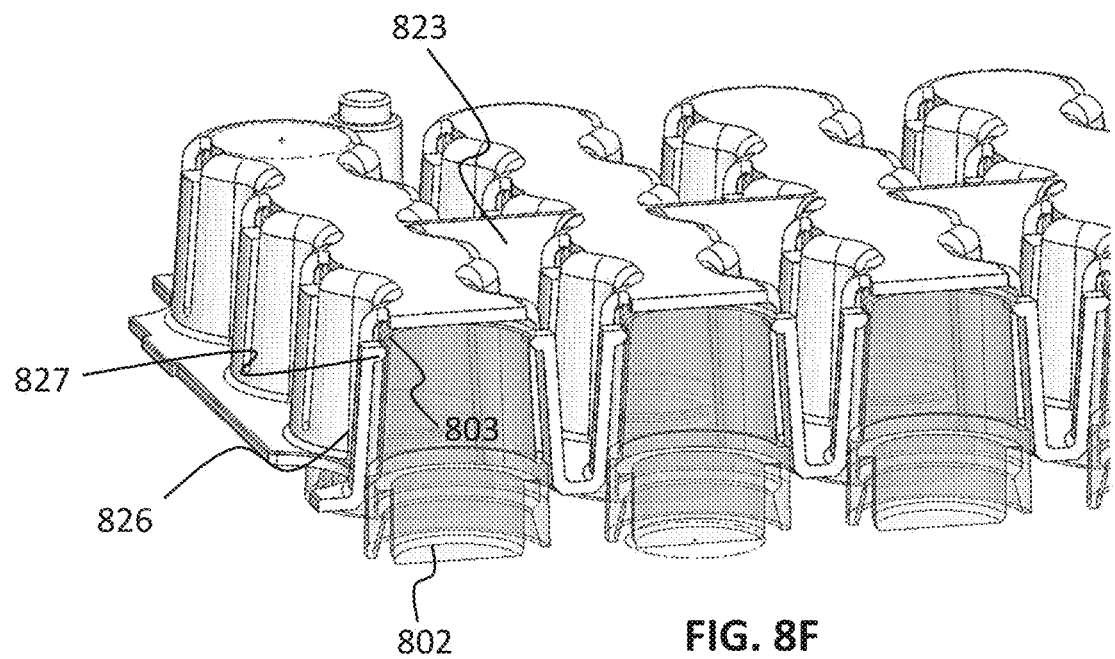
FIG. 8F

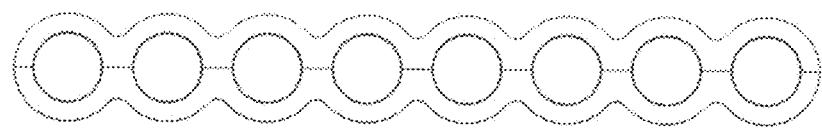
FIG. 21C
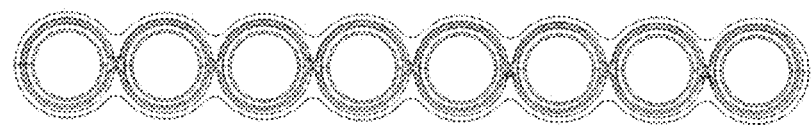
FIG. 21D
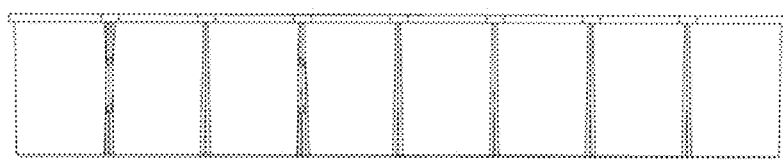 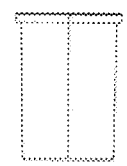
FIG. 21E FIG. 21F

NESTING STRUCTURES FOR STORAGE, TRANSPORT, AND ASSEMBLY OF DRUG DISPENSERS AND CONTAINERS

TECHNICAL FIELD

This invention relates generally to the field of packaging structures, such as for the packaging of drug dispensers and containers.

BACKGROUND

Production and transport of pharmaceuticals often involves processes that occur at mass scale. For example, large quantities of drug containers and/or dispensers may be manufactured separately, then transported to other equipment that performs sterilization, filling, assembly, and/or other processes. Assembled containers and/or their associated dispensers may then be transported for further distribution.

While at least some of these processes can be performed by equipment in an automated manner to improve efficiency and product output, care must be taken when manipulating certain kinds of products. For example, many containers are made of glass and are prone to breakage if not handled properly. Similarly, it can be important to carefully handle fragile or delicate containers or dispensers to avoid breakage or deformation. Additionally, irregularly-shaped items may be difficult to handle in a space-efficient manner, or may become entangled or disorganized if not carefully managed. Furthermore, such large-scale manufacturing and distribution processes may also be subject to various governmental regulations to ensure product safety, such as maintaining sterility, which may further complicate packaging procedures.

Thus, there is a need for new and improved packaging structures, such as for the storage, transport and assembly of drug dispensers and containers.

SUMMARY

In some variations, a packaging structure for a plurality of dispensers (e.g., drug dispensers) may include a support surface, and a plurality of dispenser covers arranged on the support surface, where at least one dispenser cover may include a locking flexure member configured to couple a dispenser to the at least one dispenser cover. The packaging structure may, for example, be included in a packaging assembly that further includes a plurality of drug dispensers coupled to the dispenser covers. At least one of such drug dispensers may include a cover for a drug container. The drug dispensers in the packaging assembly may, for example, include a spray pump (e.g., nasal spray pump) or a drop dispenser (e.g., eyedropper) that is configured to couple to a drug container.

In some variations, a packaging structure for a plurality of dispensers (e.g., drug dispensers) may include a support surface and a plurality of dispenser seats arranged on the support surface, where at least one dispenser seat may include a base having an opening, a wall extending from the base, and at least one alignment feature configured to engage with an engagement feature in a dispenser to thereby orient the dispenser in the at least one dispenser seat. The packaging structure may, for example, be included in a packaging assembly that further includes a plurality of drug dispensers. At least one of such drug dispensers may include a cover for a drug container. The drug dispensers in the packaging assembly may, for example, include a spray pump (e.g., nasal spray pump) or a drop dispenser (e.g., eyedropper) that is configured to couple to a drug container.

In some variations, a packaging assembly may include a base, a plurality of containers arranged on the base, and at least one reinforcement member coupled to at least one container. The containers may include a first material having a first rigidity, and the at least one reinforcement member may include a second material having a second rigidity that is greater than the first rigidity. The containers may, for example, be configured to couple to a drug dispenser such as a drop dispenser (e.g., eyedropper).

A method for assembling dispenser assemblies may include providing a first support structure comprising a plurality of dispenser covers and providing a second support structure comprising a plurality of container seats. A plurality of dispensers may be coupled to the dispenser covers (e.g., with one or more locking members), and a plurality of containers may be seated in the container seats. The method may further include filling the containers with a substance (e.g., drug (such as a liquid drug), such as a preservative-free drug) to be dispensed from the container, then aligning the first and second support structures to align the plurality of dispensers with the plurality of containers. After the first and second support structures are aligned, the first support structure and/or the second support structure may be manipulated to simultaneously couple the plurality of dispensers to the plurality of containers.

BRIEF DESCRIPTION OF THE DRAWINGS

FIGS. 6B and 6C depict detailed views of a dispenser cover with locking members in an example variation of a pump nest, without and with a pump, respectively.

FIG. 8D depicts a cross-sectional view of an example variation of a dropper nest.

FIG. 8E depicts a detailed view of an example variation of a drop dispenser in a dropper nest assembly.

FIG. 8F depicts a detailed cross-sectional view of an example variation of a dropper nest with drop dispensers.

FIGS. 21C-21F are a top view, a bottom view, a front view, and a side view, respectively, of the reinforcement members shown in FIG. 21A.

DETAILED DESCRIPTION

Non-limiting examples of various aspects and variations of the invention are described herein and illustrated in the accompanying drawings.

Described herein are variations of packaging structures for use in processing containers and/or other accompanying items such as container covers (e.g., dispensers) during processes such as storage, transport, and/or assembly. For example, in some variations, nested packaging structures such as those described herein may be used to handle drug containers and/or drug dispensers. Also described herein are methods of assembling containers and dispensers using such packaging structures.

Nesting Packaging Structures

Figure 1:
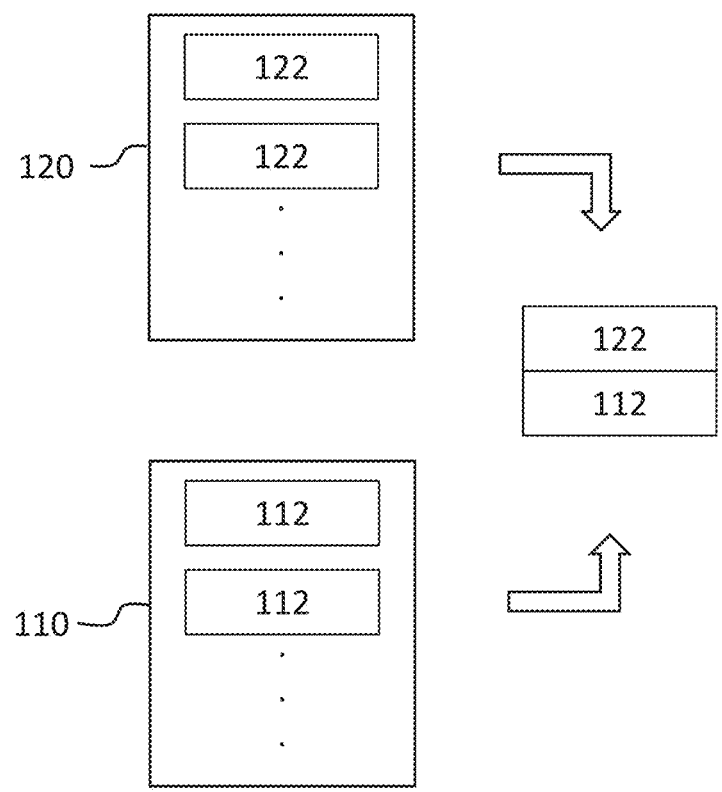
FIG. 1 depicts a schematic illustration of nested packaging structures and their combined use.

FIG. 1 depicts a schematic illustration of nested packaging structures for different components and their use. In some variations, a first packaging assembly 110 may include one or more packaging structures 112 (e.g., trays) for a first component type. For example, components of the first component type may be nested (e.g., in a protective, organized manner) in a packaging structure 112. For sake of illustration, the first component type may, for example, include containers (e.g., bottles) for pharmaceutical drugs. The first packaging assembly 110 may include a single packaging structure 112 that contains multiple items of the first component type, or may include multiple such packaging structures 112 that are stacked or otherwise layered. In some variations, the first packaging assembly 110 may further include a tub that receives the one or more packaging structures 112. The tub may be sealed or otherwise covered to help contain the packaging structure(s) 112 in the tub, such as with foil or a film. Prior to sealing, the packaging structure(s) 112 and components contained therein may be sterilized (e.g., with a sterilant gas such as ethylene oxide, etc.).

Similarly, a second packaging assembly 120 may include one or more packaging structures 122 (e.g., trays) for a second component type. For example, components of the first component type may be nested (e.g., in a protective, organized manner) in a packaging structure 122. The second component type may, for example include container covers (e.g., dispensers, lids, caps, etc.), and may be configured to couple to the first component type. Like the first packaging assembly, the second packaging assembly 120 may include a single packaging structure 122 that contains multiple items of the second component type, or may include multiple such packaging structures 122 that are stacked or otherwise layered. In some variations, the second packaging assembly 120 may further include a tub that receives the one or more packaging structures 122. The tub may be sealed or otherwise covered to help contain the packaging structure(s) 122 in the tub, such as with foil or a film. Prior to sealing, the packaging structure(s) 112 and components contained therein may be sterilized (e.g., with gamma ray sterilization, with a sterilant gas such as ethylene oxide, etc.).

The packaging structures 112 and 122 may enable simultaneous, collective manipulation of large quantities of the components contained therein. For example, the packaging structures 112 and/or 122 may be manipulated so as to substantially simultaneously couple components contained in the packaging structure 112 to components contained in the packaging structure 122. Accordingly, components among the first packaging assembly 110 may be coupled to the components among the second packaging assembly 120 in an efficient manner. Furthermore, components in the first and second packaging structures may be protected against breakage, disorganization, etc. throughout such manipulation, at least in part because components among the first packaging assembly 110 may be nested in the first packaging structure 122, and components among the second packaging assembly 120 may be nested in the second packaging structure 122. Illustrative examples of packaging structures as described in further detail below.

Pump Nest Assembly

Figure 2A:
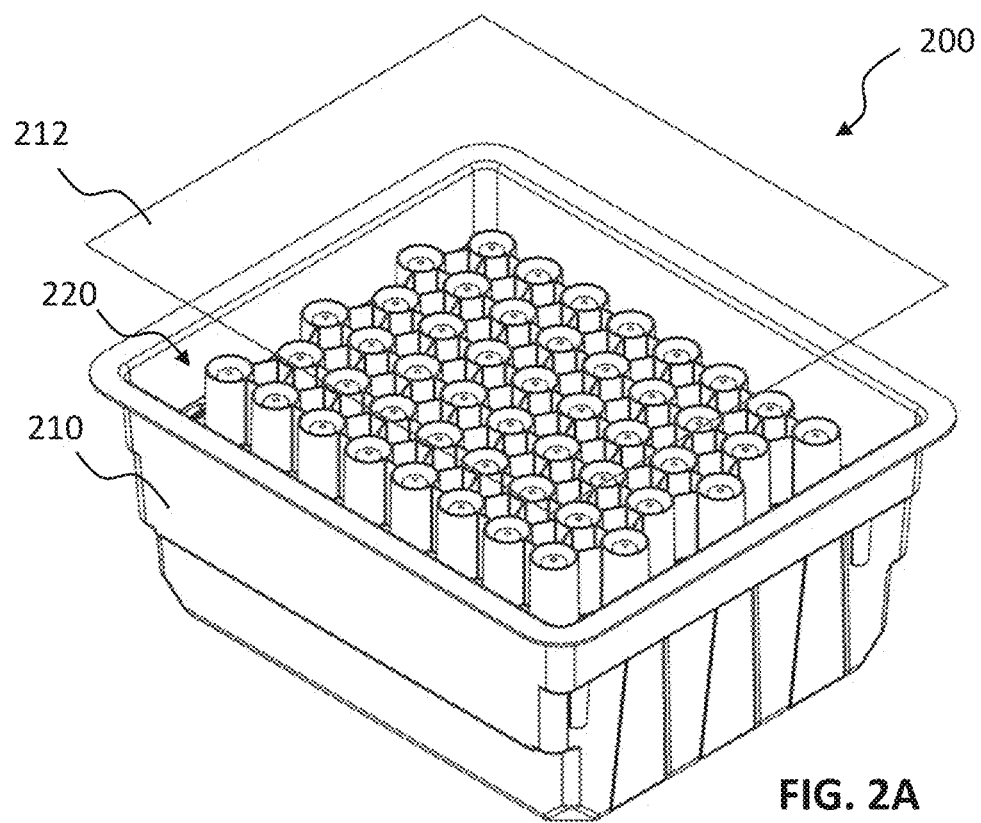
FIG. 2A depicts a schematic illustration of an example variation of a pump nest assembly.

FIG. 2A depicts a schematic illustration of an example variation of a pump nest assembly 200. The pump nest assembly may include one or more packaging structures in a tub 210 or other suitable container, where each packaging structure may contain a plurality of pumps. The pump nest assembly 200 may, for example, store a plurality of nasal pumps in a protective and/or organized manner that reduces the likelihood of damage or entangling of the pumps. Packaging structures may sit within a tub as shown in FIG. 2A and be accessible through an upper tub opening. In some variations, an opening of the tub 210 may be sealed, such as with a seal 212. The seal 212 may include, for example, a metal foil, plastic film, or any suitable material. The seal 212 may help maintain sterility of the contents of the pump nest assembly 200 until the tub 210 is opened (e.g., by peeling off or otherwise breaching the seal 212), such as to access the packaging structures contained therein. However, in some variations each packaging structure may be a standalone packaging structure that is sealed directly, rather than (or in addition to) being sealed within the tub 210.

Figure 2B:
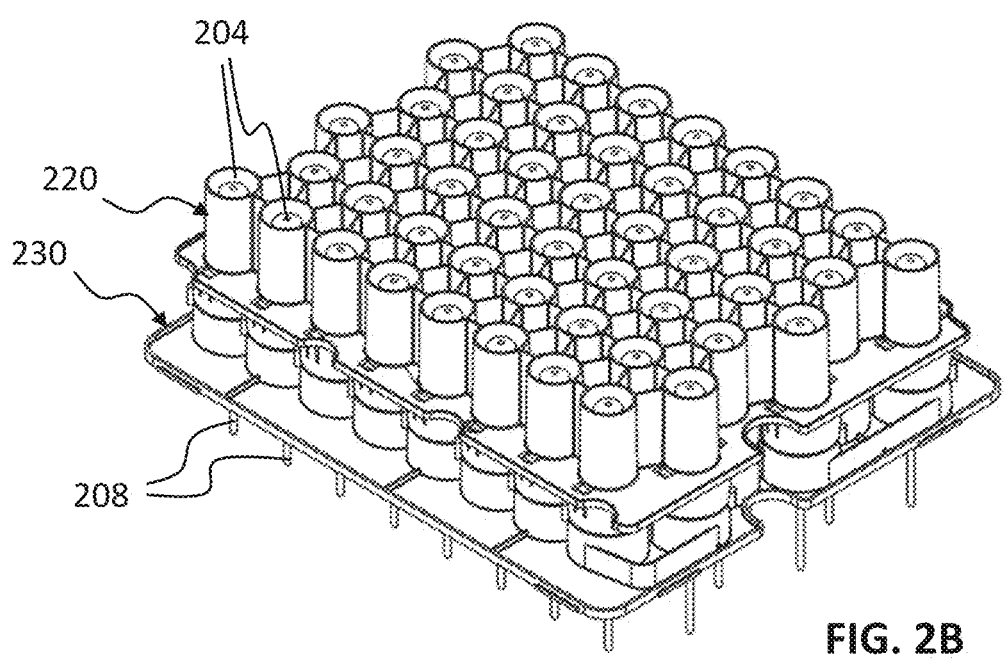
FIGS. 2B and 2C depict assembled and exploded views, respectively, of a portion of an example variation of a pump nest assembly.
Figure 2C:
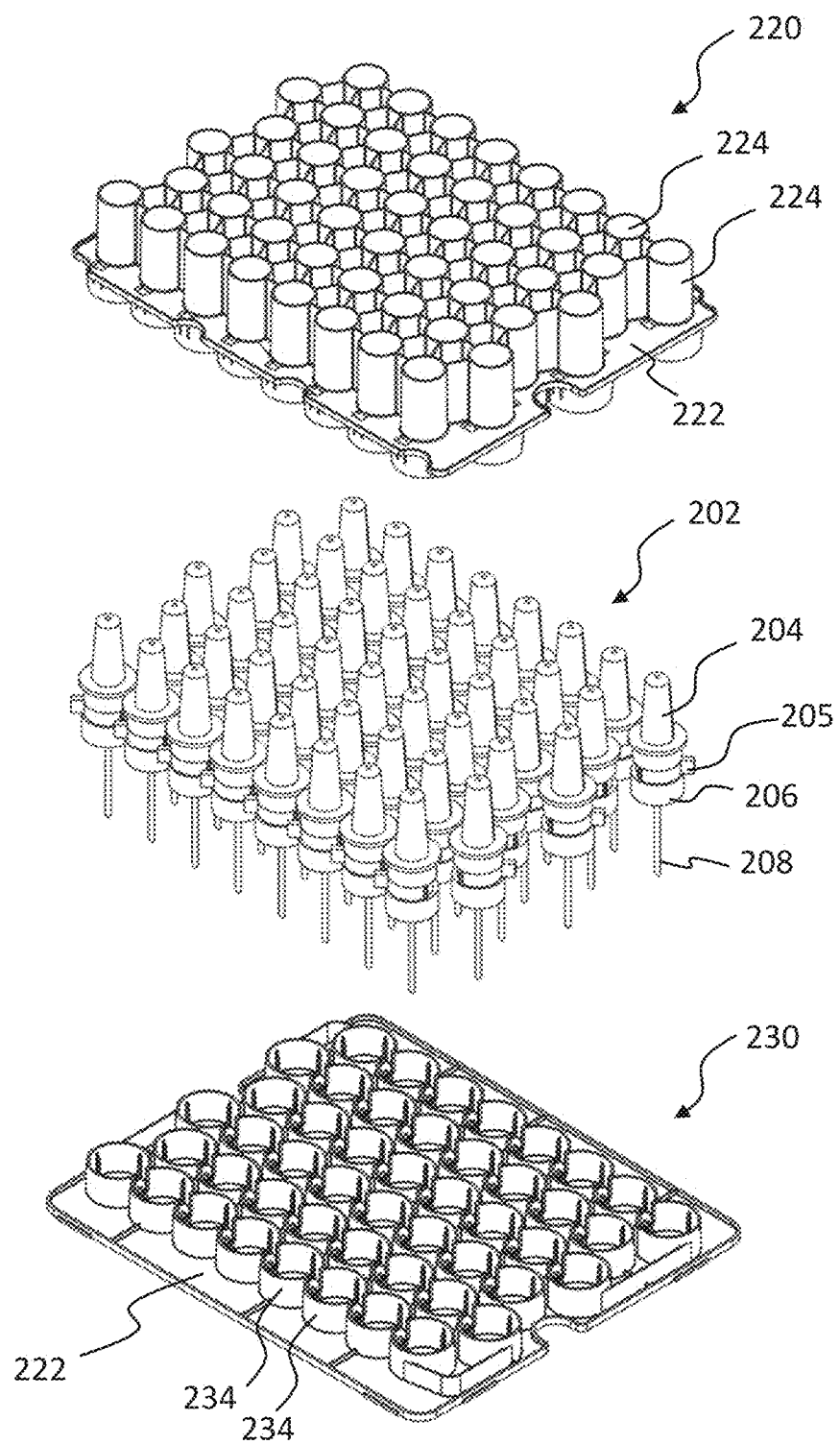

Multiple kinds of packaging structures may collaborate to contain the pumps within the tub 210. For example, as shown in FIG. 2B, the pump nest assembly may include a pump nest 220 and in a pump nest guide 230. As shown in the exploded view of FIG. 2C, the pump nest 220 may include a plurality of dispenser covers 224, each of which may receive an upper portion (e.g., pump head 204) of a respective pump 202. The pump nest guide 230 may include a plurality of dispenser seats 234, each of which may receive a lower portion (e.g., pump cap) of a respective pump 202. The dispenser covers 224 and the dispenser seats 234 may be arranged in similar layouts such that the dispenser covers 224 and the dispenser seats 234 are aligned. Accordingly, the pump nest guide 230, the pumps 202, and the pump nest 220 may be layered so as to organize and protect the pumps 202 between the pump nest guide 230 and the pump nest 220.

The pump nest guide 230 may further function to help protect the dip tubes 208 from damage. For example, the pump nest guide 230 may include a support surface 222 that extends to the internal walls of the tub 210 and is configured to rest upon an internal shoulder of the tub 210. The depth or location of the internal shoulder of the tub may be equal to or exceed the length of the dip tubes that extend beyond a lower surface of the dispenser seats 234, such that when the pump nest guide 230 rests upon the internal shoulder of the tub, the dip tubes are prevented from touching the bottom of the tub 210. Furthermore, due at least in part to the spacing between the dispenser seats 234, the dip tubes 208 may be sufficiently spaced apart from each other so as to avoid interference with adjacent dip tubes. Accordingly, the pump nest guide 230 may help prevent the dip tubes 208 from damage due to bending, entanglement with adjacent dip tubes, etc. The pump nest guide 230 may thus help keep the dip tubes 208 sufficiently straight (e.g., each dip tube axially aligned with the rest of the pump body), which may, for example, help facilitate the attachment of the pumps 202 to containers, as described in further detail below.

Pump Nest Guide

Figure 3A:
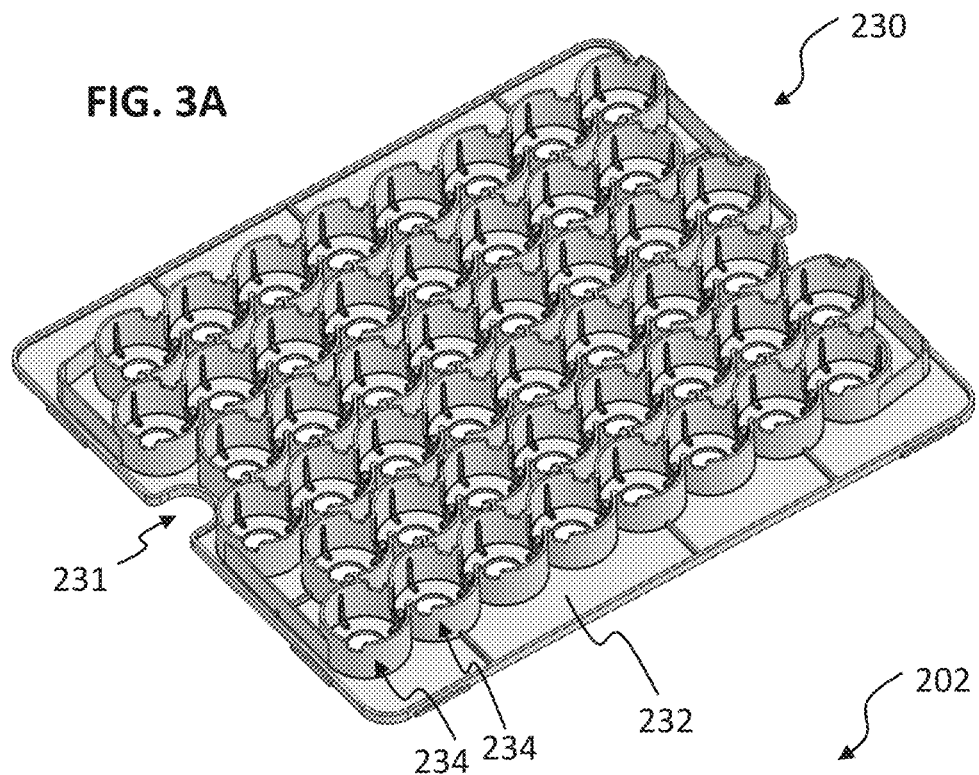
FIG. 3A depicts a schematic illustration of an example variation of a pump nest guide.

As described above, the pump nest guide 230 may receive a plurality of pumps in the pump nest assembly 200. As shown in FIG. 3A, the pump nest guide 230 may include a support surface 232 and a plurality of dispenser seats 234 arranged on the support surface. The support surface 232 may be configured to rest within a tub or other container, as described above. While the support surface 232 is shown in FIG. 3A as generally planar and having a rectangular shape, it should be understood that the support surface 232 may be non-planar (e.g., convex, concave) and have any suitable shape (e.g., circular, elliptical, etc.). In some variations, the pump nest guide 230 may include one or more cutouts 231 that may, for example, provide clearance for fingers between the tub wall and the support surface 232 to enable manual removal of the pump nest guide 230 from the tub. Additionally or alternatively, in some variations the pump nest guide 230 may include other suitable engagement features on the support surface 232 (e.g., around the perimeter of the support surface) or other portion of the pump nest guide 230. For example, the pump nest guide 230 may include a suction cup, a smooth surface to which a suction cup or vacuum source may attach, other fasteners such as hooks, etc. to help facilitate handling of the pump nest guide 230.

The dispenser seats 234 may be arranged on the support surface in an array. For example, the dispenser seats 234 may be arranged in a regular array (e.g., hexagonal, rectangular, etc.), and in some variations may be in a compact array so as to optimize the number of dispenser seats 234 (and accordingly, the number of pumps) that may be placed into the pump nest guide 230. Alternatively, the dispenser seats 234 may be arranged in an irregular array or any suitable layout pattern. While the variation shown in FIG. 3A includes 48 dispenser seats, it should be understood that the pump nest guide 230 may include any suitable number of dispenser seats 234.

Figure 3B:
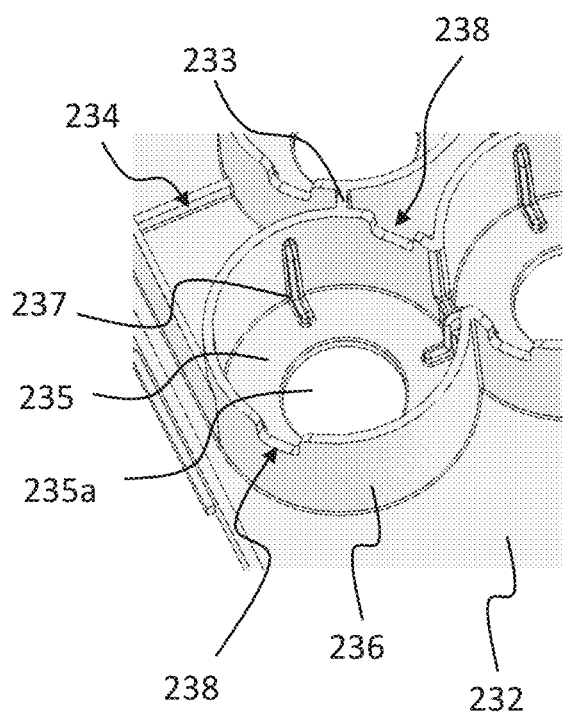
FIG. 3B depicts a detailed view of a dispenser seat in an example variation of a pump nest guide.

In some variations, adjacent dispenser seats 234 may be coupled. This may, for example, help increase rigidity of the pump nest guide and help stabilize the pumps 202 when the pumps 202 are placed in the pump nest guide. For example, as shown in FIG. 3B, the pump nest guide may include one or more interconnecting walls 233 that extend between adjacent dispenser seats 234. The interconnecting walls 233 may be integrally formed with the support surface 232 and/or dispenser seats 234, or may be separately formed and coupled to the support surface 232 and/or dispenser seats 234. Additionally or alternatively, adjacent dispenser seats 234 may share a common structure (e.g., share a common wall 236 as described below).

Figure 3C:
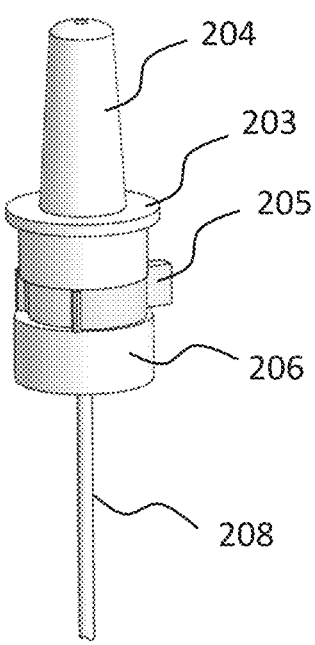
FIG. 3C depicts a schematic illustration of an example variation of a pump in a pump nest assembly.
Figure 3D:
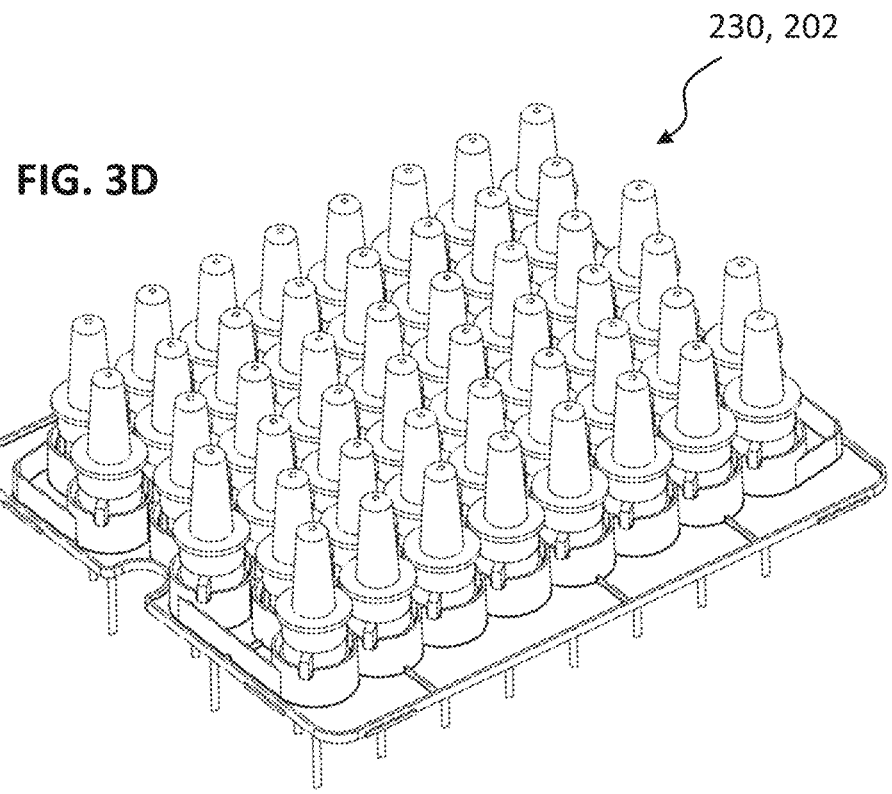
FIGS. 3D and 3E depict perspective and detailed views, respectively, of pumps arranged in an example variation of a pump nest guide.

As shown in FIG. 3B, a dispenser seat 234 may include a base 235 having an opening 235a, and a wall 236 extending from the base 235 to form a recess for receiving a pump dispenser. In other words, in some variations the pump dispenser may be configured to sit upon the base 235, and at least partially contained within the wall 236. The base 235 may be sized and shaped in a similar manner as a bottom portion of the pump dispenser (e.g., cap 206, as shown in FIG. 3C). As shown in FIG. 3B, the base 235 may include an opening 235a, which may function to permit passage of a dip tube 208 of the pump 202 to extend through the pump nest guide. The opening 235a may be circular or any suitable shape.

The wall 236 of the dispenser seat 234 may be configured to substantially circumscribe the bottom portion of the pump dispenser. For example, as shown in FIG. 3B, the base 235 and the wall 236 may be generally circular to accommodate a circular pump dispenser, though they may be any suitable shape to accommodate any suitable footprint of a pump dispenser (e.g., elliptical, square, rectangular, etc.). The wall 236 may, in some variations, extend orthogonally from the base 235, though in some variations the wall 236 may be sloped. For example, in some variations, the diameter of the wall 236 may be narrower where the wall attaches to the base, which may funnel or self-center the pump dispenser when the pump dispenser is placed into the pump nest guide. Additionally or alternatively, thickness of the wall 236 may vary, such that an inner diameter of the wall 236 provides a tapering or self-centering surface for the pump dispenser while the outer diameter of the wall 236 is constant.

In some variations, the wall 236 includes a continuous structure around part or all of the perimeter of the dispenser seat. Alternatively, in some variations the wall 236 may include multiple discrete wall segments that follow the shape of the base and extend to collectively contain the bottom of the pump dispenser. Additionally or alternatively, the dispenser seat 234 may include one or more brackets 237 coupled to or formed with the base 235 and the wall 236, where each bracket 237 may function as structural reinforcement for the shape of the dispenser seat 234 and/or as a release point for injection molding, etc.

Although a dispenser seat 234 is primarily described above to include a wall that is configured to contain a pump 202 by surrounding an outer surface of the pump 202, a dispenser seat 234 may include any suitable features for locating a pump 202 in the dispenser seat 234 in the pump nest guide 230. For example, in some variations, a dispenser seat in the pump nest guide may additionally or alternatively include one or more extending projections that interfaces with an internal surface of the pump dispenser (e.g., inner surface of the cap 206). For example, a dispenser seat may include an upwardly projecting ring or multiple discrete ring segments around which the pump dispenser 202 sits.

Figure 3E:
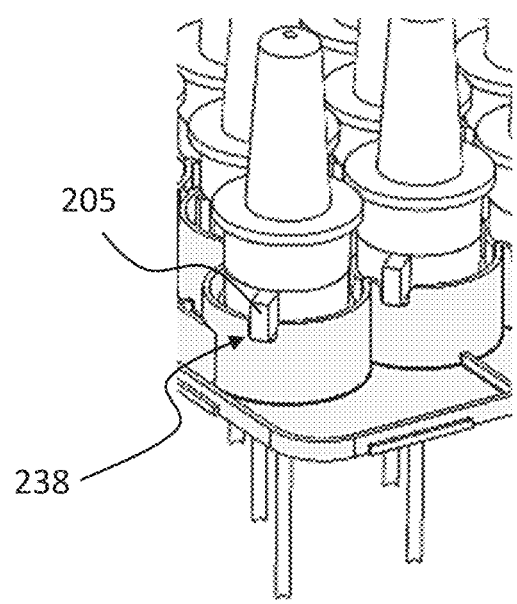

Furthermore, as shown in FIG. 3B, the dispenser seat 234 may include at least one alignment feature 238 configured to engage with an engagement feature in a pump to thereby orient the pump in the at least one dispenser seat. For example, the exemplary pump shown in FIG. 3C includes an engagement feature 205 that extends radially outward from the body of the pump 202, and the alignment feature 238 in the dispenser seat 234 may include a slot or other cutout that receives the engagement feature 205, thereby orienting the pump 202 in a predetermined rotational orientation in the dispenser seat 234 as shown in FIG. 3E. In some variations, a dispenser seat 234 may include multiple alignment features to accommodate multiple permissible pump orientations. For example, as shown in FIG. 3B, a dispenser seat 234 may include two alignment features 238 that are opposite one another across the dispenser seat 234 (180 degrees rotationally offset), which may enable a pump 202 to have two permissible rotational orientations within the dispenser seat 234.

The alignment features 238 for the multiple dispenser seats 234 in the pump nest guide 230 may be oriented in a parallel manner, such that when multiple pumps 202 are seated in the pump nest guide 230, all of the pumps 202 may be neatly and compactly organized without physical interference among the pumps. Additionally, the engagement of the alignment features 238 and the engagement features 205 may help rotationally stabilize the pumps 202 during transport, thereby reducing pump movement in the pump nest guide to reduce risk of damage and/or help ensure predictable positioning for the pumps across the entire array to help facilitate other automated processes such as labeling, etc.

In this example for sake of illustration, the engagement feature 205 includes a radial tab on a clip that couples to the pump 202 to prevent inadvertent actuation of the pump. Specifically, the safety clip may be inserted between an actuating pump head 204 and the pump cap 206, to physically block movement of the pump head 204 toward the pump cap 206 (e.g., during transport of the pump 202). Actuation of the pump 202 is permitted after removing the clip. However, while in this example a radial tab on the clip includes the engagement feature 205 for assisting orientation of the pump in the pump nest guide, the engagement feature 205 may be on any suitable feature of the pump 202 (e.g., a longitudinal rib on the cap 206) and/or an accessory thereon (e.g., circular ring placed over the cap 206).

In some variations, the pump nest guide may be injection molded out of a suitably rigid plastic, though the pump nest guide may be formed in any suitable manner (e.g., 3D printed, milled, etc.). In some variations, the pump nest guide may include a material stable under gamma ray sterilization (e.g., HDPE) and/or any suitable kind of sterilization such as X-ray sterilization, E-Beam sterilization, ethylene oxide sterilization, steam, etc. Furthermore, some or all of the dispenser seats 234 may be integrally formed with the support surface 232. Additionally or alternatively, some or all of the dispenser seats 234 may be separately formed from the support surface 232 and be coupled to the support surface 232 through a mechanical interfit (e.g., threads, snap fit, other mating features, etc.), suitable fasteners (e.g., epoxy, connectors, etc.), and/or suitable joining process (e.g., thermal welding).

An example variation of a pump nest guide (with 48 dispenser seats) is shown in greater detail in FIGS. 13A-13E. Additionally, an example variation of a pump nest guide (with 24 dispenser seats) is shown in FIGS. 14A-14E.

Pump Nest

Figure 4A:
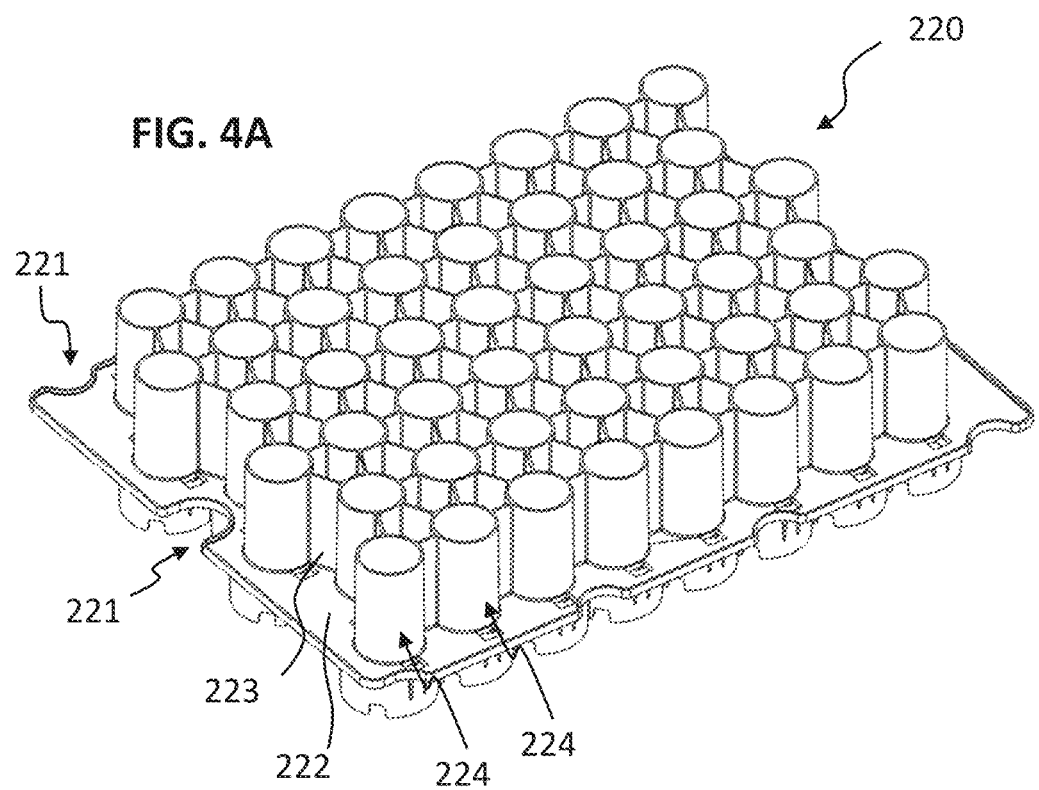
FIG. 4A depicts a schematic illustration of an example variation of a pump nest.

The pump nest guide 220 may cover and/or engage with a plurality of pumps seated in the pump nest guide 230. As shown in FIG. 4A, the pump nest 220 may include a support surface 222 and a plurality of dispenser covers 224 arranged on the support surface. While the support surface 222 is shown in FIG. 4A as generally planar and having a rectangular shape, it should be understood that the support surface 222 may be non-planar (e.g., convex, concave) and have any suitable shape (e.g., circular, elliptical, etc.). Like the pump nest guide 232, the pump nest 220 may include one or more cutouts 221 that may, for example, provide clearance for fingers to enable manual removal of the pump nest 220 from the tub. Additionally or alternatively, in some variations the pump nest 220 may include other suitable engagement features on the support surface 222 (e.g., around the perimeter of the support surface) or other portion of the pump nest 220. For example, the pump nest 220 may include a suction cup, a smooth surface to which a suction cup or vacuum source may attach, other fasteners such as hooks, etc. to help facilitate handling of the pump nest 220.

The dispenser covers 224 may be arranged on the support surface 222 in an array similar to that described above for the dispenser seats 234 in the pump nest guide 230. For example, the dispenser covers 224 may be arranged in a regular array (e.g., hexagonal, rectangular, etc.), irregular array, or any suitable layout pattern. While the variation shown in FIG. 4A includes 48 dispenser covers, it should be understood that the pump nest 220 may include any suitable number of dispenser covers. The layout arrangement of the dispenser covers 224 in the pump nest may be identical to the layout arrangement of the dispenser seats 234 in the pump nest guide, so as to simultaneously accommodate the same set of pumps between the pump nest guide and the pump nest.

In some variations, adjacent dispenser covers 224 may be coupled. This may, for example, help increase rigidity of the pump nest and help stabilize the pumps 202 when they are in the pump nest 220. For example, as shown in FIG. 4A, the pump nest 220 may include one or more interconnecting walls 223 that extend between adjacent dispenser covers 224. The interconnecting walls 223 may be integrally formed with the support surface 222 and/or dispenser covers 224, or may be separately formed and coupled to the support surface 222 and/or dispenser covers 224. Additionally or alternatively, adjacent dispenser covers may share a common structure such as a wall.

Figure 4B:
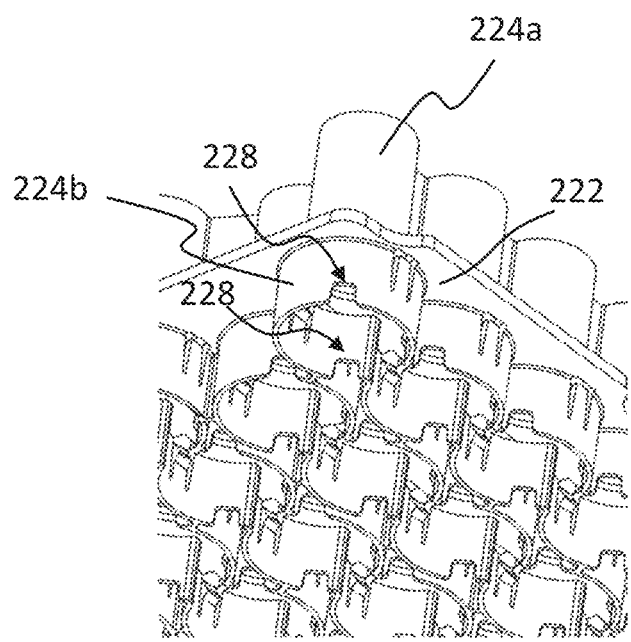
FIGS. 4B and 4C depict detailed views of a dispenser cover in an example variation of a pump nest, without and with a pump, respectively.
Figure 4C:
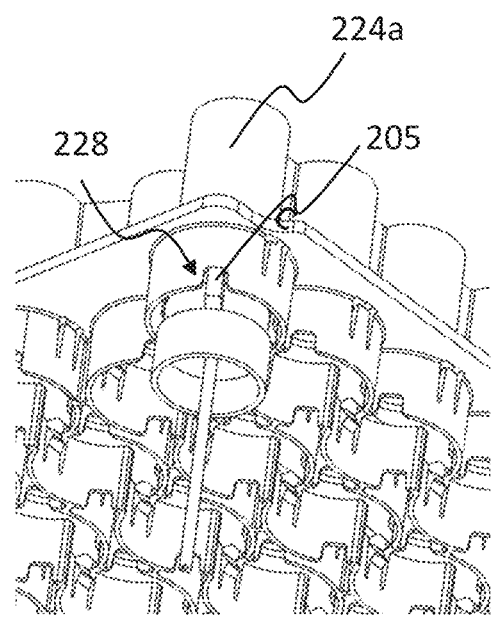

As shown in FIG. 4B, in some variations a dispenser cover 224 may include a first dispenser cover portion 224a (e.g. upper portion) on one side of the support surface 222, and a second dispenser cover portion 224b (e.g., lower portion) on an opposite side of the support surface 222. The dispenser cover portion 224a may, for example, include a wall that is configured to substantially surround a pump head 204 of a pump that extends beyond the support surface 222. The inner diameter of the dispenser cover portion 224a may be larger than a diameter of the pump head 204, but smaller than a diameter of a pump shoulder 203 (shown in FIG. 3C), such that when the pump nest 220 is placed over an array of pumps 202, the pump nest 220 rests upon the collective pump shoulders 203 of the pumps 202. The length of the dispenser cover portion 224a accordingly may, in some variations, be at least as long as (or longer than) the pump head 204 of the pump, so as to adequately extend along the length of the pump head 204. In some variations, some or all the dispenser cover portions 224a may have an open distal end as shown in FIG. 5A, though in some variations some or all the dispenser cover portion 224a may have a closed distal end to completely cover the pump heads 204.

The second dispenser cover portion 224b may similarly include a wall that is configured to substantially surround a cap 206 of a pump. As shown in FIG. 3C, in some variations a pump 202 may include a cap 206 having a wider diameter than the pump head 204. Accordingly, to accommodate such a pump, a dispenser cover 224 may include a dispenser cover portion 224b that has a wider diameter than the dispenser cover portion 224a.

In some variations, the dispenser cover portion 224b may be a similar, but inverted version, of the dispenser seat 234 described above. For example, the dispenser cover portion 224b may include an opening to permit passage of the pump head 204 through the support surface 222 (so as to be covered by the dispenser portion 224a). Additionally, dispenser cover portion 224a may include at least one alignment feature 238 configured to engage with an engagement feature in a pump, to thereby orient the pump in the pump nest 220. Similar to that described above, the alignment feature 238 may include a slot or other cutout that receives the engagement feature 205 (e.g., radial projection on the pump 202). Furthermore, in some variations the dispenser cover portion 224b may include multiple alignment features (e.g., two alignment features 180 degrees rotationally offset from each other around the dispenser cover portion 224b).

Figure 5A:
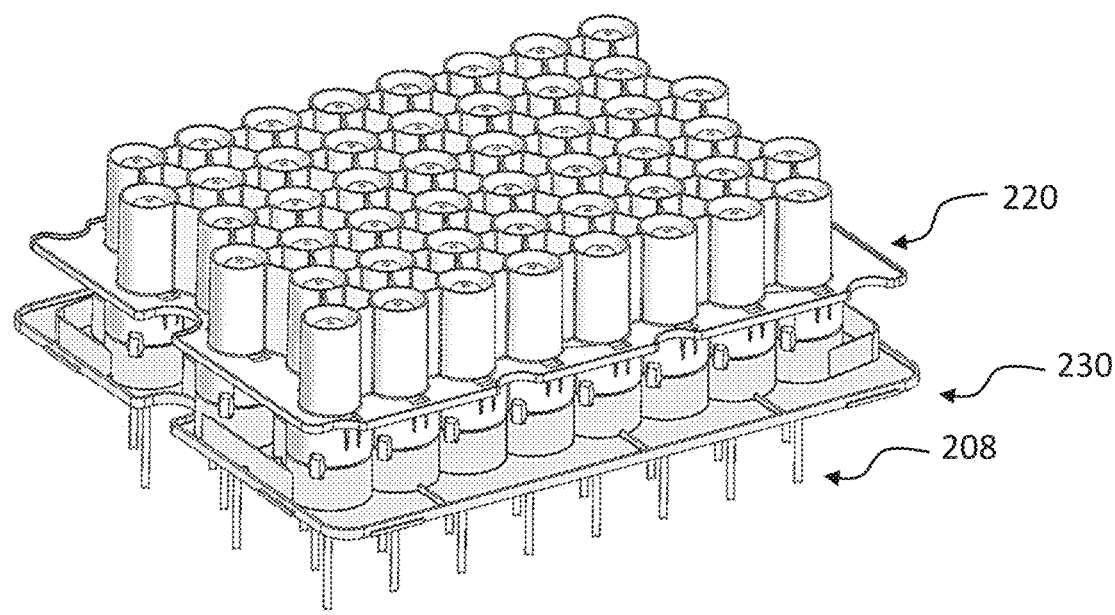
FIG. 5A depicts a schematic illustration of a portion of an example variation of a pump nest assembly including a pump nest guide, pumps, and a pump nest.
Figure 5B:
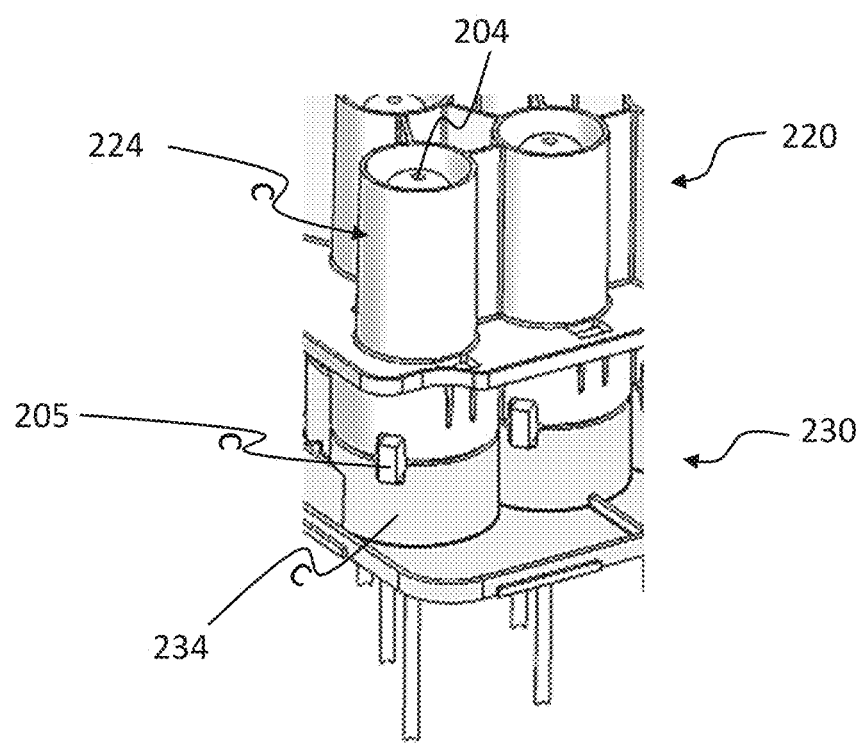
FIG. 5B depicts a detailed view of the portion of the pump nest assembly depicted in FIG. 5A.

Accordingly, as shown in FIGS. 5A and 5B, a set of pumps may be nested within both the pump nest 220 and the pump nest guide 230, with dip tubes 208 extending beyond the pump nest guide 230. Each pump may be nested between a respective dispenser seat 234 and dispenser cover 224 that are axially aligned. As shown in FIG. 5B, an engagement feature 205 of the pump may engage both the alignment feature 238 in the dispenser seat 234 and the alignment feature 228 in the dispenser cover 224. However, in some variations one or both of the alignment features 228 and 238 may be omitted. For example, such alignment features may not be necessary if the pump 202 does not include an engagement feature 205, or otherwise if there is less concern for keeping the pumps 202 in a predetermined rotational orientation within the pump nest 220 and the pump nest guide 230.

Figure 6A:
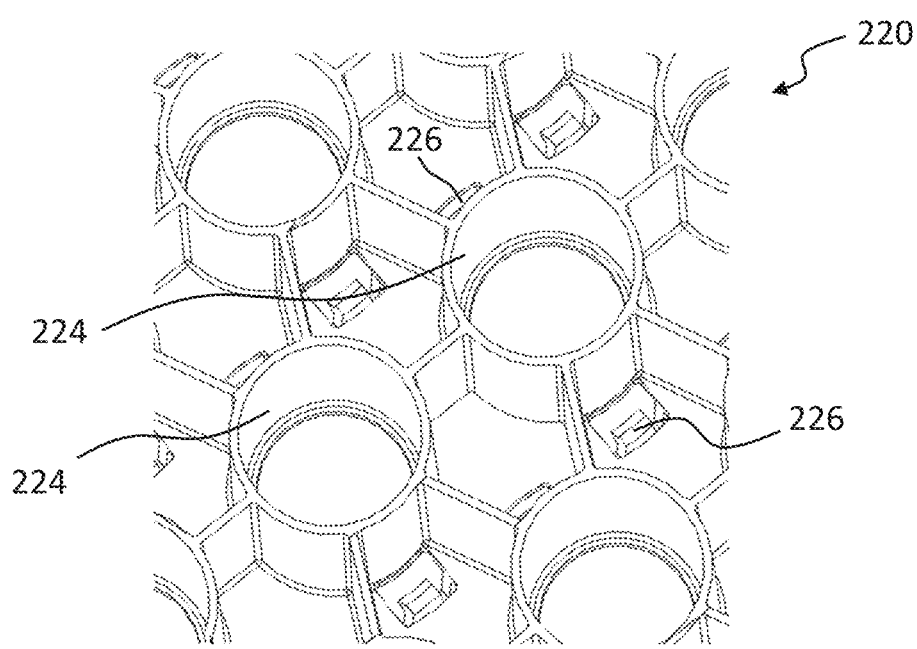
FIG. 6A depicts a detailed view of an example variation of a pump nest with locking members.

Furthermore, in some variations, a dispenser cover may include one or more locking members configured to couple a pump 202 to the dispenser cover. For example, as shown in FIG. 6A, a dispenser cover may include at least one locking flexure member 226 configured to couple a pump to the dispenser cover 224. In some variations, a dispenser cover may include multiple locking members (e.g., two locking flexure members 226). The locking members may be distributed equally or radially symmetrically around the dispenser cover, so as to retain the pump in the dispenser cover in a balanced manner. For example, as shown in FIG. 6A, a dispenser cover may include two locking flexure members 226 arranged 180 degrees rotationally offset from each other. In some variations, the locking member(s) may engage with a radial projection of the pump 202 to couple the pump 202 to the dispenser cover 224. When the locking members across the pump nest 220 couple a set of multiple pumps 202 to the pump nest 220, all secured pumps 202 may advantageously be manipulated (e.g., transported) by handling the pump nest 220 itself, as further described below. Accordingly, the pump nest with such locking members may enable easy, efficient handling of multiple pumps simultaneously.

FIGS. 6B and 6C illustrate an example variation of a locking flexure member 226 coupling to a pump 202. The locking flexure members 226 may be formed from or coupled to the dispenser cover portion 224b on a lower side of the pump nest 220, though in other variations similar structures may be located in the upper dispenser cover portion 224a or another part of the pump nest 220. As shown in FIG. 6B, a locking flexure member 226 may include an arm with a fixed proximal end and a free distal end with a stop 227. The locking flexure member may generally extend longitudinally along the dispenser cover portion 224b, parallel to a central axis of the dispenser cover, and may be configured to flex in a radial direction (e.g., relative to the central axis of the dispenser cover). For example, the locking flexure member 226 may flex radially outward to receive the pump 202 within the dispenser cover 224. The stop 227 may include a lower sloped surface to further ease passage of the pump 202 into the dispenser cover 224. When the pump 202 reaches a certain insertion depth into the dispenser cover 224, the pump shoulder 203 may pass beyond the stop 227, which permits the locking flexure member to return inwards to its previous radial position. As shown in FIG. 6C, the stop 227 may abut the pump shoulder 203 and urge the pump shoulder 204 against the support surface (or lower edge of the dispenser cover portion 224a), to thereby secure the pump 202 against the dispenser cover. In some variations, the stop 227 may also include an upper sloped surface that facilitates easier removal of the pump 202 from the dispenser cover with application of sufficient removal or separation force.

In some variations, the locking flexure member 226 may include a bias (e.g., inherent in the form or material of the flexure member) that urges the locking flexure member 226 radially inward, to thereby further secure the pump 202 within the dispenser cover. Additionally or alternatively, other locking features may help couple the pump to the dispenser cover. For example, the dispenser cover may include frictional features (e.g., ribs or other textural features, rubberized or other high-friction materials, etc.) located on an internal surface of the dispenser cover to engage the pump 202 within the dispenser cover.

In some variations, like the pump nest guide, the pump nest may be injection molded out of a suitably rigid plastic, though the pump nest may be formed in any suitable manner (e.g., 3D printed, milled, etc.). In some variations, the pump nest may include a material stable under gamma ray sterilization (e.g., HDPE). Furthermore, some or all of the dispenser covers may be integrally formed with the support surface. Additionally or alternatively, some or all of the dispenser covers may be separately formed from the support surface and be coupled to the support surface through a mechanical interfit (e.g., threads, snap fit, other mating features, etc.), suitable fasteners (e.g., epoxy, connectors, etc.), and/or suitable joining process (e.g., thermal welding).

An example variation of a pump nest (with 48 dispenser covers) is shown in greater detail in FIGS. 15A-15G. Additionally, an example variation of a pump nest guide (with 24 dispenser covers) is shown in FIGS. 16A-16G.

Thus, a set of multiple pumps may be packaged in a protective, orderly manner in a pump nest assembly as described above. For example, pumps may be nested between a pump nest guide and a pump nest such as those described above. This subassembly may be placed into a tub or other container, and may be sealed to contain the pump nest guide, pumps, and pump nest contained therein. To remove the pumps, (e.g., for assembling with containers, as described below) the tub seal (if present) may be removed, and the pump nest may be lifted out of the tub (or slid out, etc.). Since the pumps may be coupled to the pump nest via locking members or other locking features, removal of the pump nest may simultaneously result in collective or simultaneous removal of the pumps. The pump nest guide may remain in the tub when the pump nest and pumps are removed from the tub. Further details of methods for assembling nested components are described below.

Container Nest Assembly

Figure 7A:
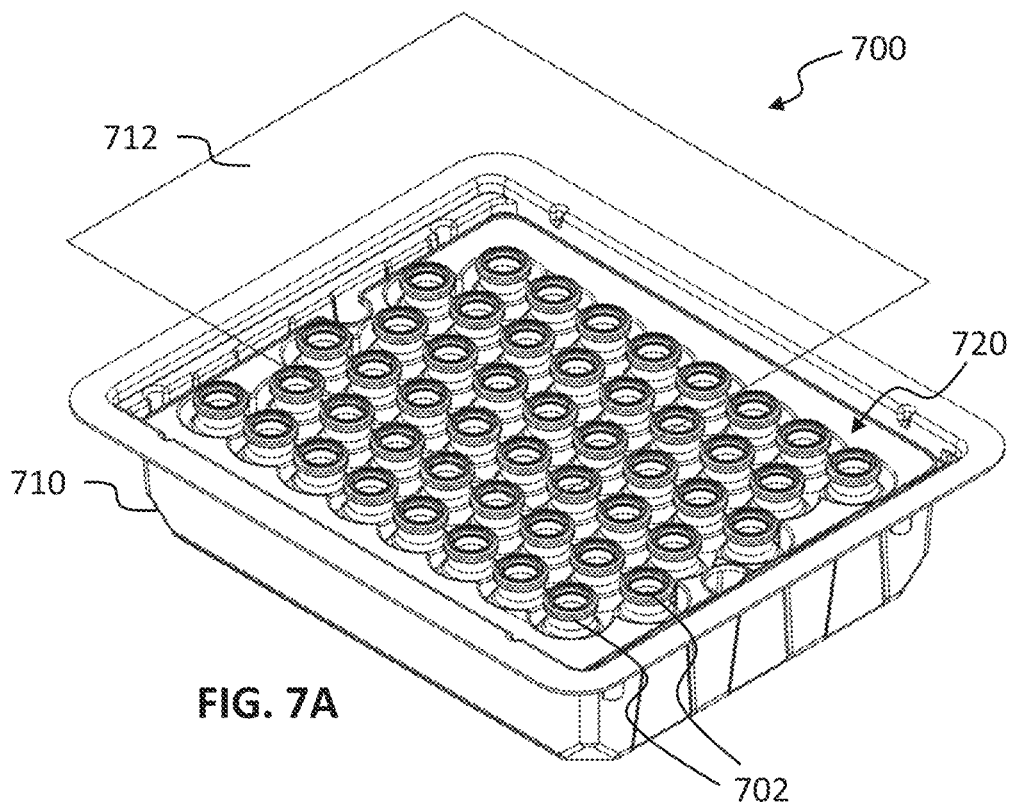
FIG. 7A depicts a schematic illustration of an example variation of a container nest assembly.

FIG. 7A depicts a schematic illustration of an example variation of a container nest assembly 700. The container nest assembly may include one or more packaging structures in a tub 710 or other suitable container, where each packaging structure may contain a plurality of containers (e.g., bottles). The container nest assembly may, for example, store a plurality of bottles (e.g., glass or plastic bottles) in a protective and/or organized manner that reduces the likelihood of damage to the bottles. Packaging structures may sit within the tub 710 as shown in FIG. 7A, and may be accessible through an upper tub opening. In some variations, an opening of the tub 710 may be sealed, such as with a seal 712. The seal 712 may include, for example, a metal foil, plastic film, or any suitable material. The seal 712 may help maintain sterility of the contents of the container nest assembly 700 until the tub 710 is opened (e.g., by peeling off or otherwise breaching the seal 712), such as to access the packaging structures contained therein.

Figure 7B:
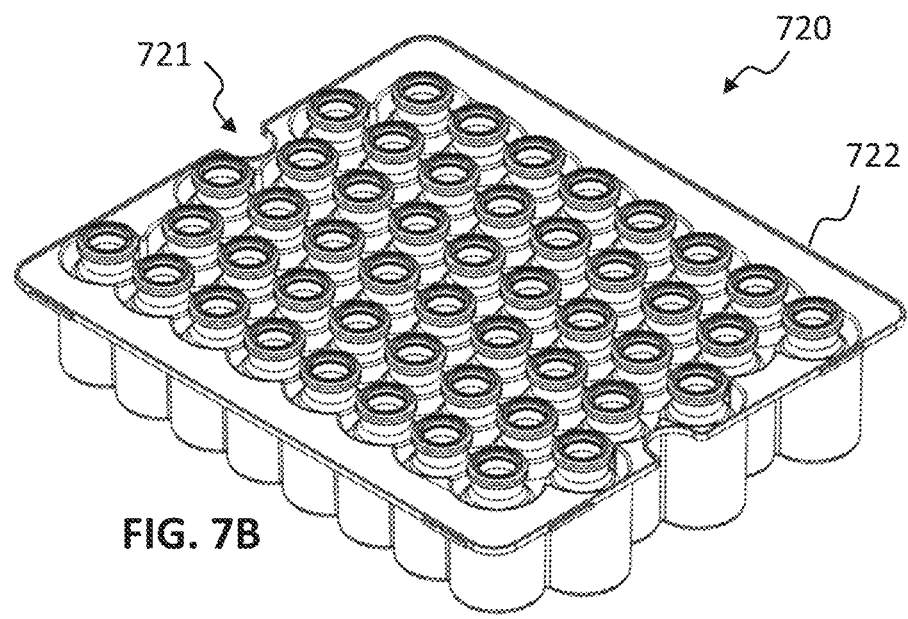
FIG. 7B depicts a schematic illustration of a portion of an example variation of a container nest assembly including a container nest and containers.
Figure 7C:
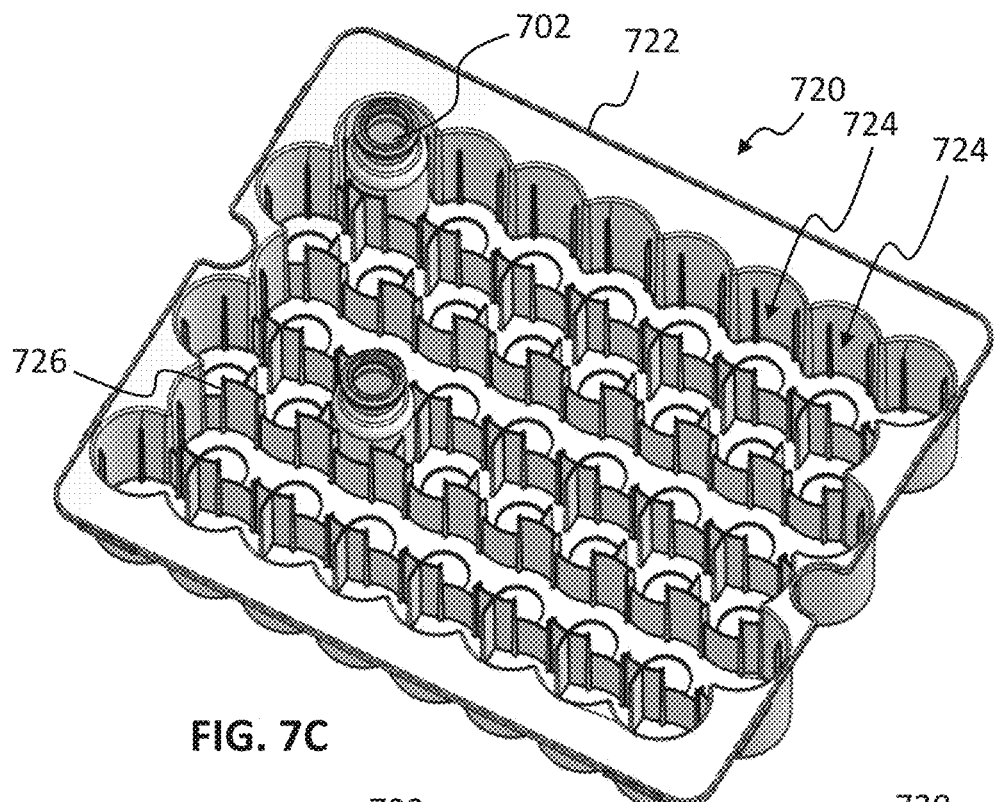
FIGS. 7C and 7D are perspective and plan views, respectively, of an example variation of a container nest.
Figure 7D:
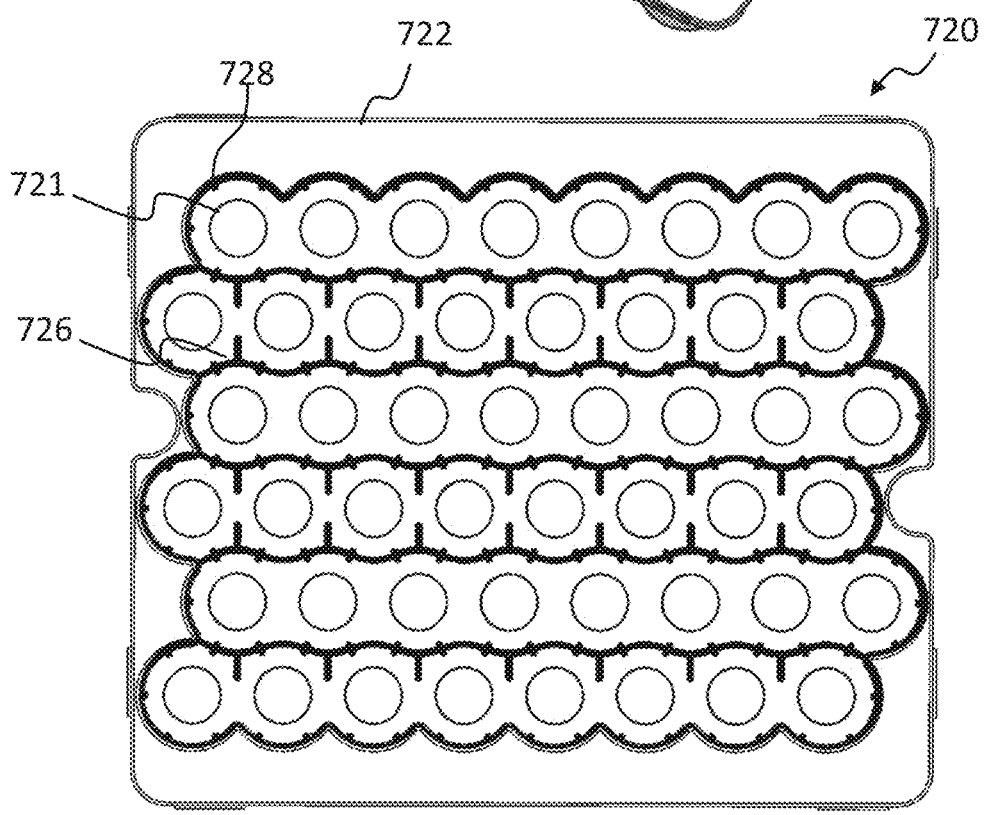

As shown in FIGS. 7B-7D, the packaging structures in the container nest assembly may include one or more container nests 720. A container nest 720 may include a support surface 722 and a plurality of container seats 724 arranged on the support surface. The support surface 722 may be configured to rest within a tub or other container. However, in some variations the container nest 720 may be a stand-alone packaging structure that is sealed directly, rather than (or in addition to) being sealed within a tub 710. While the container nest 720 is shown in FIG. 7B as generally rectangular, it should be understood that the container nest 720 may have any suitable overall shape (e.g., circular, elliptical). Furthermore, similar to the pump nest 220 and pump nest guide 230 described above, the container nest 720 may include one or more cutouts 721 that may, for example, provide clearance for fingers between the tub wall and the support surface 722 to enable manual removal of the container nest 720 from the tub. Additionally or alternatively, in some variations the container nest 720 may include other suitable engagement features on the support surface 722 (e.g., around the perimeter of the support surface) or other portion of the container nest 720. For example, the container nest 720 may include a suction cup, a smooth surface to which a suction cup or vacuum source may attach, other fasteners such as hooks, etc. to help facilitate handling of the container nest 720.

The container seats 724 may be arranged on the support surface 722 in an array similar to that described above for the dispenser seats 234 in the pump nest guide 230. For example, the container seats 724 may be arranged in a regular array (e.g., hexagonal, rectangular, etc.), irregular array, or any suitable layout pattern. While the variation shown in FIG. 7B includes 48 container seats, it should be understood that the container nest 720 may include any suitable number of container seats. If the containers to be placed in the container nest 700 are intended to be assembled with pumps in the pump nest assembly described above, then the layout arrangement of the container seats 724 in the container nest may be identical to the layout arrangement of the pumps (and dispenser covers and dispenser seats) in the pump nest assembly, such that alignment of the container nest with the pump nest results in collective alignment of the containers with corresponding pumps.

In some variations, as shown in FIGS. 7C and 7D, a container seat 724 may be defined by one or more walls. The walls may form a recess with a base. In some variations, the recess may be arranged below the support surface 722, though the recess may additionally or alternatively be above the support surface 722. For example, a first portion of the container seat 724 may be arranged on a first side (e.g., upper side) of the support surface, while a second portion may be arranged on a second side (e.g., lower side) of the support surface, such that when a container 702 is in the container seat 724, part of the container may lie above the support surface and part of the container may lie below the support surface. In the variation shown in FIGS. 7C and 7D, one or more walls may function as partitions to define discrete container seats, where each container seat is configured to receive a respective container.

The walls may be curved, linear, or any suitable shape to accommodate the containers. In some variations, as shown in FIG. 7D, the walls 726 may be contoured to generally follow the curvature of the containers 702, which may, for example, encourage close packing of the containers for efficient use of space in the container nest. The walls 726 may include segments of varying heights. In some variations, the walls 726 may include continuous structures that extend from one side of the array of container seats to an opposite side of the array of container seats, though in some variations at least some walls 726 may include discrete segments. For example, in some variations only a portion of a perimeter of a container seat may be surrounded by walls, while in some variations the entire perimeter of the container seat may be surrounded by walls.

Furthermore, in some variations, at least some of the container seats 724 may include one or more spacers 728. The spacers 728 may function to create sufficient distance between adjacent containers to help prevent contact between the adjacent containers when the container nest 720 is jostled or otherwise in movement. The spacers 728 may, for example, project radially inward toward the middle of the container seat 724, and may be arranged in equal or unequal distribution around the perimeter of the container seat 724. In some variations, the spacers 728 may include longitudinal ridges on the one or more walls 726, and extend radially inward a sufficient distance so as to allow a container to self-center into the container seat. In some variations, a container seat 724 may include additional cushioning material (e.g., foam, cloth) that may absorb impact to further protect the container from damage.

Additionally or alternatively, the container nest 720 may include one or more openings. As shown in FIG. 7D, in some variations, a container seat 724 may include at least one opening 721 in a base of the container seat 724. The opening 721 may, for example, help equalize air pressure so as to enable easy settling of the container in the container seat 724 and/or easy removal of the container from the container seat 724. The opening 721 may additionally or alternatively reduce weight of the container nest and/or reduce manufacturing cost due to reducing amount of material in the container nest 720. The opening 721 may have any suitable shape. For example, while the opening 721 is shown in FIG. 7D to be circular, in some variations the opening 721 may be in the shape of any polygon, irregular shape, or custom pattern. Furthermore, a container seat 724 may include multiple openings (e.g., two, three, four, five, or more) in the base or other suitable portion of the container seat 724.

In some variations, the container nest may be injection molded out of a suitably rigid plastic, though the container nest may be formed in any suitable manner (e.g., 3D printed, milled, etc.). In some variations, the container nest may include a material stable under gamma ray sterilization (e.g., HDPE). Furthermore, some or all of the container seats may be integrally formed with the support surface. Additionally or alternatively, some or all of the container seats may be separately formed from the support surface and be coupled to the support surface through a mechanical interfit (e.g., threads, snap fit, other mating features, etc.), suitable fasteners (e.g., epoxy, connectors, etc.), and/or suitable joining process (e.g., thermal welding).

An example variation of a container nest (with 48 container seats) is shown in greater detail in FIGS. 17A-17E.

Dropper Nest Assembly

Figure 8A:
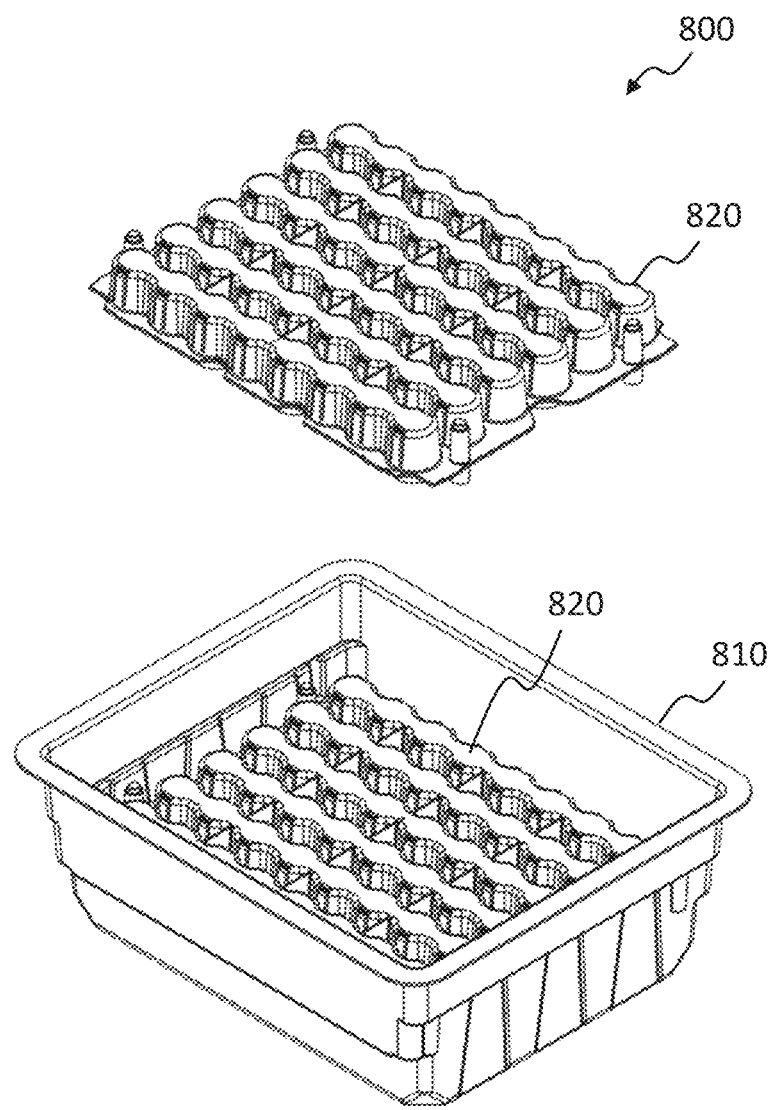
FIG. 8A depicts a schematic illustration of an example variation of a dropper nest assembly.

FIG. 8A depicts a schematic illustration of an example variation of a dropper nest assembly 800. The eyedropper nest assembly may include one or more packaging structures in a tub 810 or other suitable container, where each packaging structure may include a plurality of dispensers (e.g., drop dispensers, such as eyedroppers). The dropper nest assembly 820 may, for example, store a plurality of drop dispensers in a protective and/or organized manner that reduces the likelihood of damage to the dropper dispensers. Packaging structures may sit within the tub 810 as shown in FIG. 8A, and may be accessible through an upper tub opening. In some variations, an opening of the tub 810 may be sealed, such as with a seal similar to that described above for the pump nest assembly and container nest assembly. The seal may help maintain sterility of the contents of the dropper nest assembly 800 until the tub 810 is opened.

As shown in FIG. 8A, the packaging structures in the dropper nest assembly may include one or more dropper nests 820. A single dropper nest 820 may be contained in the tub 810, or multiple dropper nests 820 may be layered or stacked in a single tub 810. However, in some variations the dropper nest 820 may be a standalone packaging structure that is sealed directly, rather than (or in addition to) being sealed within a tub 810.

Figure 8B:
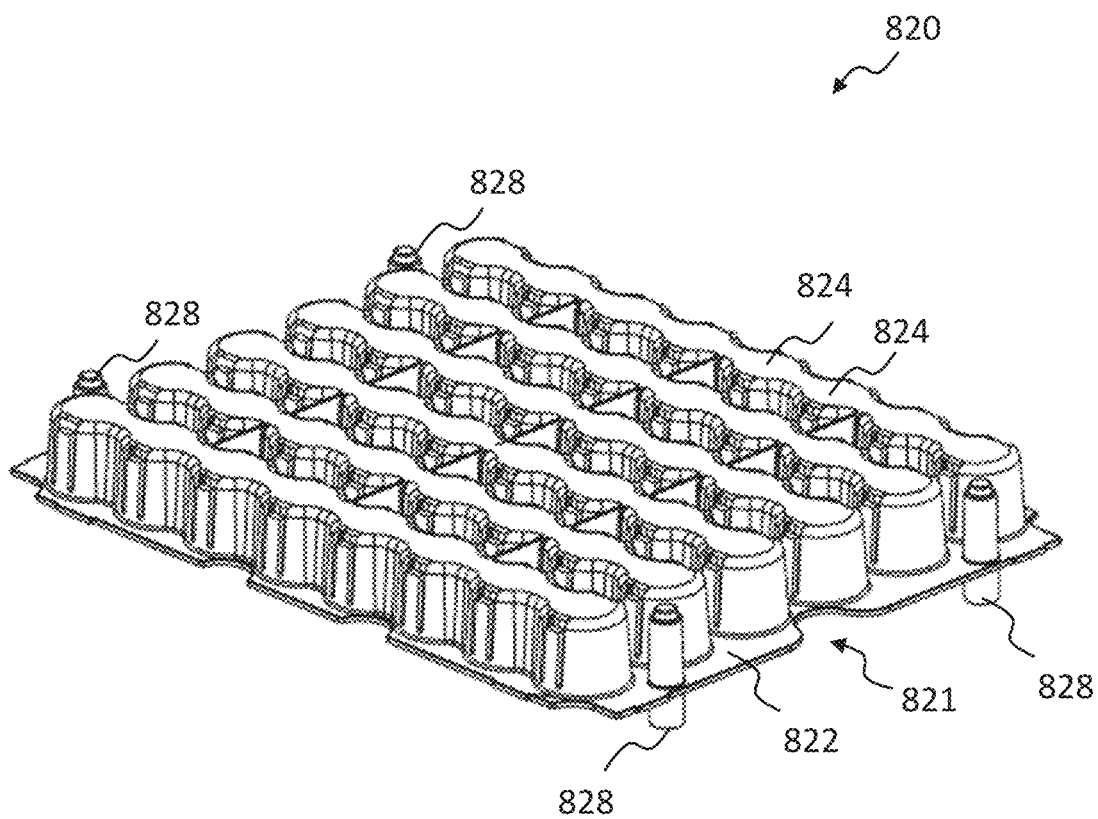
FIG. 8B depicts a schematic illustration of an example variation of a dropper nest.

As shown in FIG. 8B, a dropper nest 820 may include a support surface 822 and a plurality of dispenser covers 824 arranged on the support surface 822. Each of the dispenser covers 824 may be configured to receive and/or engage with a respective drop dispenser (e.g., eyedropper). Like the packaging structures described above, while the dropper nest 820 is shown in FIG. 8B as generally rectangular, it should be understood that the dropper nest 820 may have any suitable overall shape (e.g., circular, elliptical). Furthermore, the dropper nest 820 may include one or more cutouts 821 that may, for example, provide clearance for fingers between the tub wall and the support surface 822 to enable manual removal of the dropper nest 820 from the tub. Additionally or alternatively, in some variations the dropper nest 820 may include other suitable engagement features on the support surface 822 (e.g., around the perimeter of the support surface) or other portion of the dropper nest 820. For example, the dropper nest 820 may include a suction cup, a smooth surface to which a suction cup or vacuum source may attach, other fasteners such as hooks, etc. to help facilitate handling of the dropper nest 820.

Figure 8C:
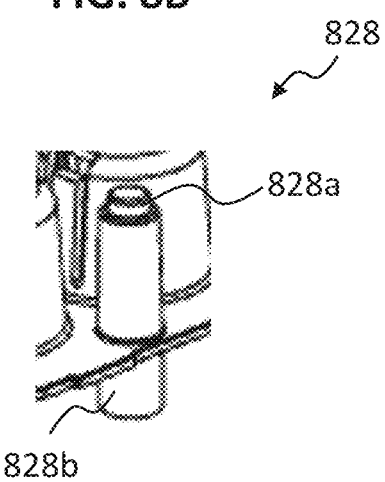
FIG. 8C depicts a schematic illustration of a spacer on an example variation of a dropper nest.

In some variations, a dropper nest 820 may include one or more spacers that may enforce a certain distance between adjacent layered or stacked dropper nests 820. For example, as shown in FIG. 8B, a dropper nest 820 may include one or more spacers 828 arranged on the support surface 822 or other suitable surface. The variation shown in FIG. 8B includes four spacers 828 arranged on corners of the support surface 822, though in other variations the dropper nest 820 may include any suitable number of spacers 828 arranged in any suitable layout pattern. The spacers 828 may include projections extending upwards and/or downwards from the support surface 822, and may be integrally formed with or coupled to the support surface 822. In some variations, the spacers 828 of one dropper nest 820 may be aligned with the spacers 828 of an adjacent dropper nest 820 (e.g., a dropper nest 820 arranged above and/or a dropper nest 820 arranged below), such that each spacer 828 may removably engage with a spacer 828 on an adjacent dropper nest 820. For example, as shown in FIG. 8C, a spacer 828 may include an upper portion 828a and a lower portion 828b, where the upper portion 828a may couple to the lower portion of a spacer on an adjacent dropper nest located above the upper portion 828a, and similarly the lower portion 828b may couple to the upper portion of a spacer on an adjacent dropper nest located underneath the lower portion 828b. Such coupling may include the engagement of mating features. For example, as shown in FIG. 8C, the upper portion 828a may include a longitudinal projection including a distal tip of a smaller diameter configured to fit inside an internal recess located in the lower portion of an adjacent spacer. As another example, the upper portion 828a may include a recess configured to receive lower portion of an adjacent spacer. However, spacers 828 on adjacent dropper nests 820 may engage in any suitable manner, such as with fasteners (e.g., magnetic elements) or other mechanical interfit features (e.g., with slip fit interference).

Similar to other packaging structures described above, the dispenser covers 824 may be arranged on the support surface 822 in an array, such as a regular array (e.g., hexagonal, rectangular, etc.), irregular array, or any suitable layout pattern. While the variation shown in FIG. 8B includes 48 dispenser covers, it should be understood that the dropper nest 820 may include any suitable number of dispenser covers. Similar to the pump nest described above, in some variations such as that shown in FIG. 8F, adjacent dispenser covers 824 may be coupled, such as with one or more interconnecting walls 823 that extend between adjacent dispenser covers 824. Additionally or alternatively, adjacent dispenser covers may share a common structure such as a wall as shown in FIG. 8F.

Figure 8G:
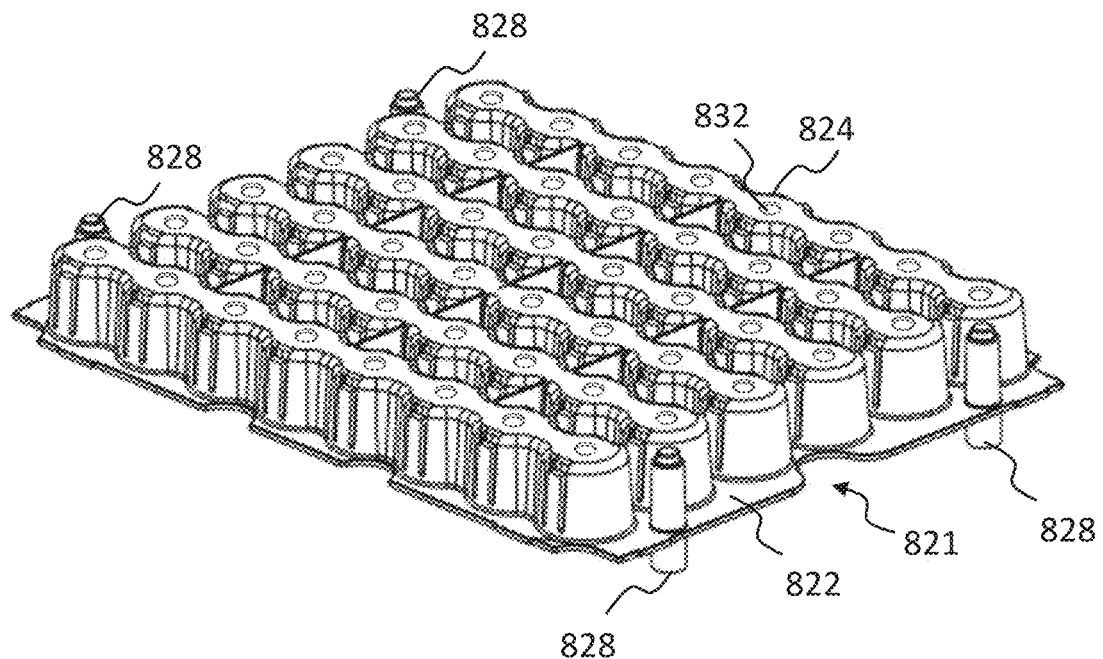
FIGS. 8G and 8H depict schematic illustrations of an example variation of a dropper nest with dispenser cover access openings.
Figure 8H:
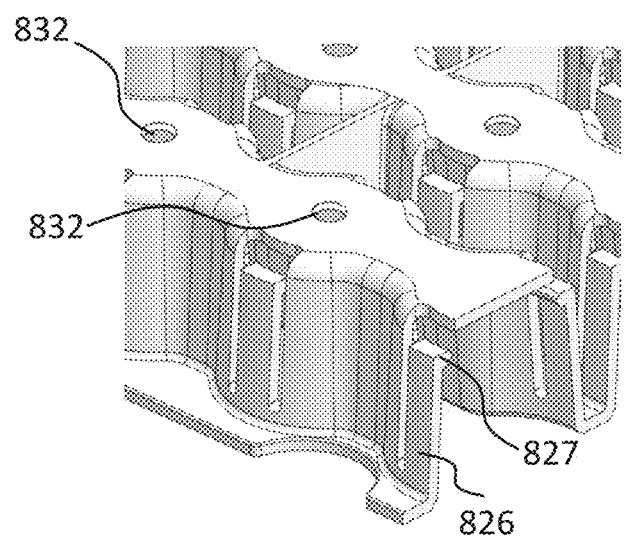

In some variations, a dispenser cover 824 may be defined by one or more walls that are configured to surround a drop dispenser 802 or a group of drop dispensers 802. The wall may be contoured to closely follow the contour of drop dispenser(s) 802, which may help enable space efficient packing of drop dispensers in the dropper nest 820. While the variation shown in FIG. 8B include substantially continuous walls that extend along a row of dispenser covers 824, in some variations some or all dispenser covers 824 may be formed from multiple, discrete walls that are configured to surround at least a portion of the perimeter of the dispenser to be contained in the dispenser cover 824. In some variations, some or all of the dispenser covers 824 may have a closed top or distal end as shown in FIG. 8F, though in some variations some or all of the dispenser covers 824 may have a closed end to completely cover a drop dispenser 802 contained therein. Furthermore, in some variations, as shown in FIGS. 8G and 8H depicting another example variation of a dropper nest, some or all of the dispenser covers 824 may include at least one opening or through hole 832 or other open top to allow access to individual drop dispensers 802 contained in the dispenser cover 824. For example, to assemble a drop dispenser 802 and corresponding dropper container using the variation shown in FIGS. 8G and 8H, the drop dispenser 802 may be directly accessed through hole 832 to individually compress the drop dispenser 802 onto its corresponding dropper container located below the drop dispenser 802. Although the holes 832 are shown in FIGS. 8G and 8H as circular and centered in each dispenser cover 824, it should be understood that in some variations the holes 832 may have any suitable shape (e.g., oval, elliptical, rectangular, square, other polygonal shape, etc.) and may be centered or off-centered in the dispenser cover 824. Each of a plurality of drop dispensers 802 may be assembled (coupled to a respective dropper container) in sequence using this technique. This may be useful, for example, to reduce the amount of compression required to be exerted by a robotic manipulator or manual manipulator at any one time to result in successful assembly. It should be understood that multiple drop dispensers 802 (e.g., two, three, four, an entire row, an entire column, etc.) may also be simultaneously assembled through direct contact through holes 832 in the dispenser covers 824 (e.g., provided that a sufficient amount of compression can be exerted to effect multiple simultaneous assemblies).

Additionally or alternatively, in some variations a dispenser cover 824 may include one or more alignment features (e.g., similar to that described above with respect to the pump nest guide and/or pump nest) to orient a drop dispenser in a predetermined rotational orientation within the dispenser cover 824.

Furthermore, in some variations, a dispenser cover may include one or more locking members configured to couple a drop dispenser to the dispenser cover. For example, as shown in FIG. 8D, a dispenser cover 824 may include at least one locking flexure member 826 configured to couple a drop dispenser to the dispenser cover 824. In some variations, a dispenser cover may include multiple locking members (e.g., two locking flexure members 826). The locking members may be distributed equally or radially symmetrically around the dispenser cover, so as to retain the pump in the dispenser cover in a balanced manner. For example, as shown in FIG. 8D, a dispenser cover 824 may include two locking flexure members 826 arranged 180 degrees rotationally offset from each other. In some variations, the locking member(s) may engage with a radial projection of the drop dispenser 802 to couple the drop dispenser 802 to the dispenser cover 824. When the locking members across the dropper nest 820 couple a set of multiple drop dispensers 802 to the dropper nest 820, all secured dispenser 802 may advantageously be manipulated (e.g., transported) by handling the dropper nest 820 itself, as further described below. Accordingly, the dropper nest with such locking members may enable easy, efficient handling of multiple dispensers simultaneously.

FIG. 8F illustrates an example variation of a locking flexure member 826 coupling to a drop dispenser 802. The locking flexure members 826 may be formed from or coupled to the dispenser cover 824, though in other variations similar structures may be located in another part of the pump nest 220. As shown in FIG. 8F, a locking flexure member 826 may include an arm with a fixed proximal end and a free distal end with a stop 827. The locking flexure member may generally extend longitudinally along the dispenser cover 824, parallel to a central axis of the dispenser cover, and may be configured to flex in a radial direction (e.g., relative to the central axis of the dispenser cover). For example, the locking flexure member 826 may flex radially outward to receive the drop dispenser 802 within the dispenser cover 824. The locking flexure member 826 may be similar in shape to the locking flexure member 226 described above with respect to FIGS. 6B and 6C. For example, the stop 827 may include a lower sloped surface to further ease passage of the drop dispenser 802 into the dispenser cover 824. When the drop dispenser 802 reaches a certain insertion depth into the dispenser cover 824, a radial rib 803 or other projection on the drop dispenser 802 may pass beyond the stop 827, which permits the locking flexure member to return inwards to its previous radial position. As shown in FIG. 8F, the stop 827 may abut the radial rib 803 and urge the drop dispenser 802 against a surface (e.g., shoulder surface or covered top) of the dispenser cover 802, to thereby secure the drop dispenser 802 against the dispenser cover. In some variations, the stop 827 may also include an upper sloped surface that facilitates easier removal of the drop dispenser 802 from the dispenser cover with application of sufficient removal or separation force.

In some variations, the locking flexure member 826 may include a bias (e.g., inherent in the form or material of the flexure member) that urges the locking flexure member 826 radially inward, to thereby further secure the drop dispenser 802 within the dispenser cover. Additionally or alternatively, other locking features may help couple the pump to the dispenser cover. For example, the dispenser cover may include frictional features (e.g., ribs or other textural features, rubberized or other high-friction materials, etc.) located on an internal surface of the dispenser cover to engage the drop dispenser 802 within the dispenser cover.

In some variations, like the packaging structure described above, the dropper nest 820 may be injection molded out of a suitably rigid plastic, though the dropper nest may be formed in any suitable manner (e.g., 3D printed, milled, etc.). In some variations, the dropper nest 820 may include a material stable under gamma ray sterilization (e.g., HDPE). Furthermore, some or all of the dispenser covers may be integrally formed with the support surface. Additionally or alternatively, some or all of the dispenser covers may be separately formed from the support surface and be coupled to the support surface through a mechanical interfit (e.g., threads, snap fit, other mating features, etc.), suitable fasteners (e.g., epoxy, connectors, etc.), and/or suitable joining process (e.g., thermal welding).

An example variation of a dropper nest (with 48 dispenser covers) is shown in greater detail in FIGS. 18A-18G.

Dropper Container Nest Assembly

Figure 9A:
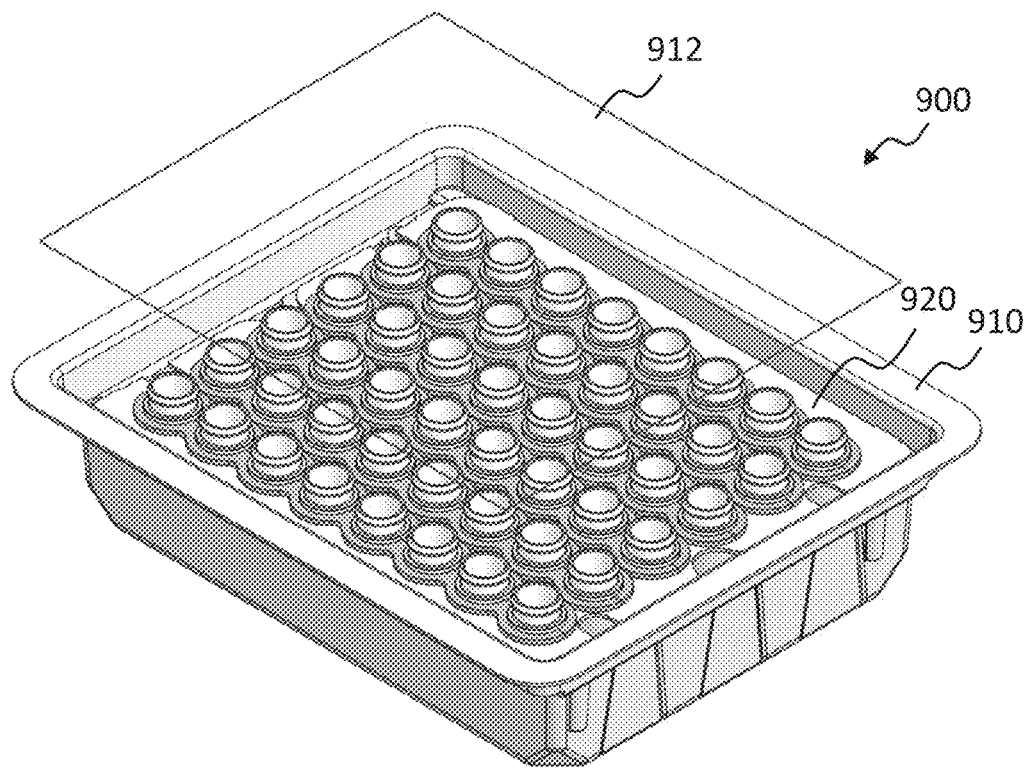
FIG. 9A depicts a schematic illustration of an example variation of a dropper container nest assembly.

FIG. 9A depicts a schematic illustration of an example variation of a dropper container nest assembly 900. The dropper container nest assembly 900 may include one or more packaging structures in a tub 910 or other suitable containers, where each packaging structure may contain a plurality of containers (e.g., bottles). The dropper container nest assembly may, for example, store a plurality of bottles (e.g., flexible bottles, such as made of pliable plastic) in a protective and/or organized manner that reduces the likelihood of damage to the bottles and/or enables easy collective transport of the bottles. Packaging structures may sit within the tub 910 as shown in FIG. 7A, and may be accessible through an upper tub opening, which may be sealed (e.g., with a seal 912 may include metal foil, plastic film, or any suitable material). The seal 912 may help maintain sterility of the contents of the dropper container nest 900 until the tub is opened (e.g., by peeling off or otherwise breaching the seal 912), such as to access the packaging structure(s) contained therein.

Dropper Container Nest

Figure 9B:
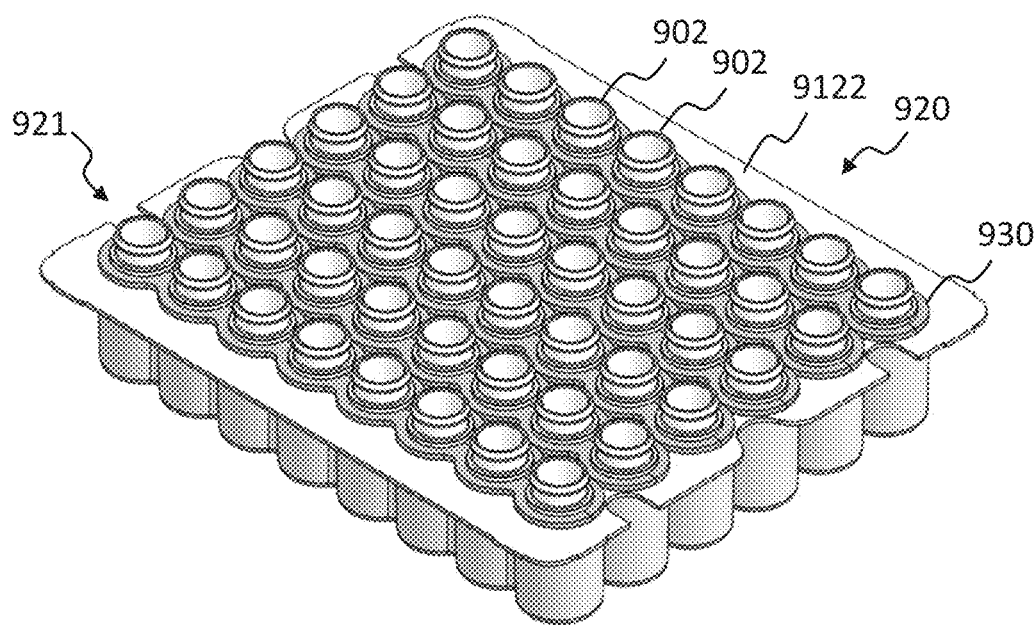
FIGS. 9B and 9C depict assembled and partially exploded views, respectively, of a portion of an example variation of a dropper container nest assembly.

As shown in FIG. 9B, the packaging structures in the dropper container nest assembly may include one or more dropper container nests 920. In some variations, the dropper container nests 920 may be similar to the container nests 720 described above. For example, a dropper container nest 920 may include a support surface 922 and a plurality of container seats 824 arranged on the support surface. Additionally, a dropper container nest 920 may be configured to rest within the tub 910 or other container, or may be a standalone structure that is sealed directly, rather than (or in addition to) being sealed within the tub. A dropper container nest 920 may be generally rectangular as shown in FIG. 9B, or may have any suitable shape. A dropper container nest 920 may include one or more cutouts 921 to help facilitate manual removal of the dropper container nest 920 from the tub, and/or may include any suitable engagement features (e.g., suction, a smooth surface to which a suction cup or vacuum source may attach, fasteners, etc.) to help facilitate handling of the dropper container nest 920.

Furthermore, the container seats 924 may arranged on the support surface in an array similar to that described above for the dispenser covers 824 in a dropper nest 820 (e.g., regular array such as hexagonal or rectangular, an irregular array, or any suitable layout pattern). If the containers to be placed in the dropper container nest 920 are intended to be assembled with drop dispensers in the dropper nest assembly 820, then the layout arrangement of the container seats 924 may be identical to the layout arrangement of the dispenser covers 824, such that the alignment of the dropper container nest 920 and the dropper nest 820 results in collective alignment of the containers with corresponding drop dispensers. Other aspects of the container seats 924 may be similar to those of the container seats 724 described above. Additionally or alternatively, in some variations some or all of the container seats 924 may have a bottom with at least one opening or through hole (e.g., similar to the container nest 720 described above with respect to FIG. 7D) to allow individual access to a dropper container contained therein. For example, to assemble a drop dispenser 802 and corresponding dropper container using a dropper container nest 920 having openings in the container seat bottom, the dropper container may be directly accessed through such openings to individually compress the dropper container onto its corresponding drop dispenser 802 above the dropper container. These openings may have any suitable shape (e.g., circular, oval, elliptical, other polygonal shape, etc.) and may be centered or off-centered within the container seat bottom. Each of a plurality of dropper containers may be assembled (coupled to a respective drop dispenser) in sequence using this technique. This may be useful, for example, to reduce the amount of compression required to be exerted by a robotic manipulator or manual manipulator at any one time to result in successful assembly. It should be understood that multiple dropper containers (e.g., two, three, four, an entire row, an entire column, etc.) may also be simultaneously assembled through direct contact through openings in the container seats 924 (e.g., provided that a sufficient amount of compression can be exerted to effect multiple simultaneous assemblies).

In some variations, the dropper container nest may be injection molded out of a suitably rigid plastic, though the dropper container nest may be formed in any suitable manner (e.g., 3D printed, milled, etc.). In some variations, the dropper container nest may include a material stable under gamma ray sterilization (e.g., HDPE). Furthermore, some or all of the container seats may be integrally formed with the support surface. Additionally or alternatively, some or all of the container seats may be separately formed from the support surface and be coupled to the support surface through a mechanical interfit (e.g., threads, snap fit, other mating features, etc.), suitable fasteners (e.g., epoxy, connectors, etc.), and/or suitable joining process (e.g., thermal welding).

Reinforcement Members

In some variations, the dropper container nest assembly 900 may further one or more reinforcement members 930. The reinforcement members 930 may function to bolster the dropper containers 902 against deformation. For example, since dropper containers 902 may include a flexible or pliable material (e.g., to enable a user to expel a fluid from the dropper container 902 by squeezing the dropper container 902), the dropper containers 902 may be susceptible to buckling or other deformation when drop dispensers are coupled to the dropper containers through an axial force (e.g., applied from above the dropper containers). The reinforcement members 930 may include a material that is more rigid than the dropper containers 902 (e.g., rigid plastic, metal, etc.). Suitable materials may include, for example, polycarbonate, acrylic, ABS, PETG, rigid PVC, crystal styrene, etc. Additionally or alternatively, the reinforcement members 930 may substantially surround the body of the dropper containers 902 in a snug manner, so as to better absorb and/or distribute axial forces applied to the dropper containers 902 during dispenser assembly.

Figure 9C:
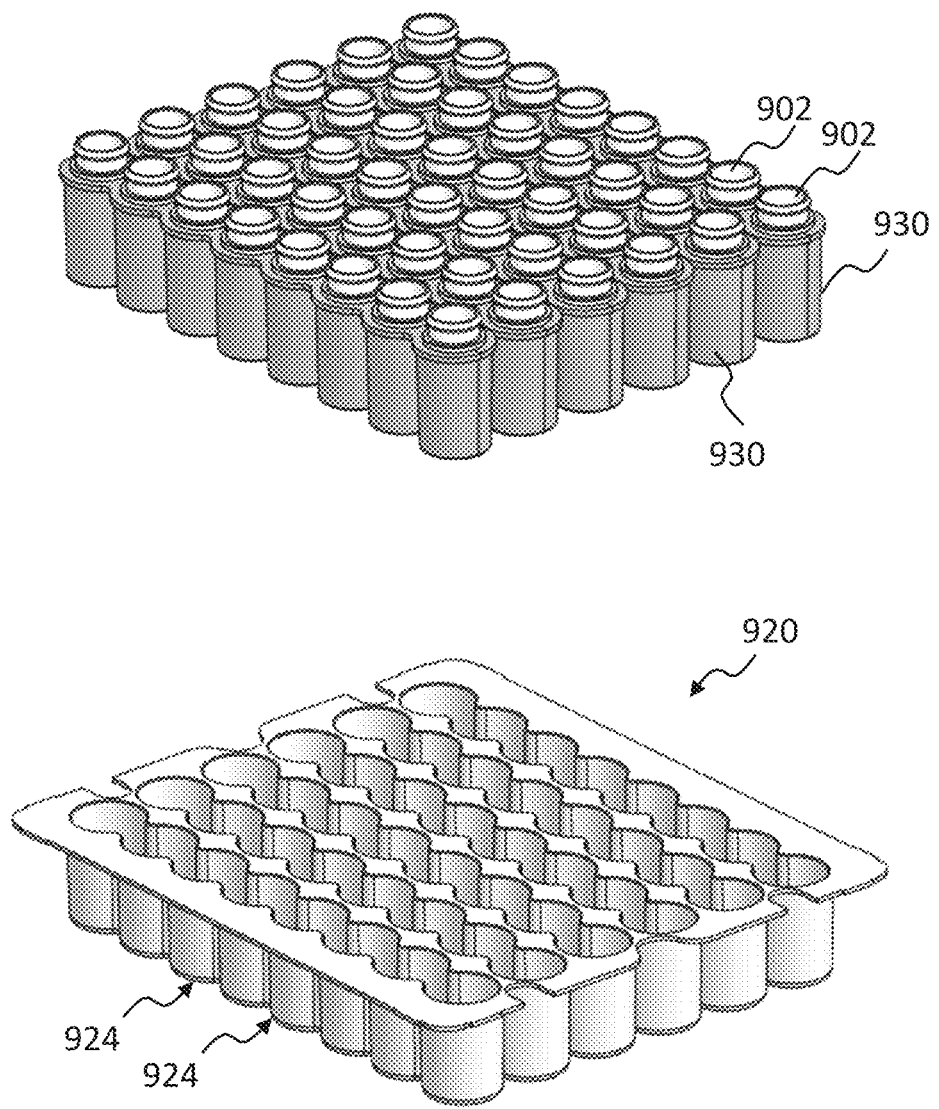

Some or all reinforcement members may be distinct and separable from the dropper container nest 920. For example, as shown in FIG. 9C, the reinforcement members 930 may be removed, along with dropper containers 902, from the dropper container nest 920. Alternatively, some or all reinforcement members may be coupled to or integrally formed with the dropper container nest 920. The reinforcement members may be injection molded, milled, cast, or manufactured in any suitable manner.

Figure 9D:
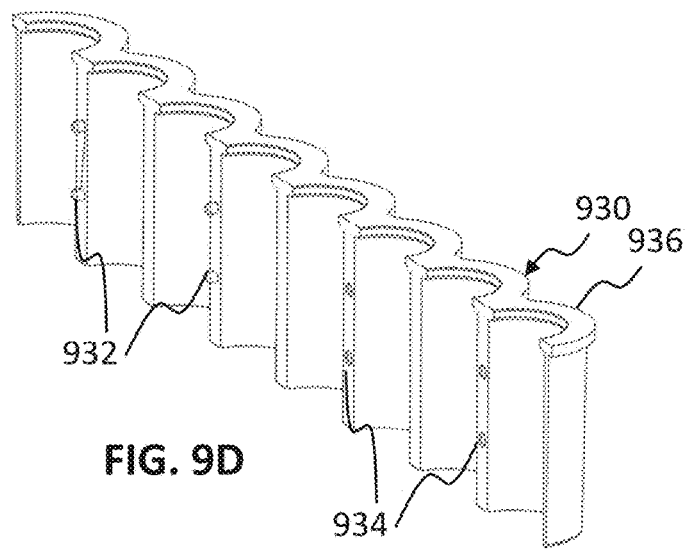
FIG. 9D is a schematic portion of an example variation of a reinforcement member in a dropper container nest assembly.
Figure 9E:
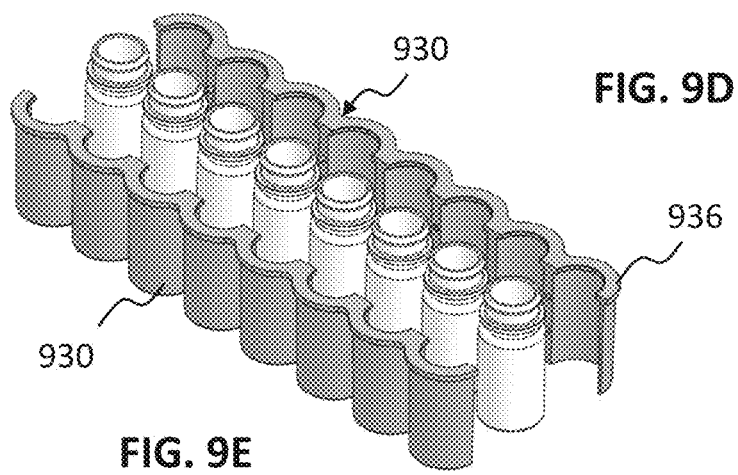
FIGS. 9E and 9F are exploded and assembled views, respectively, of an example variation of reinforcement members and dropper containers in a dropper container nest assembly.
Figure 9F:
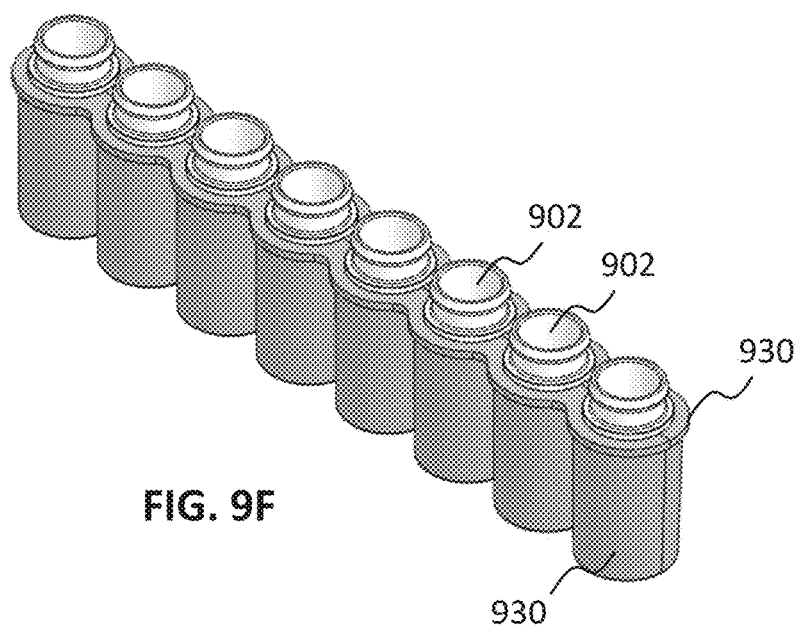

In some variations, a reinforcement members 930 may be configured to engage with multiple dropper containers 902, which may further help distribute forces across a greater area to help reduce deformation of the dropper containers 902. For example, as shown in FIGS. 9E and 9F, a group (e.g., row or column) of dropper containers 902 may be arranged between two scalloped reinforcement members 930. Each scalloped segment of the reinforcement member 930 may be sized and shaped to receive a contoured portion (e.g., half) of a dropper container 902. Furthermore, as shown in FIG. 9D, each scalloped reinforcement member may include one or more mating features (e.g., pegs 932 and/or receiving holes 934) such that two opposite-facing reinforcement members 930 may align and mate appropriately to form a snug fit around the dropper containers 902 (FIG. 9F). Alternatively, multiple reinforcement members 930 may couple together in any suitable manner (e.g., along a hinge). While the scalloped shape of the reinforcement member 930 shown in FIG. 9D includes a semicircular scalloped segment to accommodate part of a cylindrical dropper container 902, it should be understood that the reinforcement members 930 may have any suitable shape for other containers. For example, a reinforcement member 930 may include a sloped inner surface to accommodate a dropper container 902 with a wider base that tapers to a narrower neck. Alternatively, in some variations, the dropper container nest assembly 900 may include a discrete reinforcement member (e.g., sleeve, partial sleeve, collars, rings, etc.) for each respective dropper container 902.

In some variations, the dropper container nest assembly 900 may include a shoulder or flange to engage with the dropper container nest 920. For example, as shown in FIGS. 9D and 9E, a reinforcement member may include a shoulder 936 configured to rest upon the support surface of the dropper container nest 920. The shoulders 936 may function to further distribute axial forces applied to the dropper container 902 across the dropper container nest 920, and/or help control the insertion depth of the reinforcement members 930 and/or dropper containers 902 within the container seats 924 in the dropper container nest 920.

Figure 19:
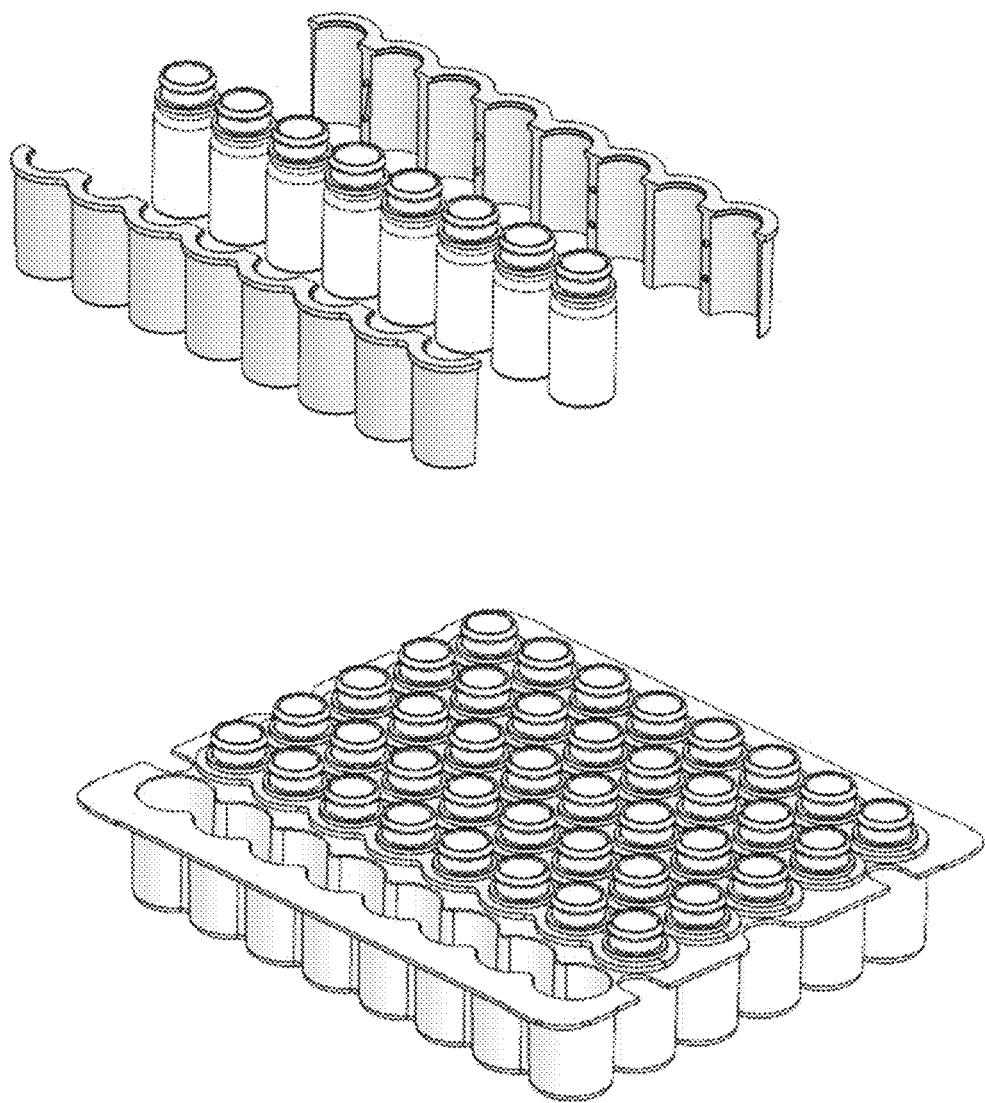
FIG. 19 is a partially exploded view of an example variation of a dropper nest assembly
Figure 20A:
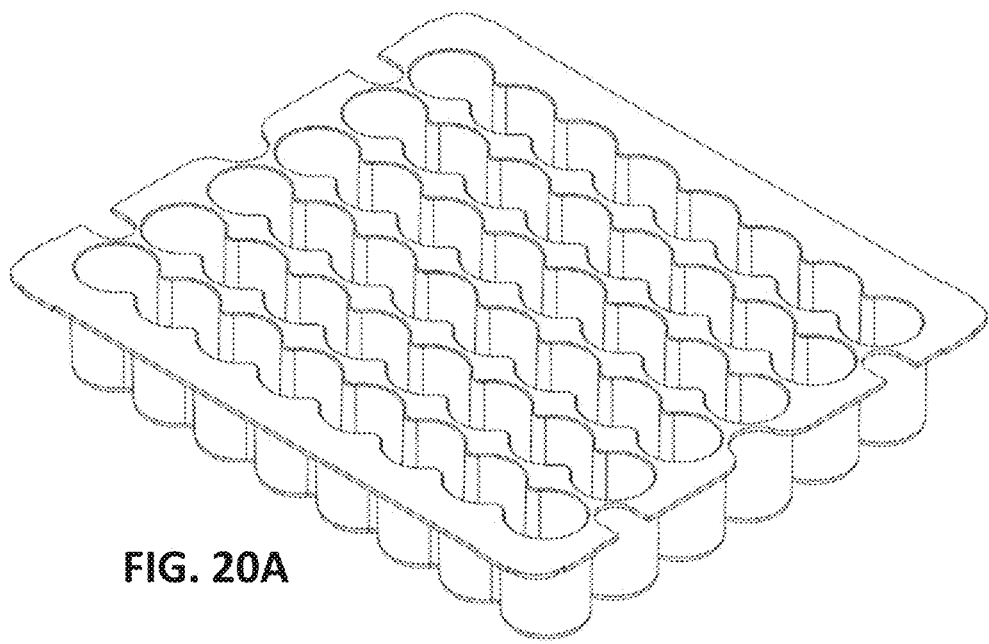
FIGS. 20A-20E are a perspective view, a top view, a bottom view, a front view, and a side view, respectively, of an example variation of a dropper container nest.
Figure 20B:
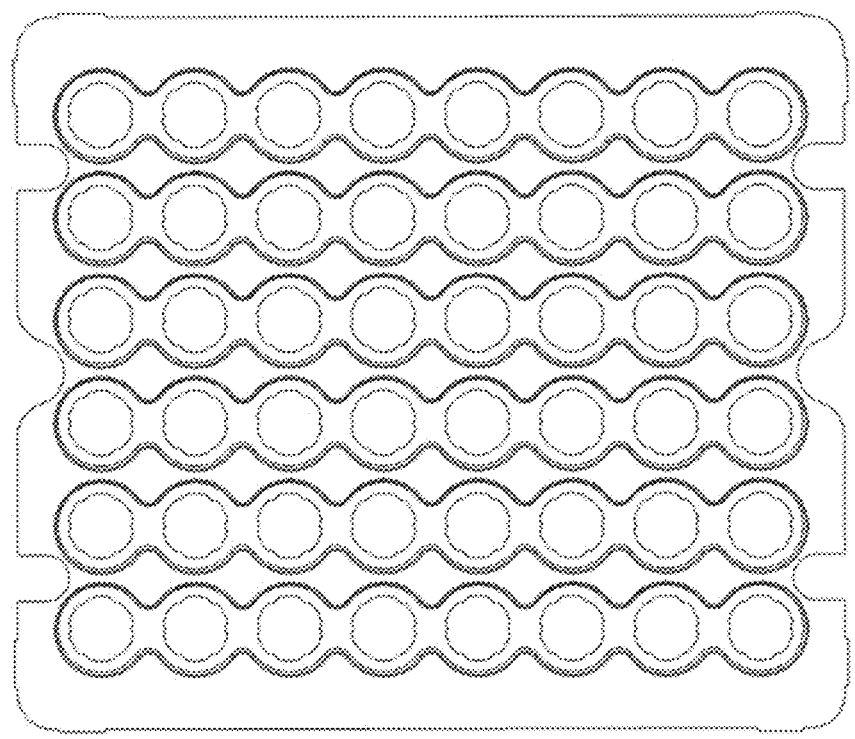
Figure 20C:
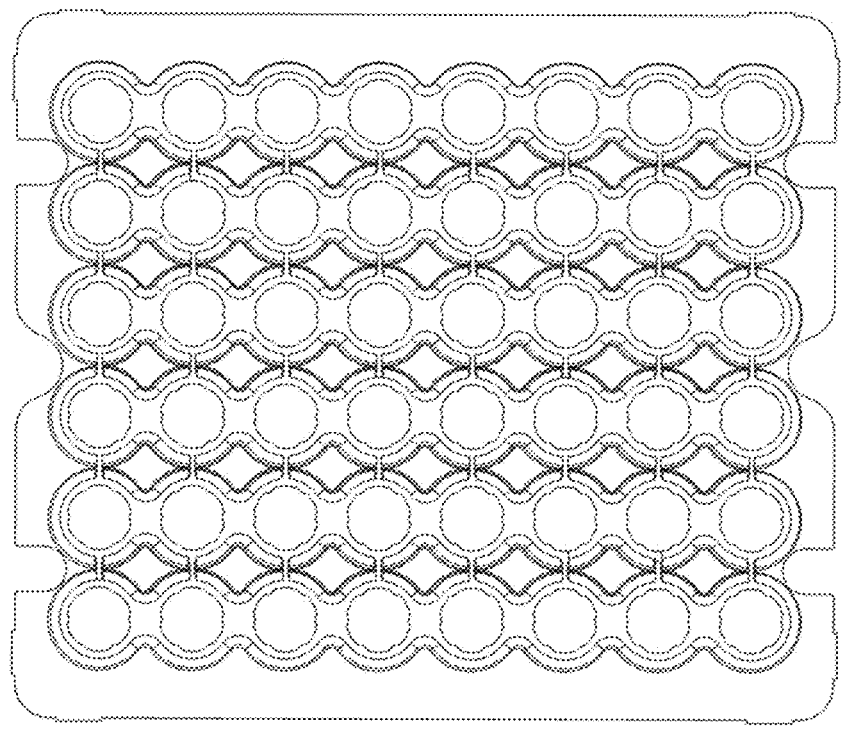
Figure 20D:
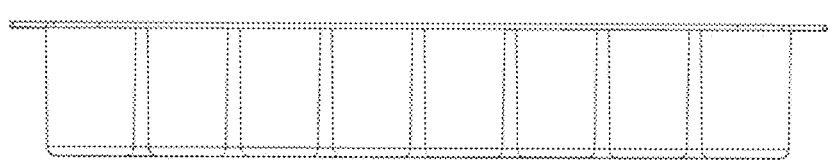
Figure 20E:
Figure 21A:
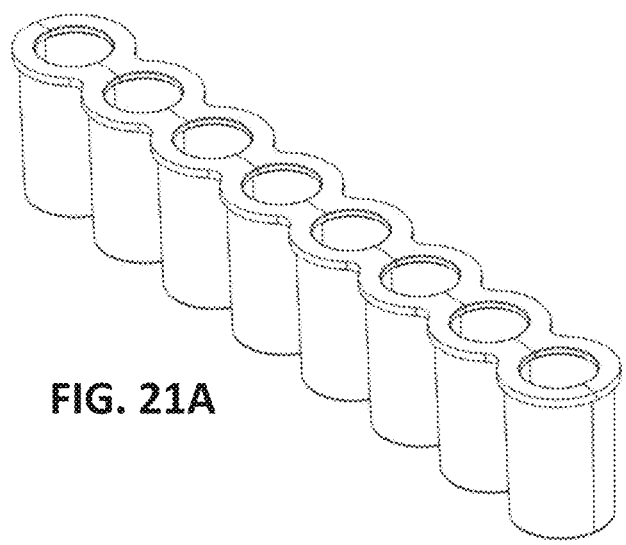
FIGS. 21A and 21B are assembled and exploded views, respectively, of an example variation of reinforcement members in a dropper nest assembly.
Figure 21B:
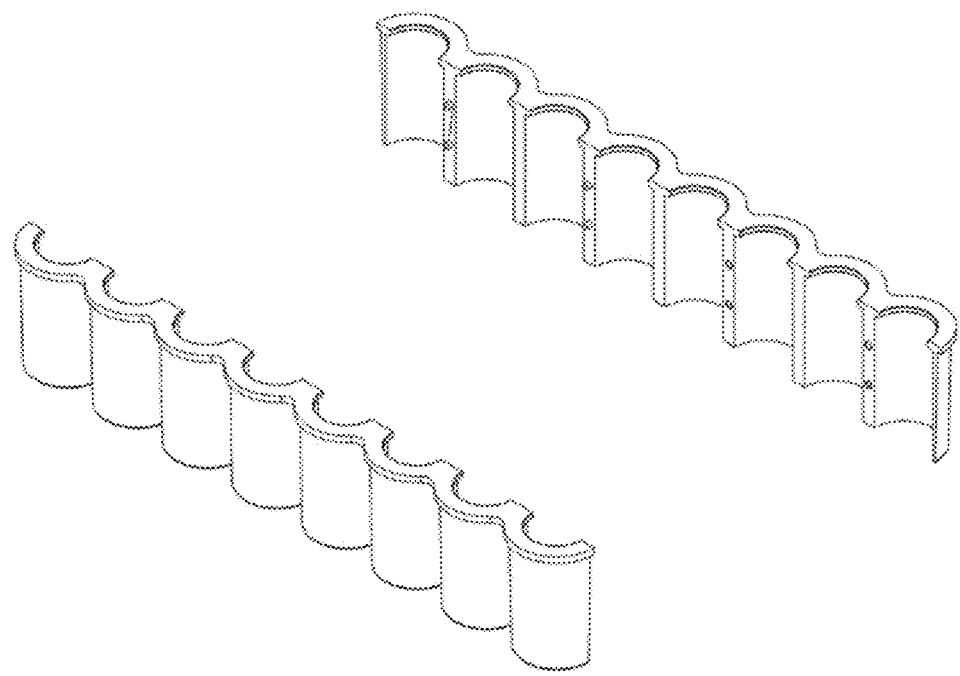

An example variation of a dropper container nest (with 48 container seats) is shown in greater detail in FIG. 19. Additionally, an example variation of a dropper container nest is shown in FIGS. 20A-20E, while an example variation of reinforcement members is shown in FIGS. 21A-21E.

Methods for Assembling Nested Components

As described above, various nested packaging assemblies may include packaging structures for storing and protecting individual component pieces (e.g., dispensers such as pumps or drop dispensers, or containers) that may be manipulated in sets to accommodate large-scale, collective or simultaneous assemblies (e.g., each assembly including a dispenser coupled to container). Furthermore, the nested packaging assemblies may be easily manipulated with automated equipment, such as equipment with robotic arms, etc. In some variations, the use of such automated equipment with the nested packaging assemblies, as described herein, may help reduce the number of manual operators who must interact with the components. Reducing manual involvement may be advantageous in certain applications, such as in the manufacture of drug container and dispenser assemblies which are subject to sterility requirements or goals. For example, in some variations, a method for assembling components from packaging structures (such as those described herein) may be performed to assemble dispenser assemblies that dispense drugs. For example, the method may be performed to assemble drug dispenser assemblies that contain preservative-free formulations for which it may be particularly important to maintain sterility.

Figure 10:
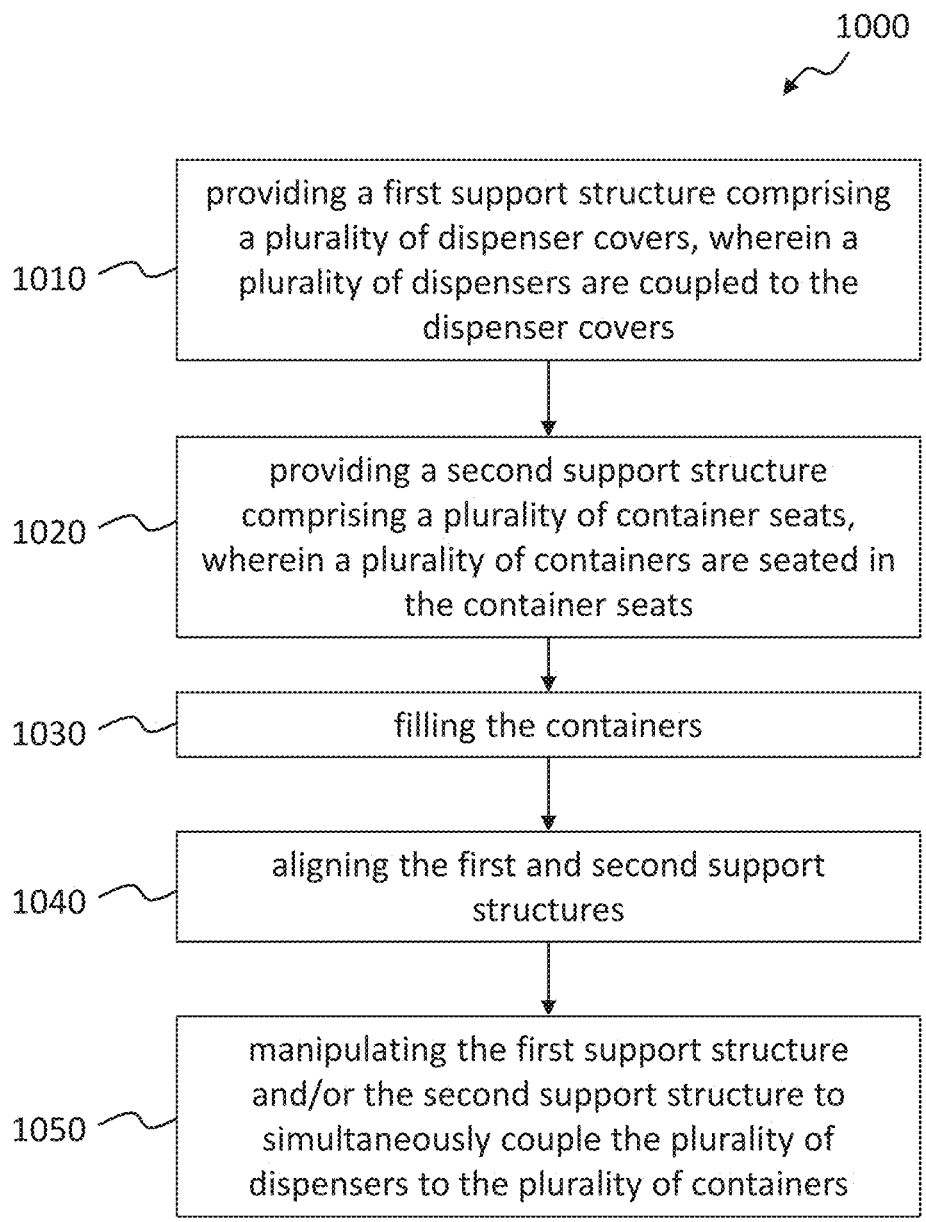
FIG. 10 depicts a flowchart of an example variation of a method for assembling packaging structures.

Methods for assembling nested components may utilize one or more of the packaging assemblies and/or packaging structures described above. For example, as shown in the flowchart depicted in FIG. 10, an example variation of a method 1000 for assembling dispenser assemblies may include providing a first support structure comprising a plurality of dispenser covers 1010 and providing a second support structure comprising a plurality of container seats 1020. A plurality of dispensers may be coupled to the dispenser covers, and a plurality of containers may be seated in the container seats. The method 1000 may further include filling the containers 1030 with a substance (e.g., drug) to be dispensed from the container, then aligning the first and second support structures 1040 to align the plurality of dispensers with the plurality of containers. After the first and second support structures are aligned, the method may further include manipulating the first support structure and/or the second support structure 1050 to simultaneously couple the plurality of dispensers to the plurality of containers. The coupled dispensers and containers form a plurality of dispenser assemblies, which may thereafter remain in one or both support structures, or may be removed for subsequent processing (e.g., labeling, further packaging, quality testing, shipment, etc.). In some variations, at least a portion of the method 1000 may be performed within a self-contained, aseptic isolator with robotic manipulator(s) suitable for manipulating nesting packaging structures such as those described herein. For example, at least a portion of the method 100 may be performed by an aseptic filling workcell available from Vanrx Pharmasystems Inc. (Burnaby, British Columbia, Canada), STERIS Applied Sterilization Technologies (Mentor, Ohio, USA), Aseptic Technologies (Raleigh, N.C., USA), Staubli Corporation (Duncan, S.C., USA), or other suitable automated filling equipment. Additionally or alternatively, at least a portion of the method 100 may be performed manually.

Figure 11:
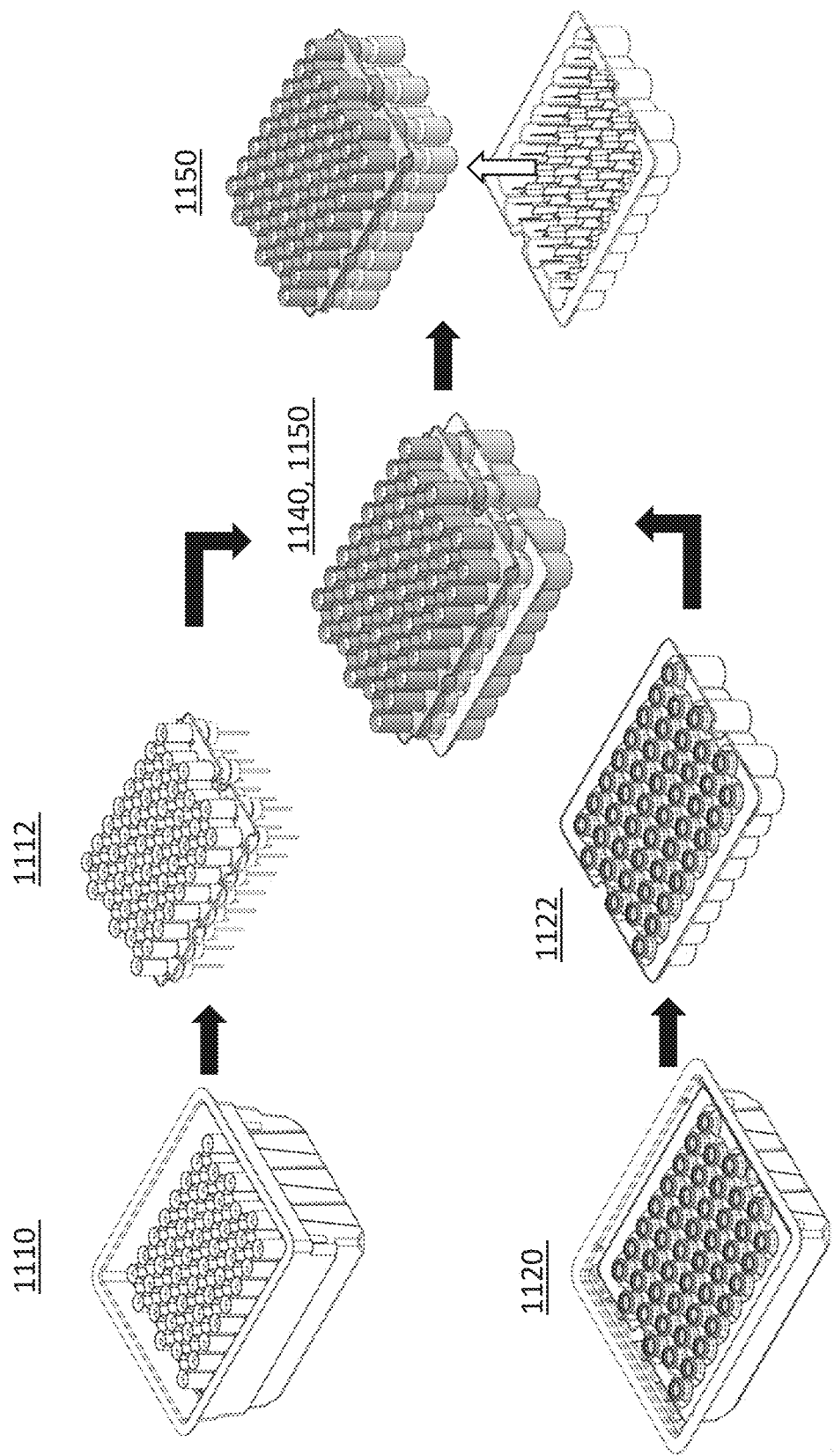
FIG. 11 is a schematic illustration of an example variation of a method for assembling dispenser assemblies including pump dispensers.

FIG. 11 depicts an example variation of a method for assembling pump dispenser assemblies, with reference to the pump nest assembly 200 (e.g., as shown in FIG. 2A) and the container nest assembly 700 (e.g., as shown in FIG. 7A). The pump nest assembly may include a tub containing a pump nest, a pump nest guide, and a plurality of pumps (e.g., nasal pumps) arranged in the pump nest and pump nest guide (1110). The pumps may be coupled to the pump nest. The container nest assembly may include another tub containing a container nest and a plurality of containers (e.g., drug containers) arranged in the container nest (1120). The container nest may be removed from its tub, such as with a robotic manipulator that engages the container nest with suction (or gripping features, etc.) (1122). The containers in the container nest may be filled with a desired substance (e.g., a liquid drug or other drug suitable for dispensing through a pump). Separately, the pump nest may be removed from its tub, separating the pump nest and pumps from the pump nest guide and the tub (1112). For example, a robotic manipulator may engage the pump nest with suction or in another suitable manner, and because the pumps are coupled to the pump nest (e.g., via locking members as described above), manipulation of the pump nest may efficiently enable manipulation of the pumps as well. Accordingly, the robotic manipulator(s) may align the pump nest over the container nest (1140), then move the pump nest and container nest toward each other (e.g., press the pump nest down toward the container nest). The pump nest and container nest may be moved closer together until the pumps and containers couple together, such as via snap fit (1150). Accordingly, manipulation of the pump nest and the container nest may effect simultaneous assembly of multiple pumps and containers. Additionally or alternatively, in some variations individual pumps in the pump nest and/or individual containers in the container nest may be separately manipulated to form only a selected portion of the assemblies among the array of pumps and containers. For example, a pump may be individually accessed through an opening in its dispenser cover in the pump nest, and pushed down toward its corresponding container. Additionally or alternatively, a container may be individually accessed through an opening in its container seat in the container nest, and pushed up toward its corresponding pump). Multiple assemblies may be formed in such a manner, and may advantageously permit efficient assembly using the pump nest assembly and container nest assembly even if the robotic manipulator is limited in its ability to exert compressive force to form all nested assemblies simultaneously. The resulting dispenser assemblies (each including a pump coupled to a filled container) may be organized within the container nest for further transport. In some variations, the dispenser assemblies may be collectively removed from the container nest (1150) by again manipulating the pump nest relative to the container nest. That is, because the pumps remain coupled to the pump nest and the containers are in turn coupled to the pumps, the array of dispenser assemblies may be collectively manipulated with the pump nest.

Figure 12:
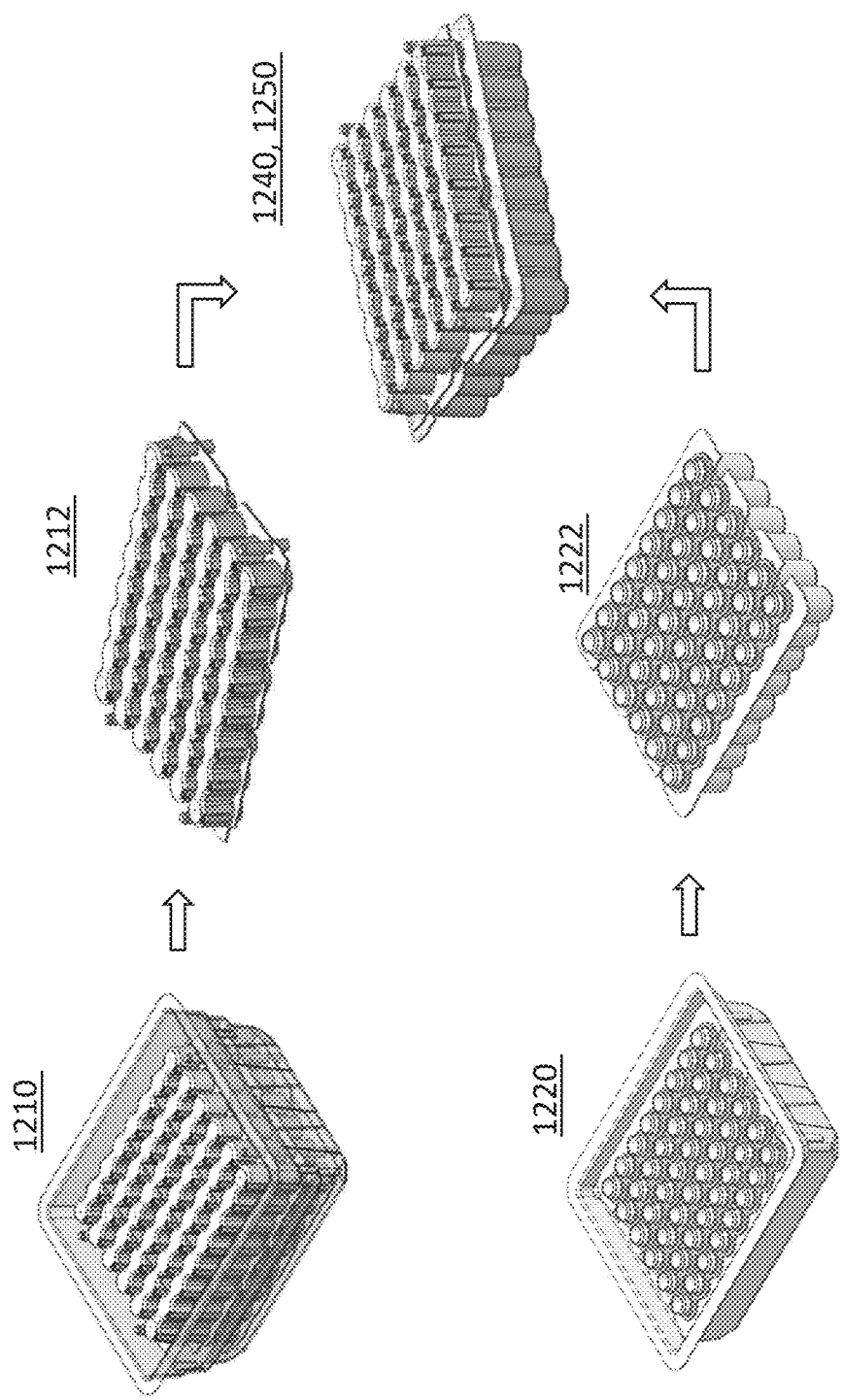
FIG. 12 is a schematic illustration of an example variation of a method for assembling dispenser assemblies including drop dispensers.
Figure 13A:
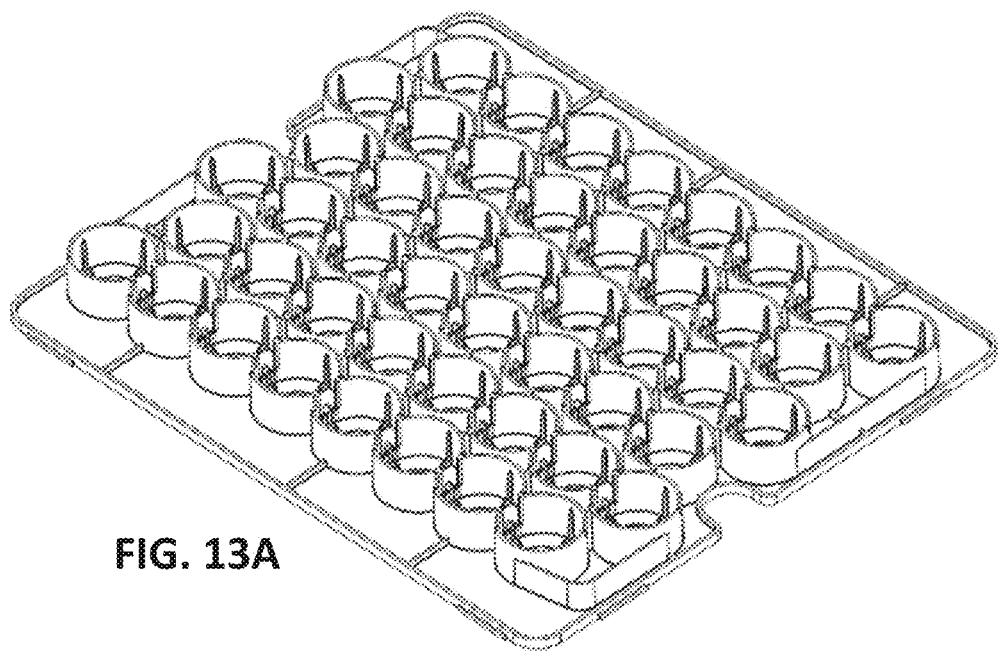
FIGS. 13A-13E are a perspective view, a top view, a bottom view, a front view, and a side view, respectively, of an example variation of a pump nest guide with 48 dispenser seats.
Figure 13B:
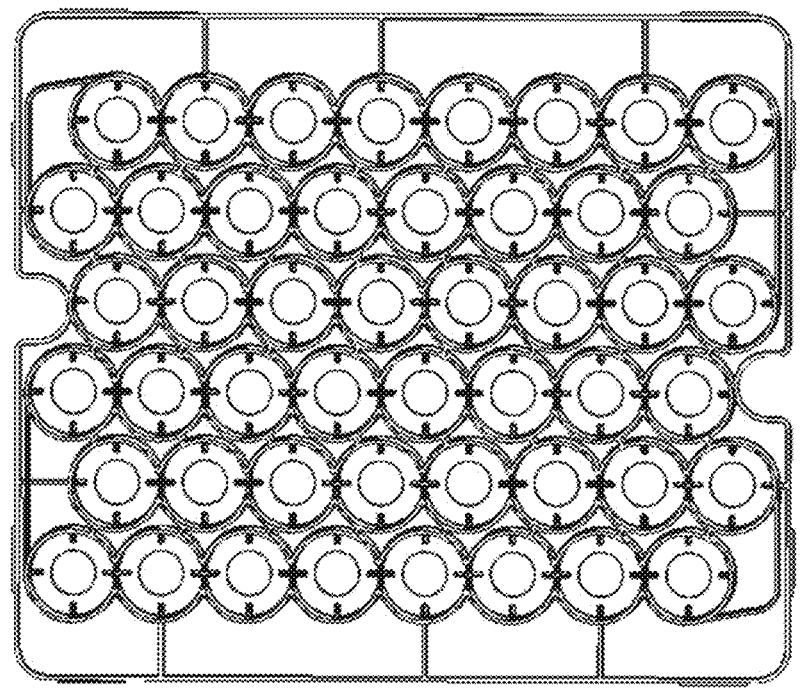
Figure 13C:
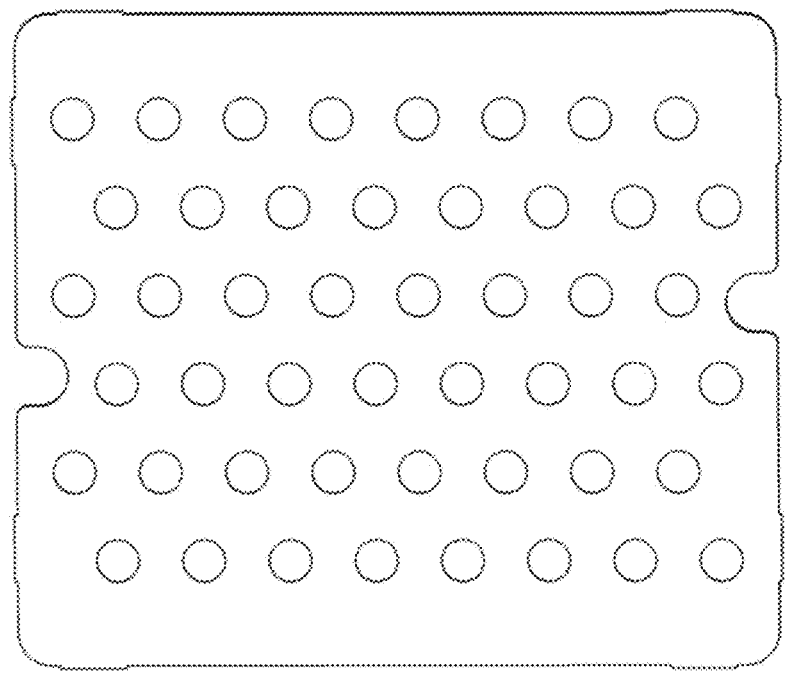
Figure 13D:
Figure 13E:
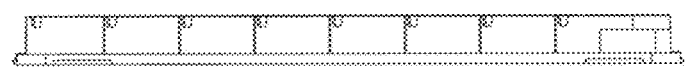
Figure 14A:
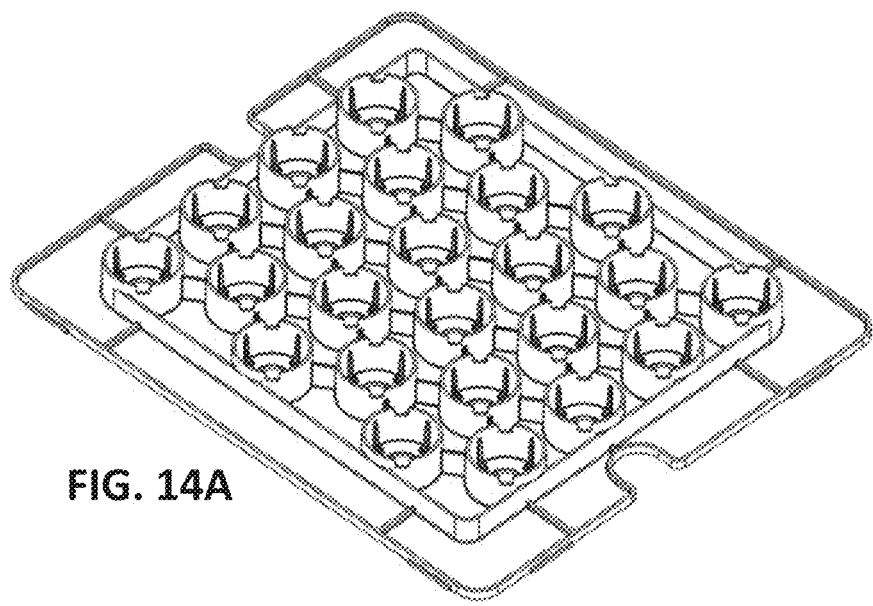
FIGS. 14A-14E are a perspective view, a top view, a bottom view, a front view, and a side view, respectively, of an example variation of a pump nest guide with 24 dispenser seats.
Figure 14B:
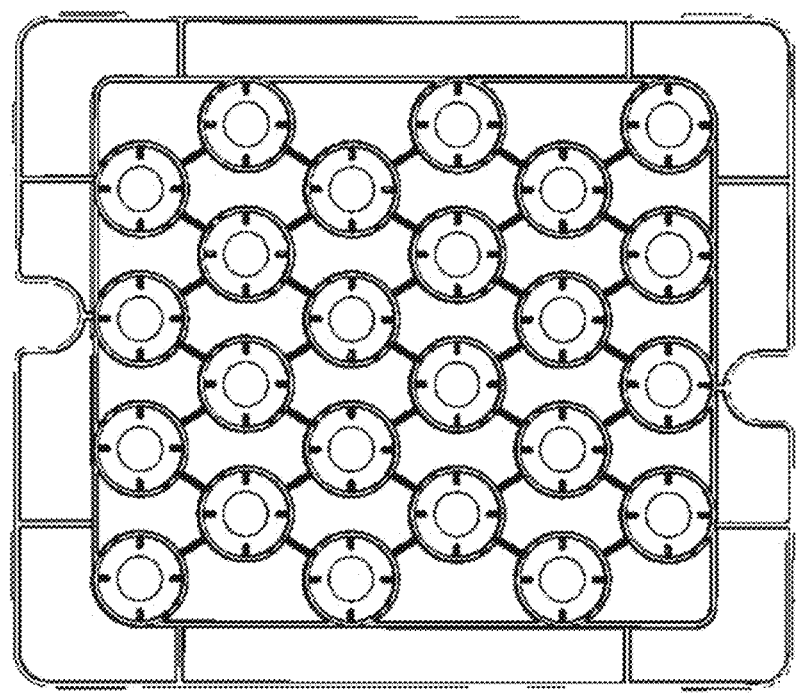
Figure 14C:
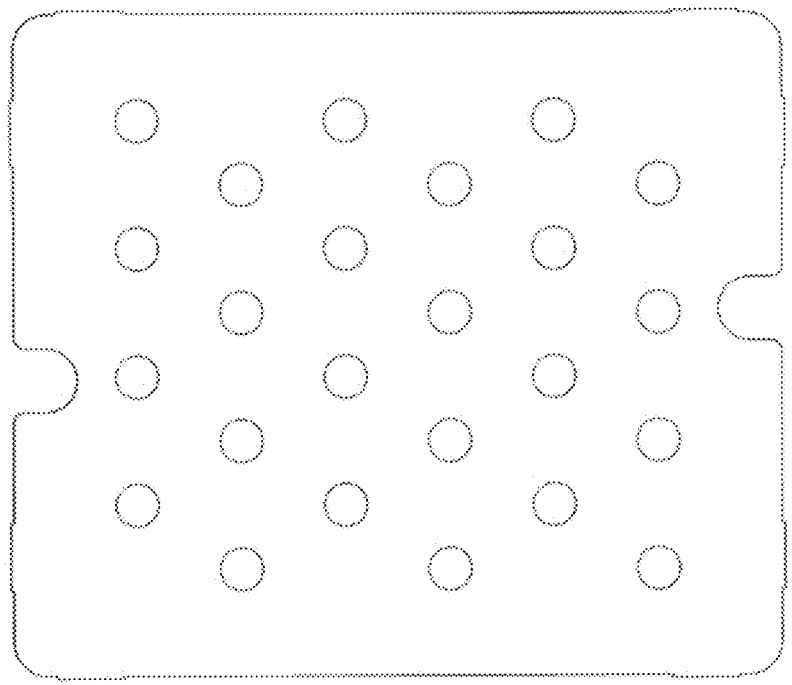
Figure 14D:
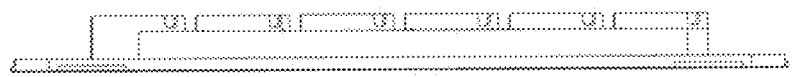
Figure 14E:
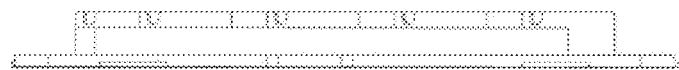
Figure 15A:
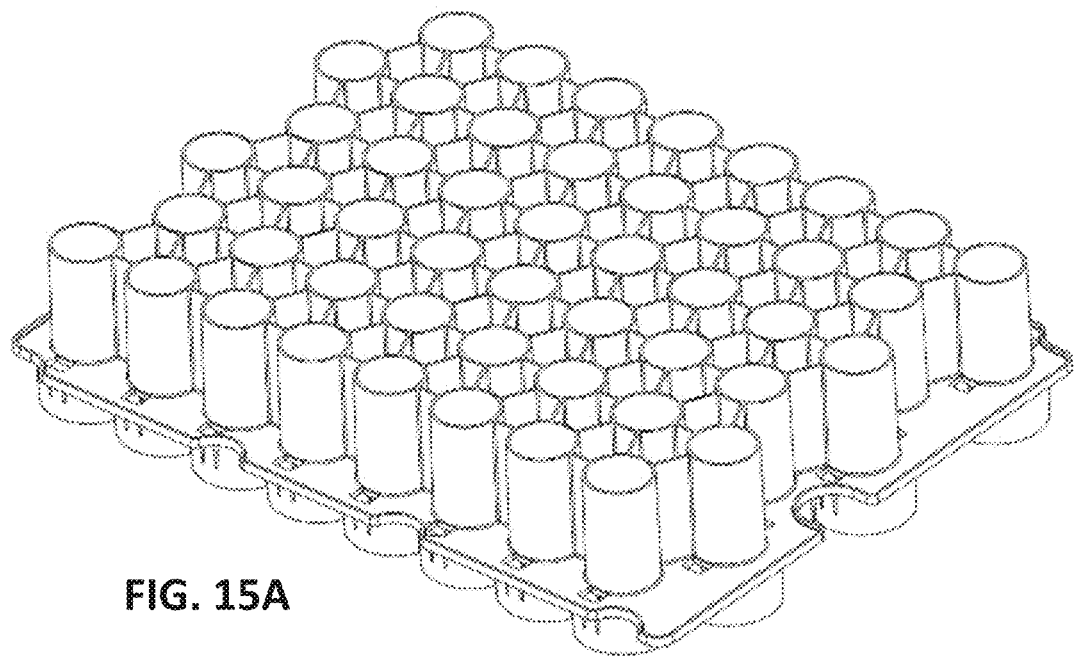
FIGS. 15A-15G are an upper perspective view, a lower perspective view, a top view, a cross-sectional view taken along the line A:A in FIG. 15C, a bottom view, a front view, and a side view, respectively, of an example variation of a pump nest with 48 dispenser seats.
Figure 15B:
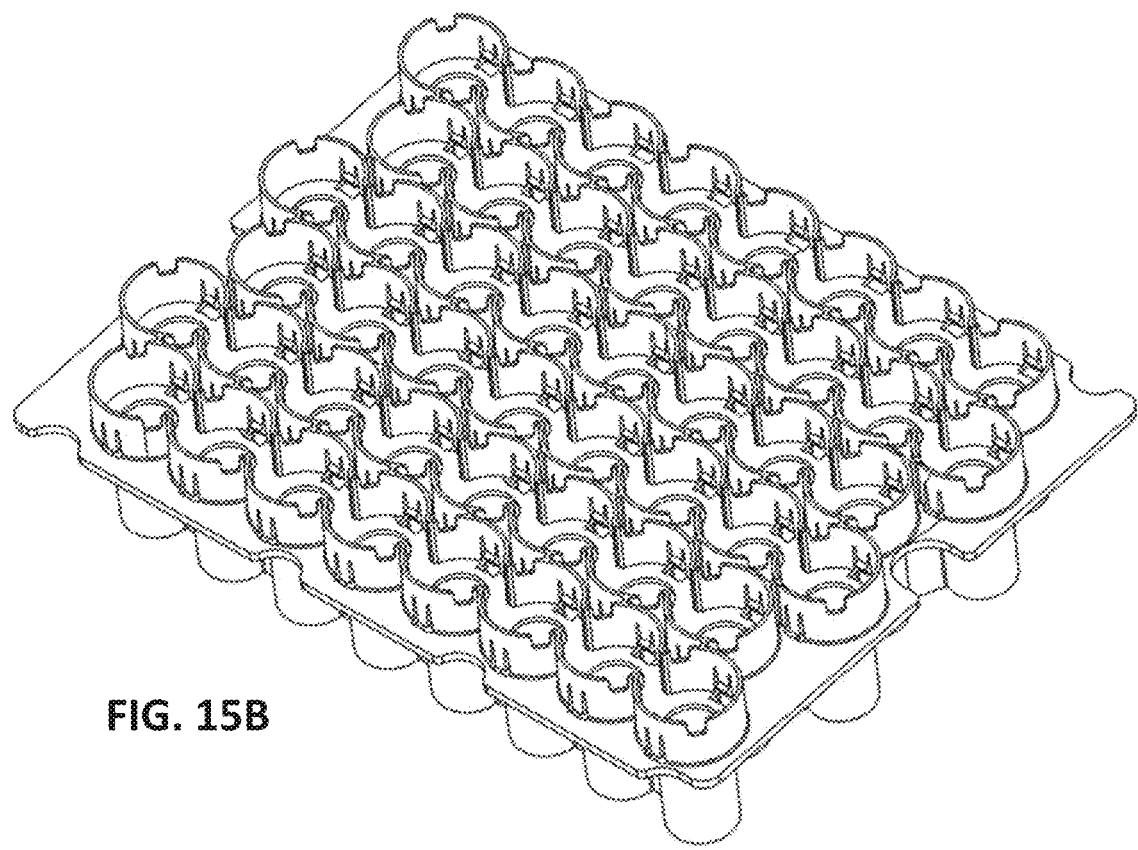
Figure 15C:
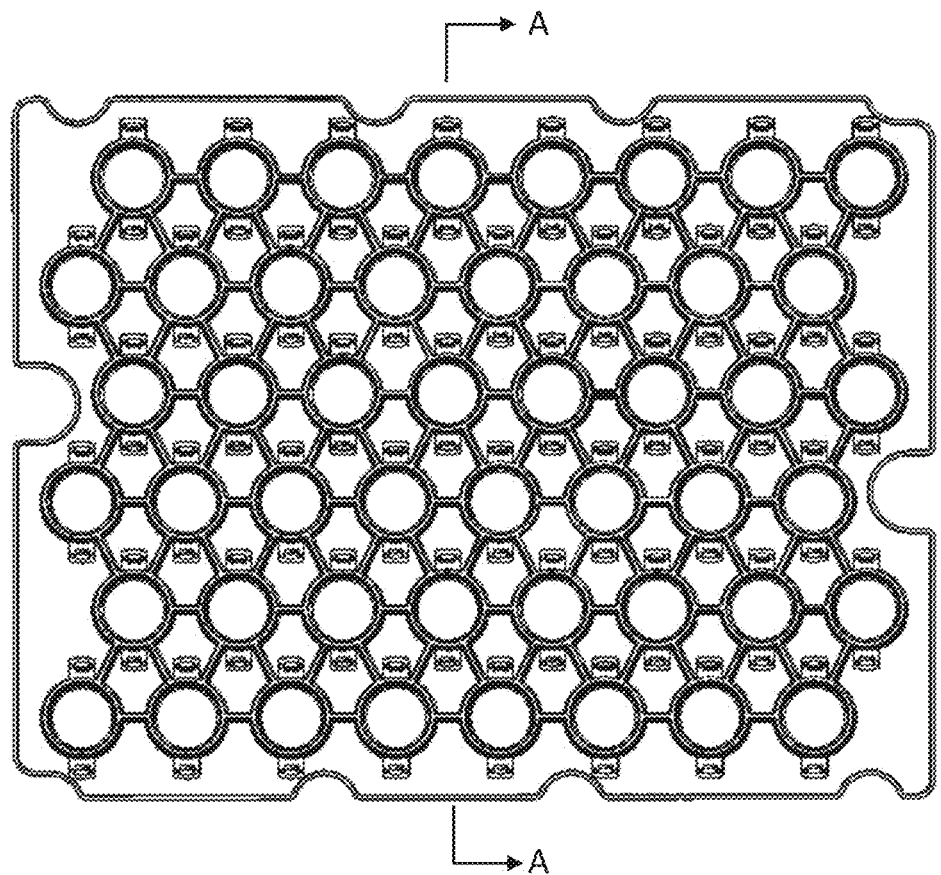
Figure 15D:
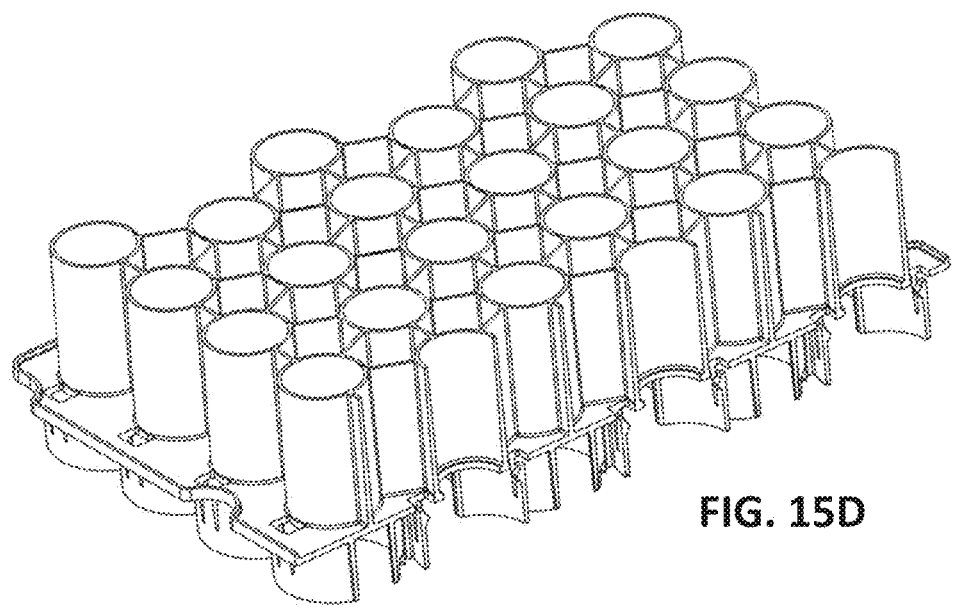
Figure 15E:
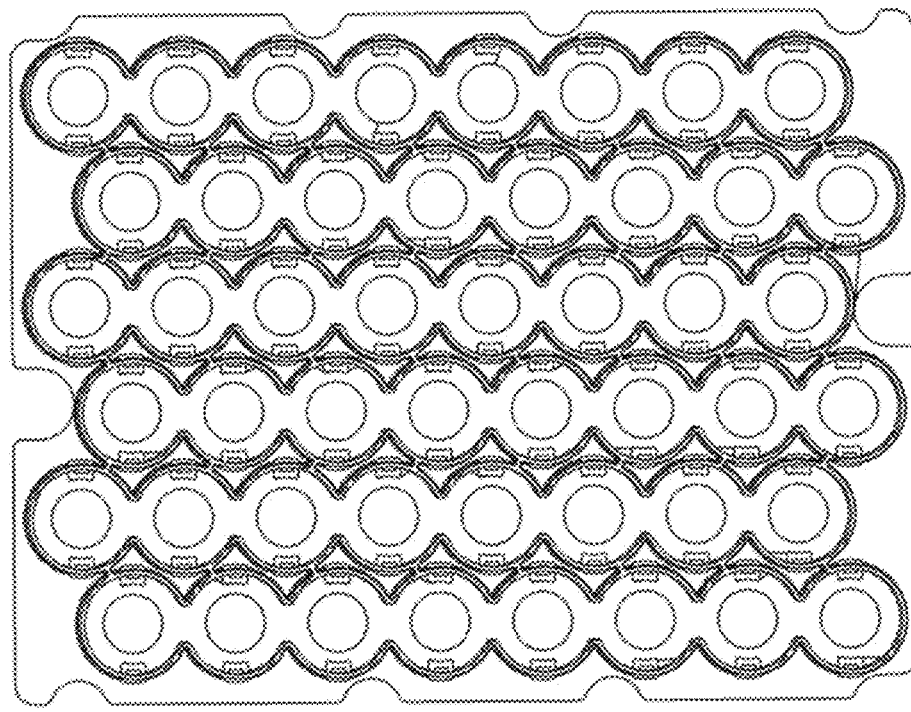
Figure 15F:
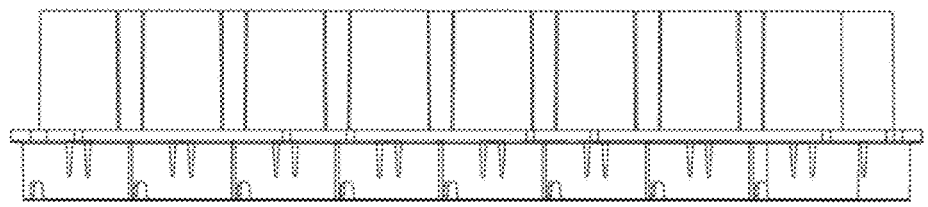
Figure 15G:
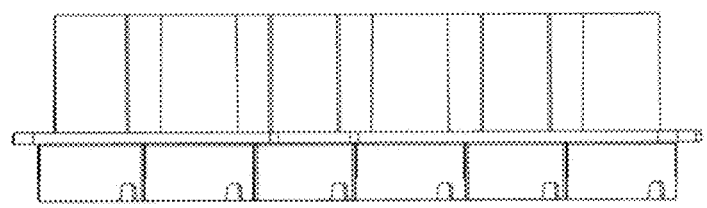
Figure 16A:
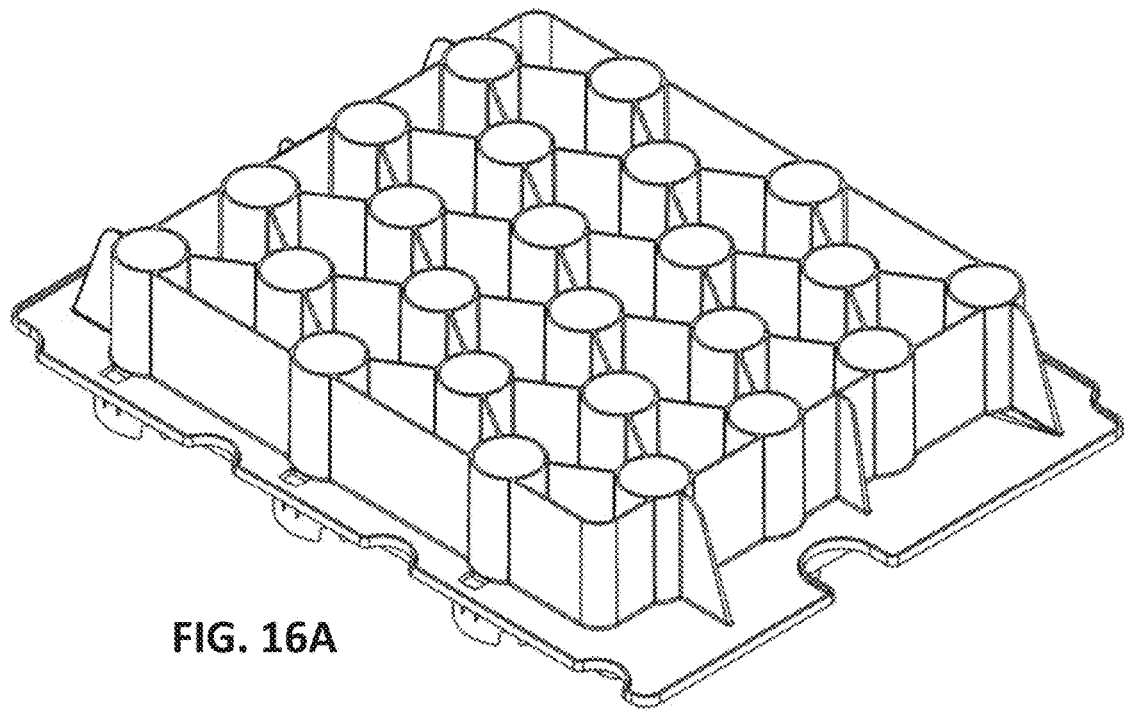
FIGS. 16A-16G are an upper perspective view, a lower perspective view, a top view, a cross-sectional view taken along the line B:B shown in FIG. 16C, a bottom view, a front view, and a side view, respectively, of an example variation of a pump nest with 24 dispenser seats.
Figure 16B:
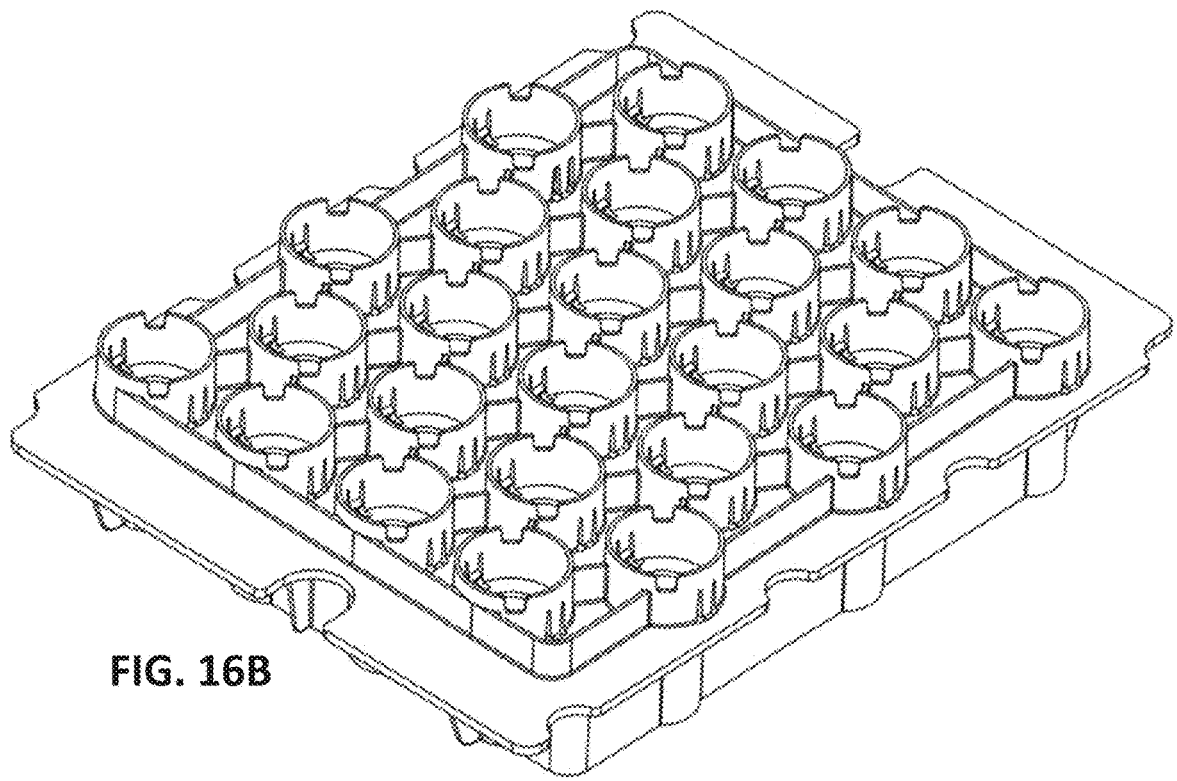
Figure 16C:
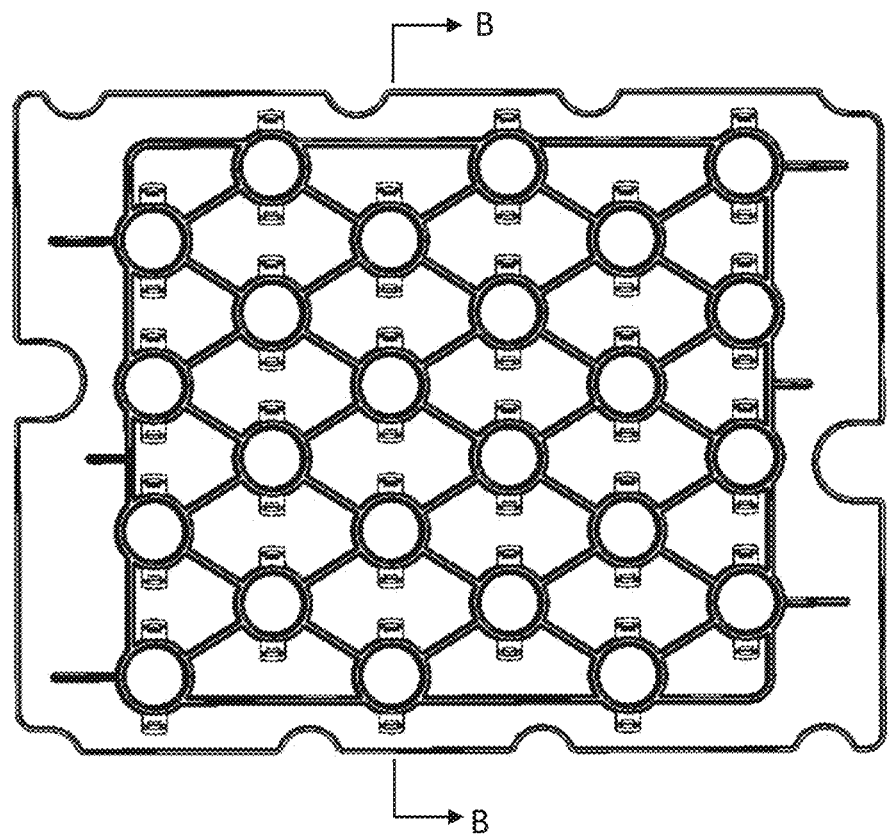
Figure 16D:
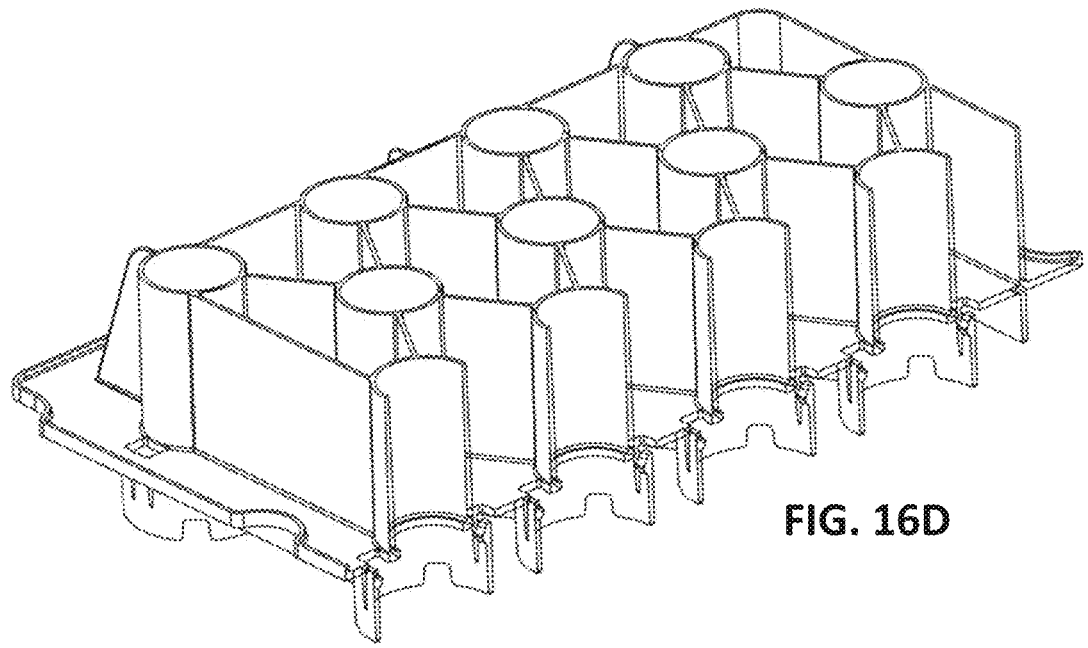
Figure 16E:
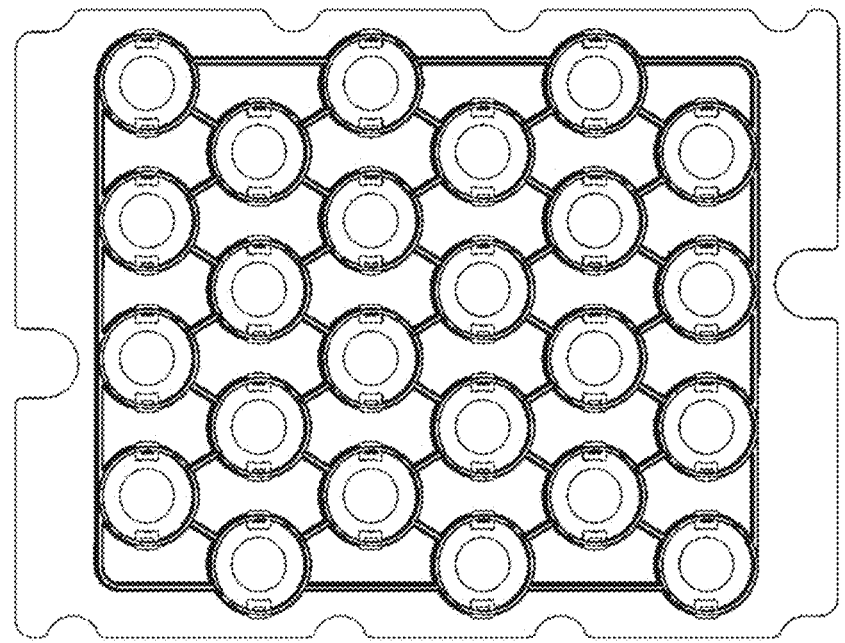
Figure 16F:
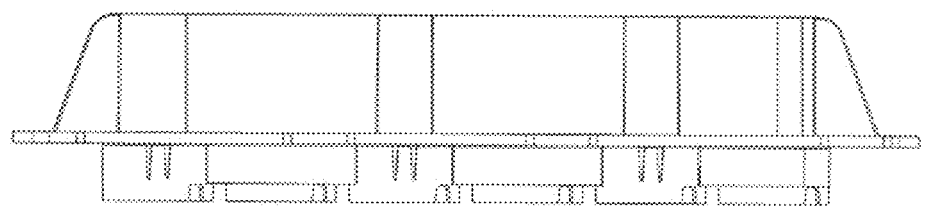
Figure 16G:
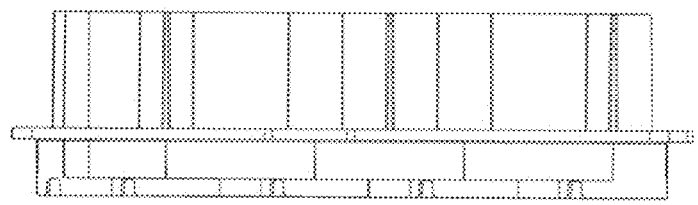
Figure 17A:
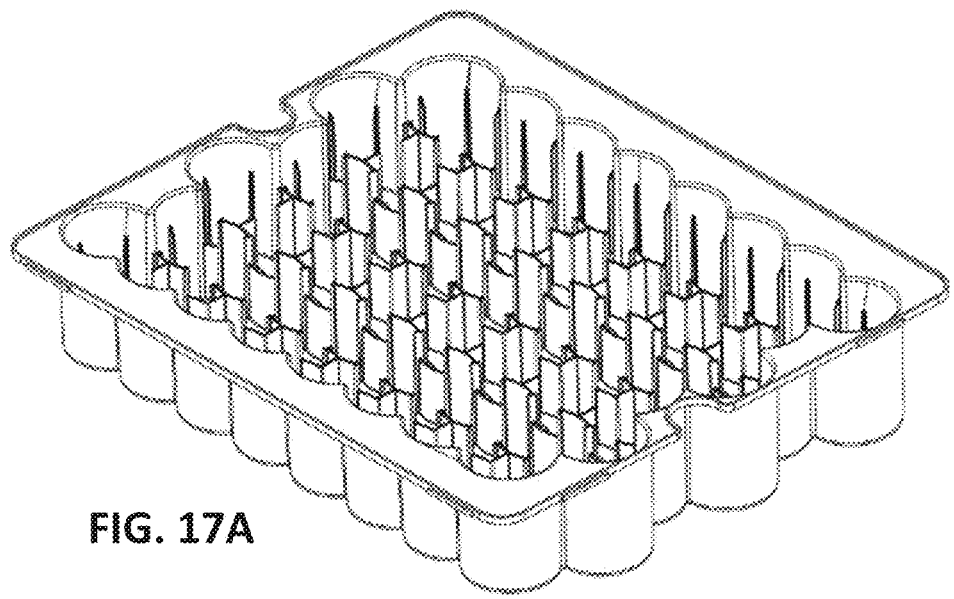
FIGS. 17A-17E are a perspective view, a top view, a bottom view, a front view, and a side view, respectively, of an example variation of a container nest.
Figure 17B:
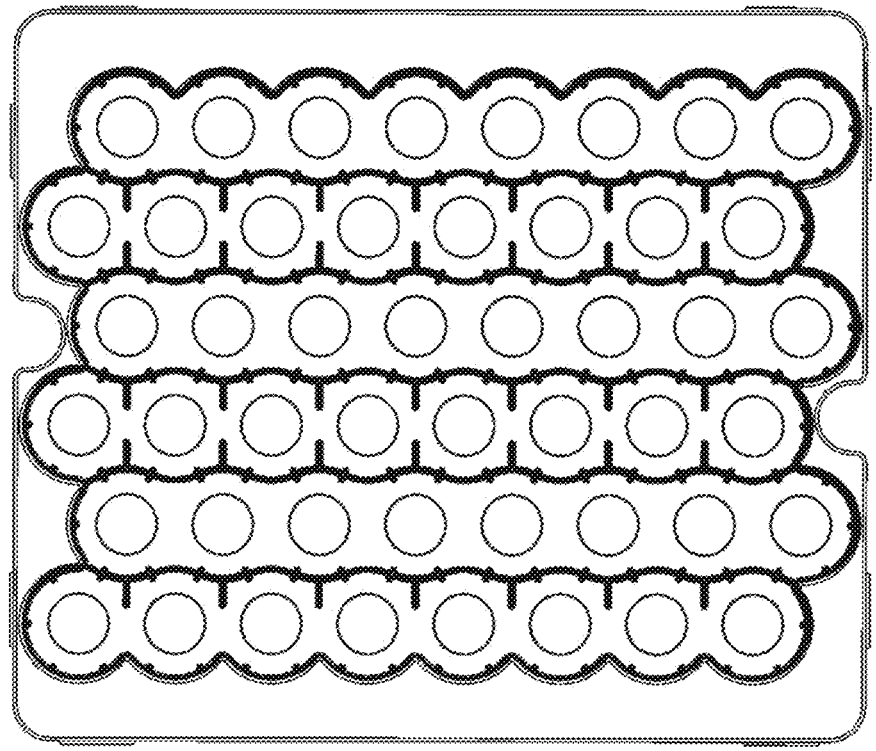
Figure 17C:
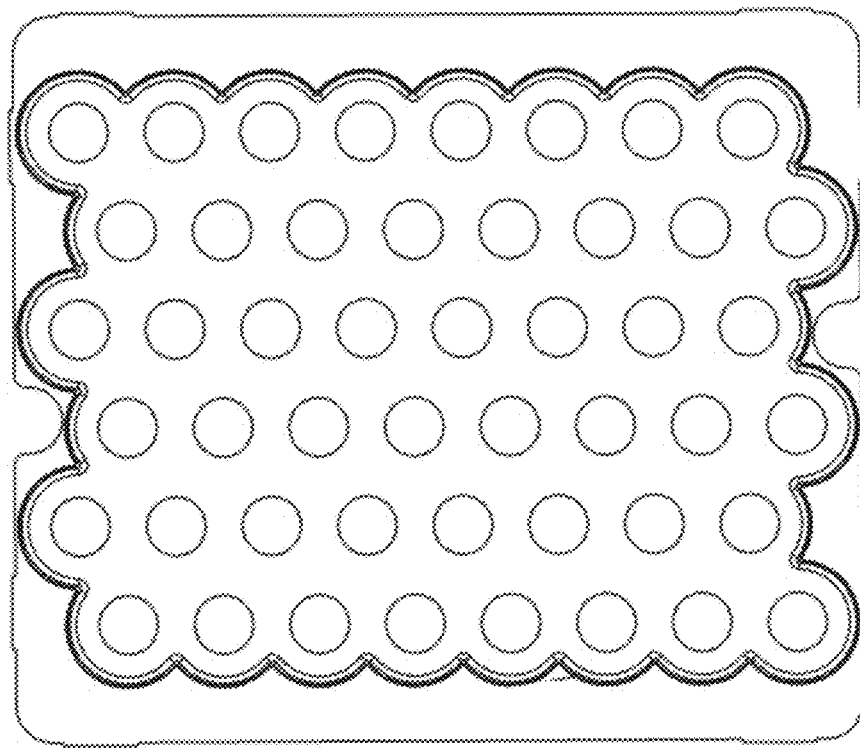
Figure 17D:
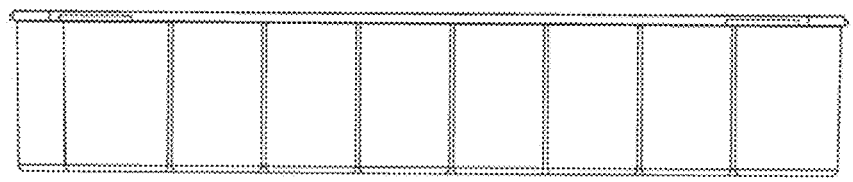
Figure 17E:
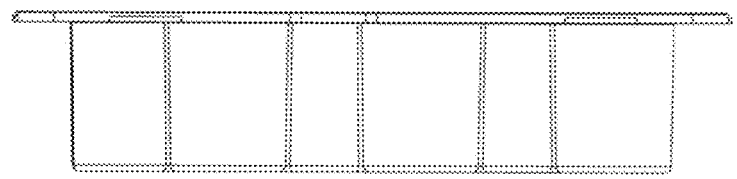
Figure 18A:
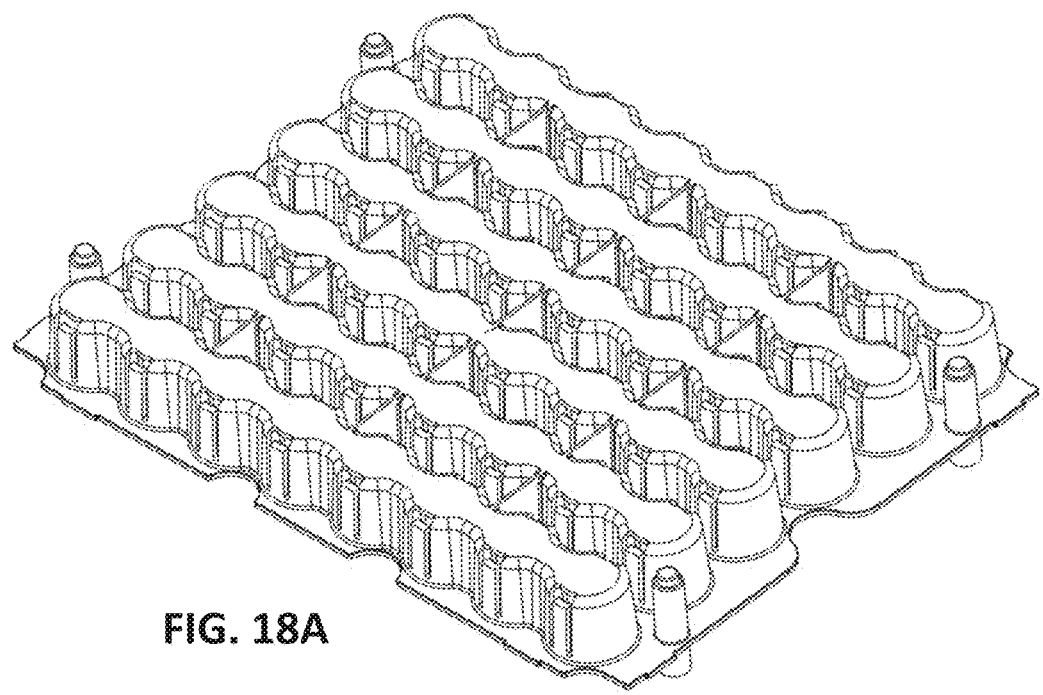
FIGS. 18A-18G are an upper perspective view, a lower perspective view, a top view, a cross-sectional view taken along the line C:C shown in FIG. 18C, a bottom view, a front view, and a side view, respectively, of an example variation of a dropper nest.
Figure 18B:
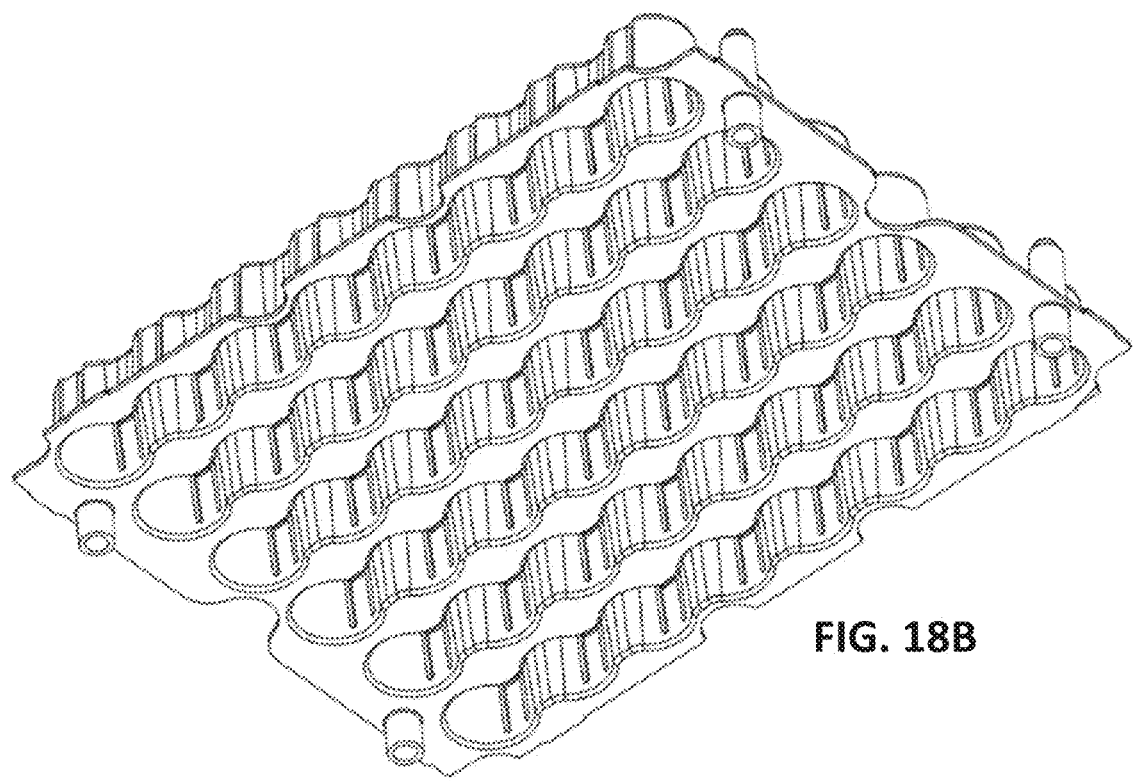
Figure 18C:
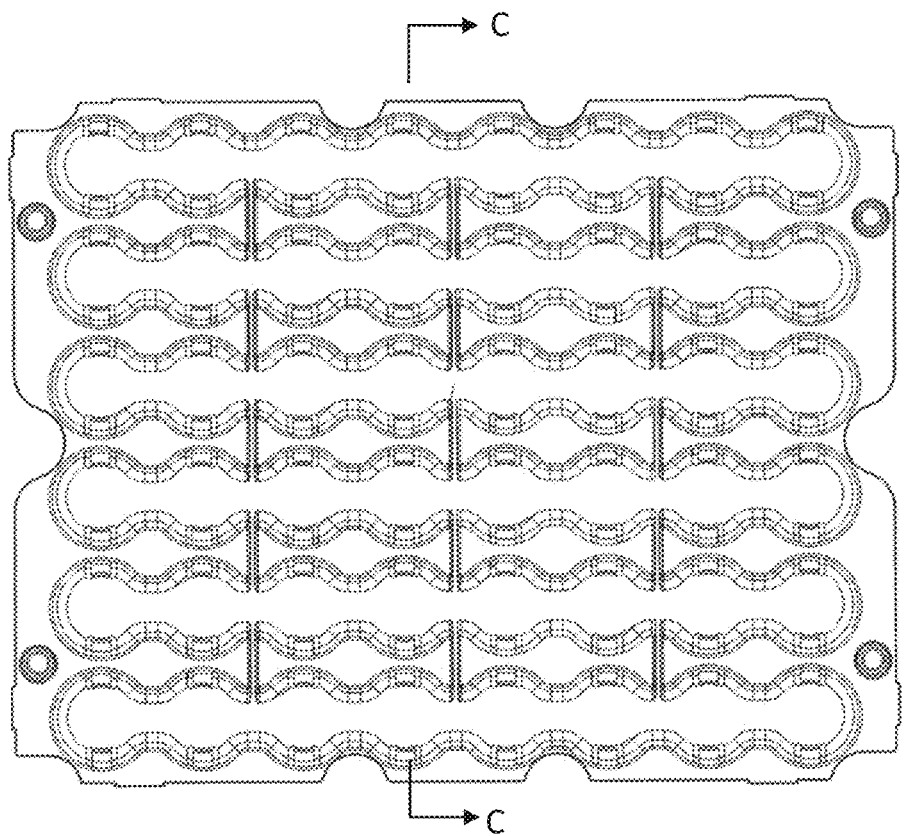
Figure 18D:
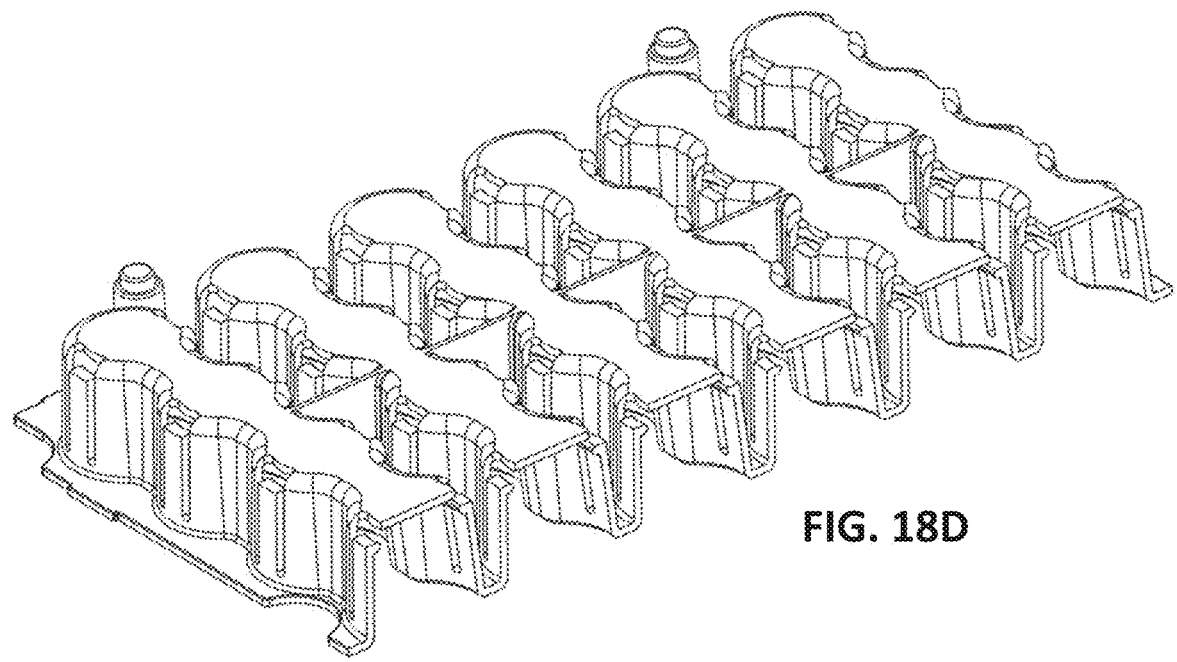
Figure 18E:
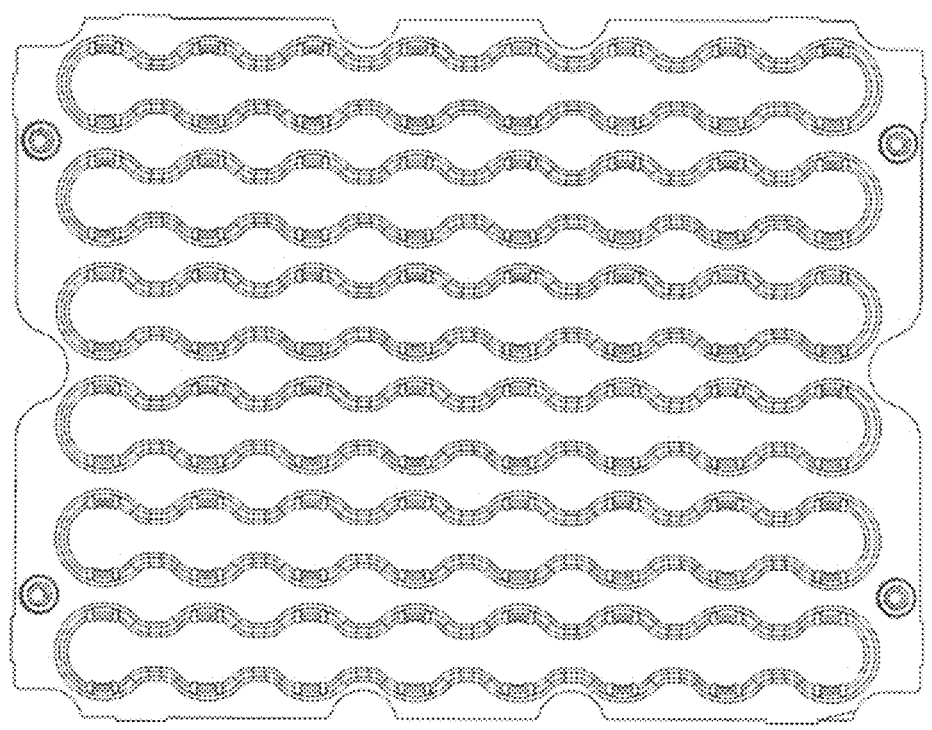
Figure 18F:
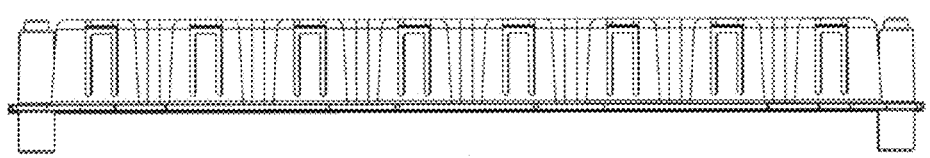
Figure 18G:
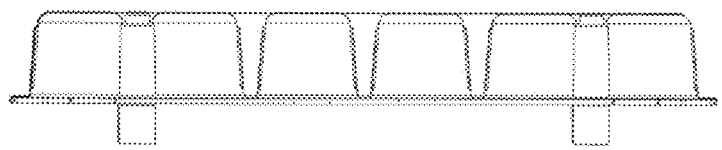

An example variation of a method for assembling drop dispenser assemblies is shown in FIG. 12, with reference to the dropper nest assembly 800 (e.g., as shown in FIG. 8A) and the dropper container nest assembly 900 (e.g., as shown in FIG. 9A). The dropper nest assembly may include a tub containing one or more stacked dropper nests (1210) and a plurality of drop dispensers (e.g., eyedropper dispensers) arranged in each dropper nest. The drop dispensers may be coupled to the dropper nests. The dropper container nest assembly may include another tub containing a dropper container nest, a plurality of dropper containers in the dropper container nest, and one or more reinforcement members arranged around the dropper containers (1220). The dropper container nest may be removed from its tub, such as with a robotic manipulator such as that described above (1222). The dropper containers in the dropper container nest may be filled with a desired substance (e.g., a liquid drug or other drug suitable for dispensing through a drop dispenser). Separately, a dropper nest may be removed from its tub, separating the dropper nest and drop dispensers from other dropper nests and the tub (1212). For example, a robotic manipulator may engage the dropper nest with suction or in another suitable manner, and because the drop dispensers are coupled to the dropper nest (e.g., via locking members as described above), manipulation of the dropper nest may efficiently enable manipulation of the drop dispensers as well. Accordingly, similar to the process described above, the robotic manipulator(s) may align the dropper nest over the dropper container nest (1240), then move the dropper nest and dropper container nest toward each other, such as by pressing the dropper nest down toward the dropper container nest. The dropper nest and dropper container nest may be moved closer together until the drop dispensers and the dropper containers couple together, such as via snap fit (1250). Accordingly, manipulation of the dropper nest and the dropper container nest may effect simultaneous assembly of multiple drop dispensers and dropper containers. Additionally or alternatively, in some variations individual drop dispensers in the dropper nest and/or individual dropper containers in the dropper container nest may be separately manipulated to form only a selected portion of the assemblies among the array of drop dispensers and dropper containers. For example, a drop dispenser may be individually accessed through an opening in its dispenser cover in the dropper nest, and pushed down toward its corresponding dropper container. Additionally or alternatively, a dropper container may be individually accessed through an opening in is container seat in the dropper container nest, and pushed up toward its corresponding drop dispenser. Multiple assemblies may be formed in such a manner, and may advantageously permit efficient assembly using the dropper nest assembly and dropper container nest assembly even if the robotic manipulator is limited in its ability to exert sufficient compressive force to form all nested assemblies simultaneously. The resulting dispenser assemblies (each including a drop dispenser coupled to a filled container) may be organized within the dropper container nest for further transport. In some variations, the dispenser assemblies may be collectively removed from the dropper container nest by again manipulating the dropper nest relative to the dropper container nest. That is, because the drop dispensers remain coupled to the dropper nest and the dropper containers are in turn coupled to the drop dispensers, the array of dispenser assemblies may be collectively manipulated with the dropper nest.

Enumerated Embodiments

Embodiment A1. A packaging structure for a plurality of drug dispensers, comprising: a support surface; and a plurality of dispenser covers arranged on the support surface; wherein at least one dispenser cover comprises a locking flexure member configured to couple a dispenser to the at least one dispenser cover.

Embodiment A2. The packaging structure of embodiment A1, wherein the flexure member is configured to engage with a radial projection of the drug dispenser.

Embodiment A3. The packaging structure of embodiment A2, wherein the flexure member is configured to flex in a radial direction relative to a central axis of the at least one dispenser cover.

Embodiment A4. The packaging structure of embodiment A3, wherein the flexure member comprises an arm extending parallel to the central axis of the at least one dispenser cover.

Embodiment A5. The packaging structure of embodiment A2, wherein the flexure member comprises a stop configured to abut the radial projection of the drug dispenser.

Embodiment A6. The packaging structure of embodiment A5, wherein the stop is configured to urge the radial projection of the drug dispenser against the at least one dispenser cover.

Embodiment A7. The packaging structure of embodiment A1, wherein the flexure member is a first flexure member, and wherein the at least one dispenser cover further comprises a second flexure member configured to retain the respective dispenser within the at least one dispenser cover.

Embodiment A8. The packaging structure of embodiment A7, wherein the first flexure member is opposite the second flexure member across the at least one dispenser cover.

Embodiment A9. The packaging structure of embodiment A1, wherein the support surface is planar.

Embodiment A10. The packaging structure of embodiment A1, further comprising at least one interconnecting wall extending between multiple dispenser covers.

Embodiment A11. The packaging structure of embodiment A1, wherein the dispenser covers are arranged in a regular array.

Embodiment A12. The packaging structure of embodiment A11, wherein the regular array is a hexagonal or rectangular array.

Embodiment A13. The packaging structure of embodiment A1, wherein the at least one dispenser cover comprises a first receptacle portion on a first side of the support surface.

Embodiment A14. The packaging structure of embodiment A13, wherein the flexure member is in the first receptacle portion.

Embodiment A15. The packaging structure of embodiment A13, wherein the at least one dispenser cover further comprises a second receptacle portion on a second side of the support surface.

Embodiment A16. The packaging structure of embodiment A1, wherein the at least one dispenser cover has a first open end and a second open end opposite the first open end.

Embodiment A17. The packaging structure of embodiment A1, wherein the at least one dispenser cover has an open end and a closed end opposite the open end.

Embodiment A18. A packaging assembly comprising the packaging structure of any one of embodiments A1 through A17, the packaging assembly further comprising a plurality of drug dispensers, wherein at least one of the drug dispensers comprises a cover for a drug container.

Embodiment A19. The packaging assembly of embodiment A18, wherein the cover comprises a spray pump.

Embodiment A20. The packaging assembly of embodiment A19, wherein the flexure member is configured to engage with a flange of the spray pump.

Embodiment A21. The packaging assembly of embodiment A18, wherein the cover comprises a drop dispenser.

Embodiment A22. The packaging assembly of embodiment A21, wherein the flexure member is configured to engage with a radial rib of the drop dispenser.

Embodiment A23. The packaging assembly of embodiment A18, further comprising a plurality of drug containers coupled to the plurality of drug dispensers.

Embodiment A24. The packaging assembly of embodiment A23, further comprising a tub containing the packaging structure, the plurality of drug dispensers, and the plurality of drug containers.

Embodiment A25. The packaging assembly of embodiment A24, wherein the tub is sealed.

Embodiment A26. The packaging assembly of embodiment A18, wherein at least one of the drug containers comprises at least one of glass and plastic.

Embodiment B1. A packaging structure for a plurality of dispensers, comprising: a support surface; and a plurality of dispenser seats arranged on the support surface, wherein at least one dispenser seat comprises a base having an opening, a wall extending from the base, and at least one alignment feature configured to engage with an engagement feature in a dispenser to thereby orient the dispenser in the at least one dispenser seat.

Embodiment B2. The packaging structure of embodiment B1, wherein the at least one dispenser seat comprises a second opening opposite the base.

Embodiment B3. The packaging structure of embodiment B1, wherein the at least one alignment feature comprises a cutout in the wall.

Embodiment B4. The packaging structure of embodiment B3, wherein the at least one alignment feature comprises a first alignment feature, and wherein the at least one dispenser seat comprises a second alignment feature.

Embodiment B5. The packaging structure of embodiment B4, wherein the first alignment feature is opposite the second alignment feature across the at least one dispenser seat.

Embodiment B6. The packaging structure of embodiment B1, wherein the support surface is planar.

Embodiment B7. The packaging structure of embodiment B6, further comprising at least one interconnecting wall extending between multiple dispenser seats.

Embodiment B8. The packaging structure of embodiment B1, wherein the dispenser seats are arranged in a regular array.

Embodiment B9. The packaging structure of embodiment B8, wherein the regular array is a hexagonal or rectangular array.

Embodiment B10. A packaging assembly comprising the packaging structure of any one of embodiments B1 through B9, the packaging assembly further comprising a plurality of drug dispensers, wherein at least one drug dispenser comprises a cover for a drug container.

Embodiment B11. The packaging assembly of embodiment B10, wherein the at least one drug dispenser comprises a drug-dispensing tube extending from the cover.

Embodiment B12. The packaging assembly of embodiment B11, wherein the cover comprises a spray pump and the drug-dispensing tube comprises a dip tube.

Embodiment B13. The packaging assembly of embodiment B10, wherein the packaging structure is a first packaging structure, wherein the packaging assembly further comprises a second packaging structure, the second packaging structure comprising a second support surface and a plurality of dispenser covers arranged on the second support surface.

Embodiment B14. The packaging assembly of embodiment B13, wherein at least one dispenser cover comprises a flexure member configured to retain a dispenser within the at least one dispenser cover.

Embodiment B15. The packaging assembly of embodiment B14, further comprising a tub containing the first packaging structure, the plurality of drug dispensers, and the second packaging structure.

Embodiment B16. The packaging assembly of embodiment B15, wherein the tub is sealed.

Embodiment C1. A method for assembling dispenser assemblies, the method comprising: providing a first support structure comprising a plurality of dispenser covers, wherein each of a plurality of dispensers is coupled to a respective dispenser cover via a locking flexure member; providing a second support structure comprising a plurality of container seats, wherein each of a plurality of containers is seated in a respective container seat; aligning the first support structure and the second support structure to align the plurality of dispensers with the plurality of containers; and manipulating at least one of the first support structure and the second support structure to simultaneously couple the plurality of dispensers to the plurality of containers.

Embodiment C2. The method of embodiment C1, wherein at least one of the dispensers comprises a cover for one of the plurality of containers.

Embodiment C3. The method of embodiment C2, wherein the cover comprises a spray pump.

Embodiment C4. The method of embodiment C2, wherein the cover comprises a drop dispenser.

Embodiment C5. The method of embodiment C1, wherein each of the plurality of dispensers is coupleable to a respective container via snap fit.

Embodiment C6. The method of embodiment C1, further comprising filling the plurality of containers with a substance.

Embodiment C7. The method of embodiment C6, wherein the substance comprises a drug.

Embodiment C8. The method of embodiment C7, wherein the drug does not comprise a preservative.

Embodiment C9. The method of embodiment C1, wherein aligning the plurality of dispensers with the plurality of containers comprises coupling a robotic manipulator to at least one of the first support structure and the second support structure.

Embodiment C10. The method of embodiment C9, wherein coupling the robotic manipulator to at least one of the first support structure and the second support structure comprises coupling the robotic manipulator to at least one of the first support structure and the second support structure with suction.

Embodiment C11. The method of embodiment C9, further comprising removing the first support structure from a tub with the robotic manipulator.

Embodiment C12. The method of embodiment C1, further comprising sterilizing the plurality of dispensers and plurality of containers.

Embodiment D1. A packaging assembly, comprising: a base; a plurality of containers arranged on the base, wherein the containers comprise a first material having a first rigidity; and at least one reinforcement member coupled to at least one container, wherein the at least one reinforcement member comprises a second material having a second rigidity greater than the first rigidity.

Embodiment D2. The packaging assembly of embodiment D1, wherein the base comprises a plurality of container seats, each container seat configured to receive a respective container.

Embodiment D3. The packaging assembly of embodiment D2, wherein the container seats are arranged in a regular array.

Embodiment D4. The packaging assembly of embodiment D3, wherein the regular array is a hexagonal array or a rectangular array.

Embodiment D5. The packaging assembly of embodiment D1, wherein the at least one reinforcement member conforms to an outer surface of at least one container.

Embodiment D6. The packaging assembly of embodiment D5, wherein the at least one reinforcement member comprises a first member portion configured to couple to a second member portion, wherein the first member portion and the second member portion, when coupled, define at least one container-receiving volume.

Embodiment D7. The packaging assembly of embodiment D6, wherein the first member portion and second member portion, when coupled, define a plurality of container-receiving volumes.

Embodiment D8. The packaging assembly of embodiment D6, wherein the at least one container-receiving volume is cylindrical.

Embodiment D9. The packaging assembly of embodiment D1, further comprising a tub containing the base, the plurality of containers, and the at least one reinforcement member.

Embodiment D10. The packaging assembly of embodiment D9, wherein the tub is sealed.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A method for assembling dispenser assemblies, the method comprising:
   providing a first support structure comprising a plurality of dispenser covers, wherein each of a plurality of dispensers is coupled to a respective dispenser cover via a locking flexure member;
   providing a second support structure comprising a plurality of container seats, wherein each of a plurality of containers is seated in a respective container seat;
   aligning the first support structure and the second support structure to align the plurality of dispensers with the plurality of containers; and
   manipulating at least one of the first support structure and the second support structure to simultaneously couple the plurality of dispensers to the plurality of containers.

2. A packaging assembly, comprising:
   a base;
   a plurality of containers arranged on the base, wherein the containers comprise a first material having a first rigidity; and
   at least one reinforcement member coupled to at least one container, wherein the at least one reinforcement member comprises a second material having a second rigidity greater than the first rigidity.

3. A packaging assembly comprising:
   a) a packaging structure comprising a support surface and a plurality of dispenser covers arranged on the support surface, wherein at least one dispenser cover comprises a locking flexure member configured to couple a drug dispenser to said dispenser cover; and
   b) a second support surface including a plurality of dispenser seats arranged on the second support surface, wherein at least one dispenser seat comprises a base having an opening, a wall extending from the base, and at least one alignment feature configured to engage with an engagement feature in a drug dispenser to thereby orient the drug dispenser in the at least one dispenser seat.

4. The packaging assembly of claim 3, wherein the at least one dispenser seat comprises a second opening opposite the base.

5. The packaging assembly of claim 3, wherein the at least one alignment feature comprises a cutout in the wall.

6. The packaging assembly of claim 3, further comprising a plurality of drug dispensers, wherein at least one of the drug dispensers comprises a cover for a drug container.

7. The packaging assembly of claim 6, wherein the cover comprises a spray pump.

8. The packaging assembly of claim 6, wherein the cover comprises a drop dispenser.

9. The packaging assembly of claim 6, further comprising a plurality of drug containers coupled to the plurality of drug dispensers.

* * * * *